US011590092B2

(12) United States Patent
Huang

(10) Patent No.: US 11,590,092 B2
(45) Date of Patent: Feb. 28, 2023

(54) SKIN PROBIOTIC

(71) Applicant: The Regents of the University of California, Oakland, CA (US)

(72) Inventor: Chun-Ming Huang, San Diego, CA (US)

(73) Assignee: The Regents of the University of California, Oakland, CA (US)

(*) Notice: Subject to any disclaimer, the term of this patent is extended or adjusted under 35 U.S.C. 154(b) by 418 days.

(21) Appl. No.: 16/432,864

(22) Filed: Jun. 5, 2019

(65) Prior Publication Data

US 2019/0282523 A1 Sep. 19, 2019

Related U.S. Application Data

(62) Division of application No. 15/110,730, filed as application No. PCT/US2015/010926 on Jan. 10, 2015.

(60) Provisional application No. 61/926,055, filed on Jan. 10, 2014.

(51) Int. Cl.
*A61K 31/19* (2006.01)
*A61K 31/047* (2006.01)
*A61K 31/194* (2006.01)
*A61K 31/22* (2006.01)
*A61K 9/06* (2006.01)
*A61K 31/225* (2006.01)
*A61K 45/06* (2006.01)
*C12Q 1/04* (2006.01)
*A61K 9/00* (2006.01)
*A61K 35/741* (2015.01)
*A61K 35/00* (2006.01)

(52) U.S. Cl.
CPC ............ *A61K 31/19* (2013.01); *A61K 9/0014* (2013.01); *A61K 9/06* (2013.01); *A61K 31/047* (2013.01); *A61K 31/194* (2013.01); *A61K 31/22* (2013.01); *A61K 31/225* (2013.01); *A61K 35/741* (2013.01); *A61K 45/06* (2013.01); *C12Q 1/04* (2013.01); *A61K 2035/115* (2013.01); *G01N 2500/10* (2013.01)

(58) Field of Classification Search
CPC combination set(s) only.
See application file for complete search history.

(56) References Cited

U.S. PATENT DOCUMENTS

2011/0104240 A1 5/2011 Jones et al.
2011/0189347 A1 8/2011 Broz et al.

FOREIGN PATENT DOCUMENTS

WO 2012131069 A1 10/2012

OTHER PUBLICATIONS

Asay, R.E. et al., "The synthesis of novel macrocyclic multidentate compounds from dioxodioic acids", Journal of Heterocyclic Chemistry, Feb. 1, 1977, 14: 85-90.
Barbirato et al., Appl. Microbiol. Biotechnol., 47:441-446, 1997.
Domenech et al., "Effect of six organic acids on staphylococcal growth and enterotoxin production," Z Lebensm Unters Forsch., 194(2):124-128—1992.
Lindner, Nora, International Preliminary Report on Patentability and Written Opinion, The International Bureau of WIPO, PCT/US2015/010926, dated Jul. 21, 2016.
Shu et al., "Fermentation of Propionbacterium acnes, a Commensal Bacterium in the Human Skin Microbiome, as Skin Probiotics against Methicillin-Resistant *Staphylococcus aureus*," PLOS One, 8(2):e55380, Feb. 1-11, 2013.
Shulka, P. et al., "Activity of alkanediol alkanoates against pathogenic plant fungi *Rhizoctonia solani* and *Sclerotium rolfsii*", Database Accession No. 2012:1462242, Natural Product Communications, 7(9), 1219-1222.
Sikorska, Hanna et al., "Role of probiotics in the prevention and treatment of meticillin-resistant *Staphylococcus aureus* infections", International Journal of Antimicrobial Agents, vol. 42, No. 6, Dec. 1, 2013, pp. 475-481.
Steendijk, Martin, Extended European Search Report, European Patent Office, Application No. EP15735010, dated Aug. 9, 2017.
Wang, Y. et al., "Propionic acid and its esterified derivative suppress the growth of methicillin-resistant *Staphylococcus aureus* USA300", Beneficial Microbes, vol. 5, No. 2, Mar. 31, 2014, pp. 161-168.
Wang et al., "*Staphylococcus epidermidis* in the human skin microbiome mediates fermentation to inhibit the growth of Propionibacterium acnes: Implications of probioteics in acne vulgaris," Appl. Microbiol. Biotechnol., 98(1):411-424, Nov. 22, 2013.
Webster et al., "ACNE and its THERAPY, Basic and Clinical Dermatology," CRC Press, May 17, 2007, 328 Pages, p. 2 only.
Definition of "extract" from GOOGLE Dictionary, downloaded on Jun. 5, 2018, 1 page.
Millipore, "Sterile Filtration of Serum-free Mammalian Cell Culture Media," 2007, p. 2-11.

*Primary Examiner* — Kathrien A Hartsfield

(74) *Attorney, Agent, or Firm* — Gavrilovich, Dodd & Lindsey LLP

(57) ABSTRACT

The disclosure provides skin probiotics, fermented media extract and fermentation byproducts thereof for the treatment of skin disease and disorders as well as for the prevention/treatment of acne and MRSA.

10 Claims, 23 Drawing Sheets

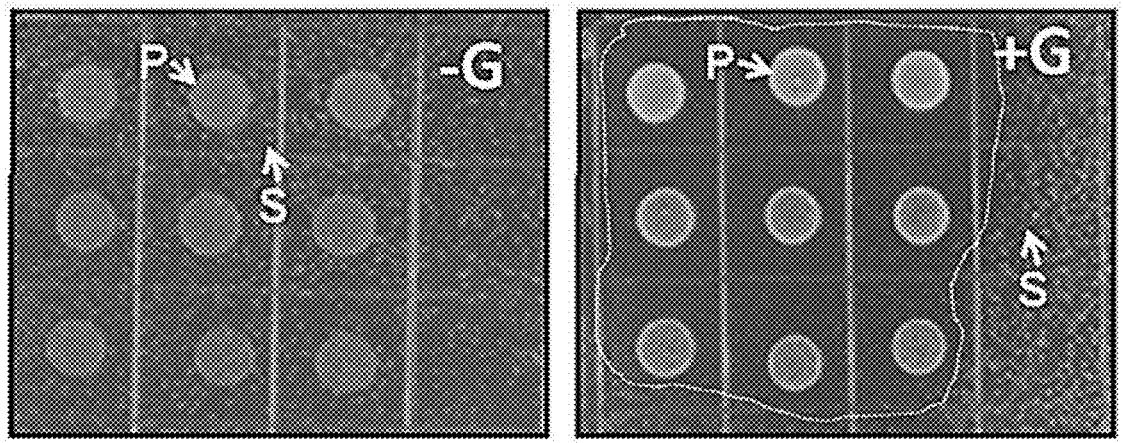
FIG. 1C
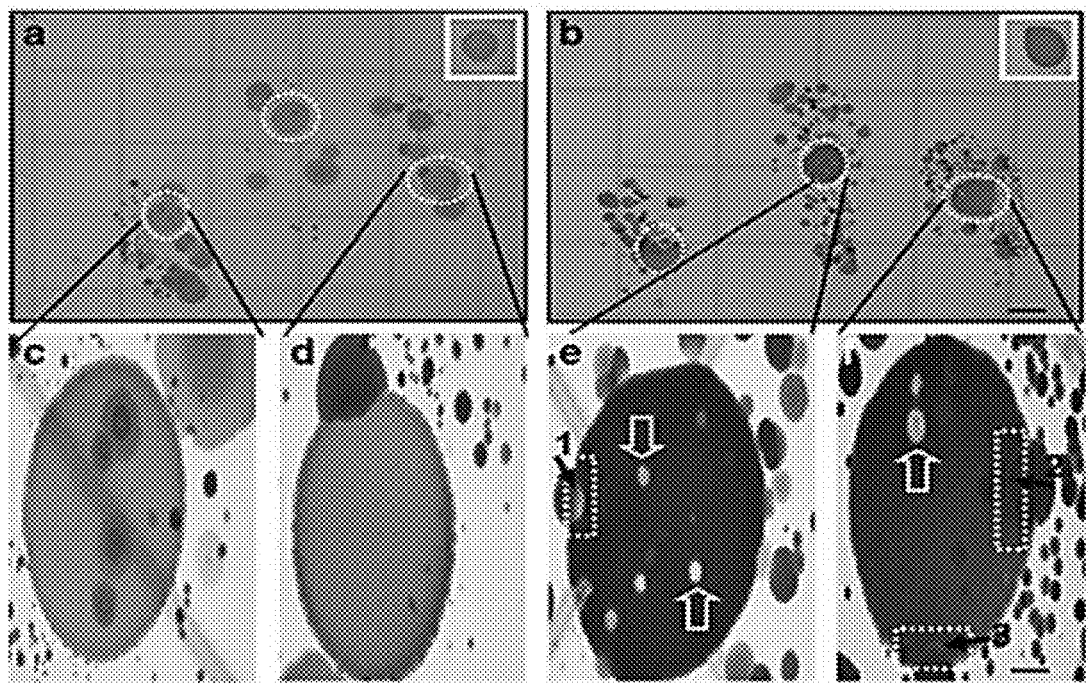
FIG. 2A-F

P. acnes

+ Glycerol

− Glycerol

M. luteus

+ Glycerol

− Glycerol

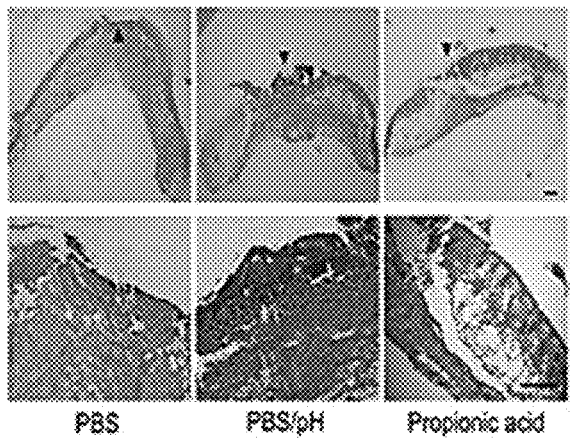
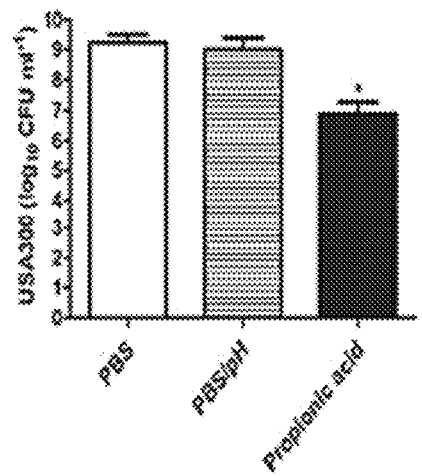
FIG. 10E
FIG. 10F
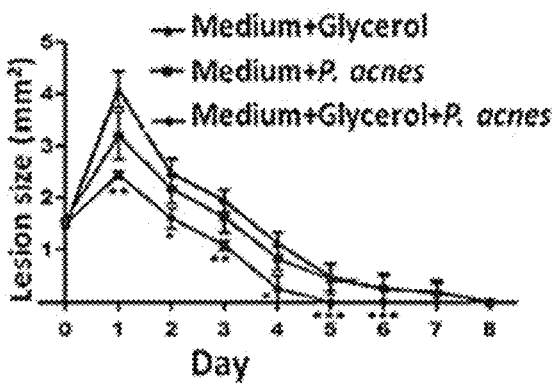
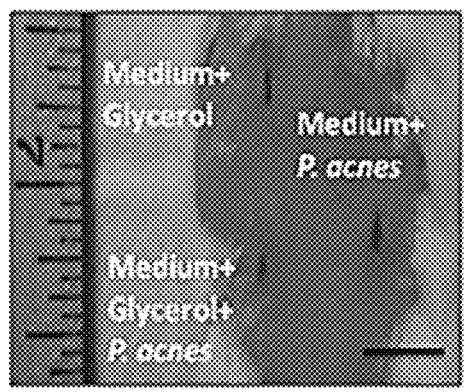
FIG. 11A
FIG. 11B
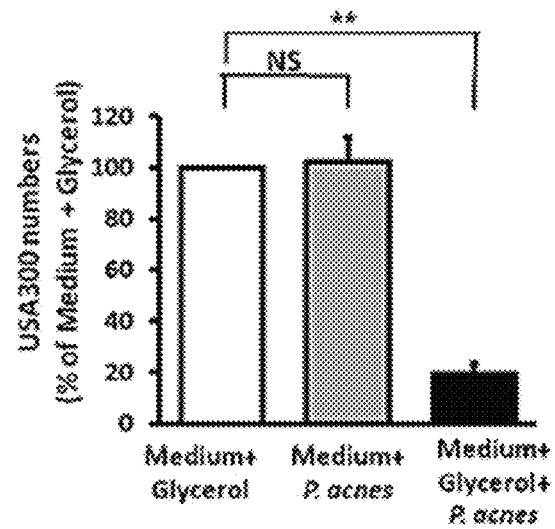
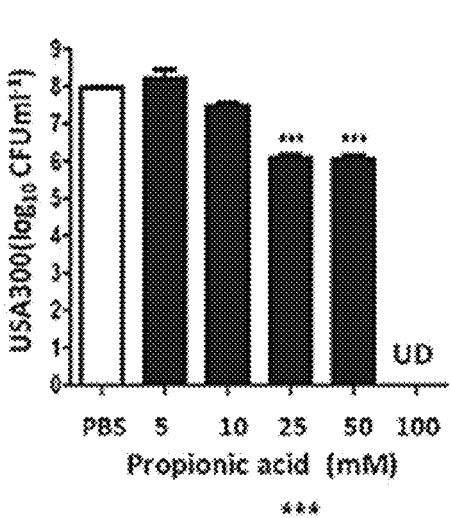
FIG. 11C
FIG. 11D

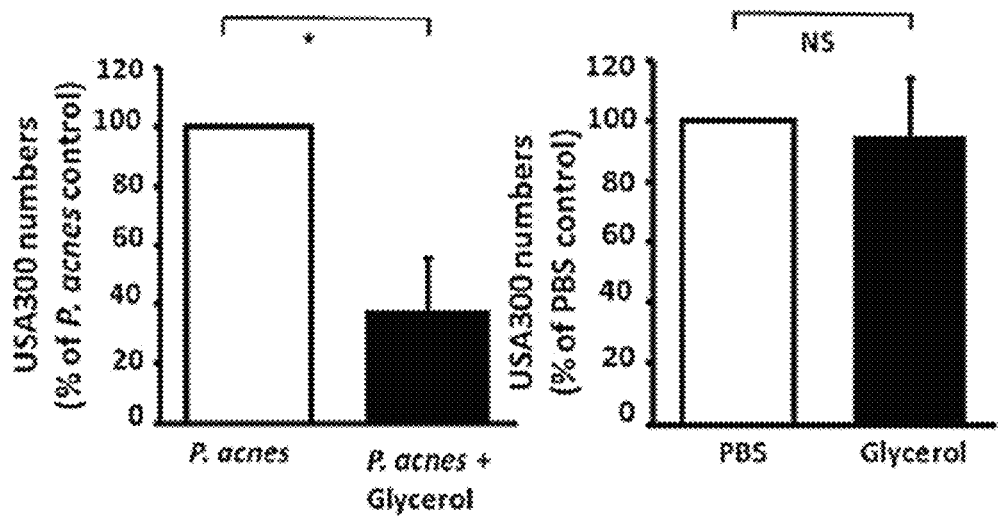
FIG. 13C
FIG. 13D
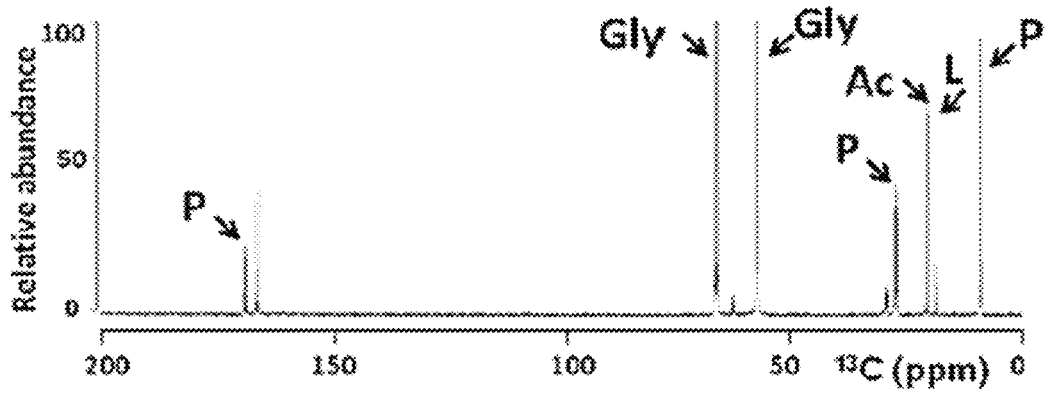
FIG. 14A
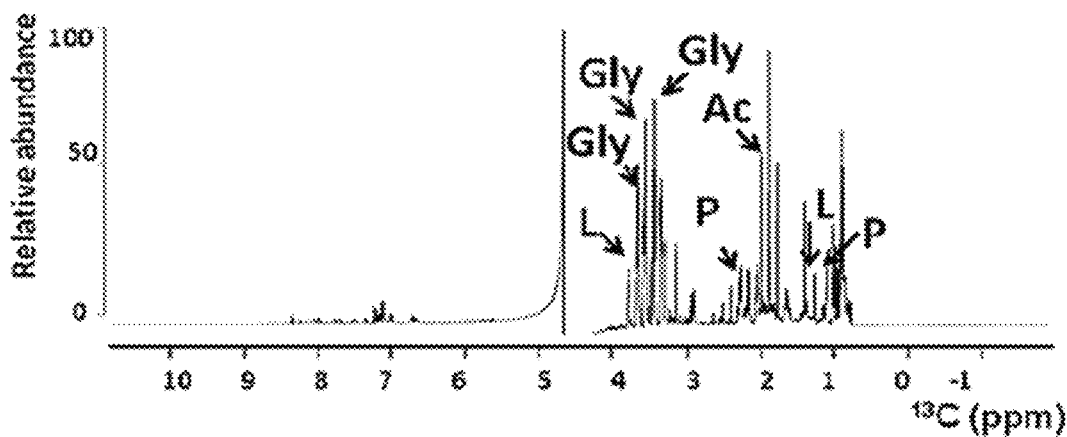
FIG. 14B

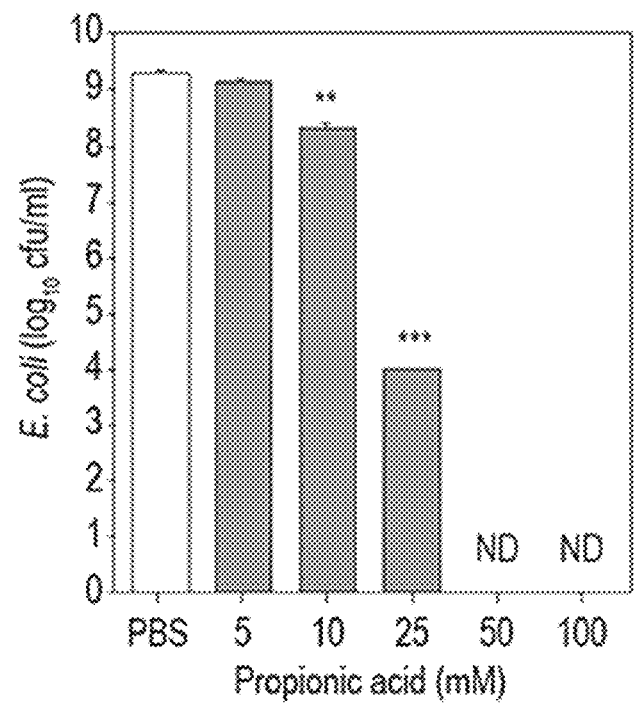
FIG. 18B
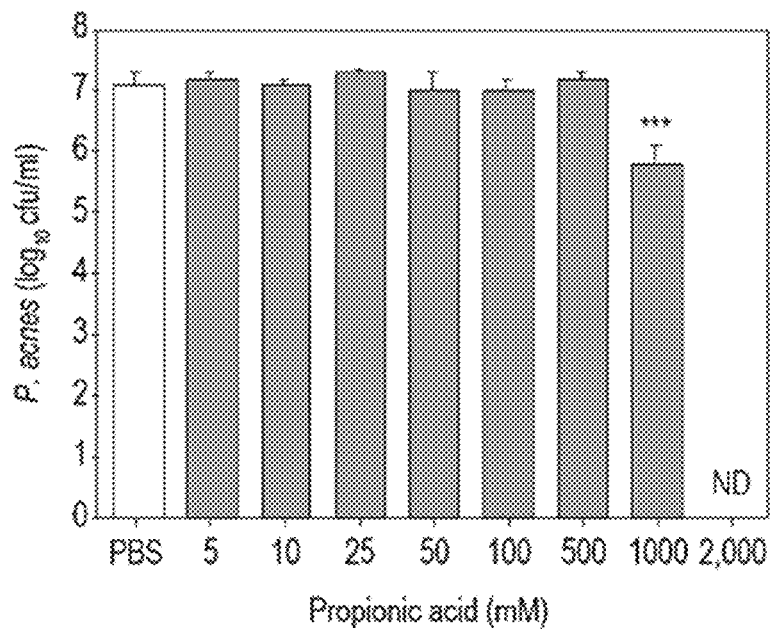
FIG. 19
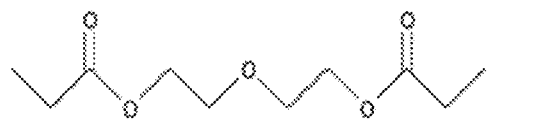 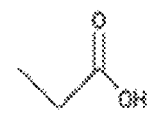
FIG. 20A                FIG. 20B

SKIN PROBIOTIC

CROSS REFERENCE TO RELATED APPLICATIONS

This application is a divisional of U.S. application Ser. No. 15/110,730, having a filing date of Jul. 8, 2016, which application is a U.S. National Stage Application filed under 35 U.S.C. § 371 and claims priority to International Application No. PCT/US2015/010926, filed Jan. 10, 2015, which application claims priority under 35 U.S.C. § 119 from Provisional Application Ser. No. 61/926,055, filed Jan. 10, 2014, the disclosures of which are incorporated herein by reference.

STATEMENT REGARDING FEDERALLY SPONSORED RESEARCH

This invention was made with Government support under Grant Nos. 1R21AI088147, R01 AI083358 and R41 AR064046, awarded by the National Institutes of Health. The Government has certain rights in this invention.

TECHNICAL FIELD

The disclosure provide skin probiotics and extracts for the treatment of skin infection, diseases and disorders.

BACKGROUND

Fermentation of milk with gut-friendly bacteria, yogurt, is a great example of bacterial antagonism (interference) via fermentation, and an excellent aid to balancing the bacteriological ecosystem in the human intestine. Bacterial antagonism via fermentation occurs in other natural ecosystems as well. For example, microorganisms both on and inside fruits consume sugars, converted from starch during ripening, to produce fermentation products including ethanol and short-chain fatty acids (SCFAs). Production of SCFAs and ethanol by fermentative yeasts is, in fact, a part of an evolved strategy to compete with other microbes for access to sugars.

Bacterial antagonism also occurs on skin, and in particular human skin. However, it has yet to be described how bacterial antagonism affects the skin microbiome, and various diseases or disorders caused by an imbalance in the skin microbiome. Several publications disclose the effect of inflammation in diseases and disorders of the skin. Other publications disclose the use of SCFAs to direct human immune response towards an increase in Th1 and decrease in Th2 and towards the switch from Th2 to Th1 responses. However, no publication has described the use of SCFAs to balance the microbiome, particularly on human skin.

Therefore, what is needed are compositions and methods for affecting diseases and disorders of the skin using SCFAs to balance the skin microbiome.

SUMMARY

The disclosure describes topical probiotic composition for producing or maintaining skin microbiome balance. In one embodiment, a topical probiotic composition is provided that is capable of producing or maintaining skin microbiome balance. The composition can comprise a therapeutically effective amount or inhibiting effective amount of one or more microbiome balancing compounds. The compounds can have the structure of Formula I:

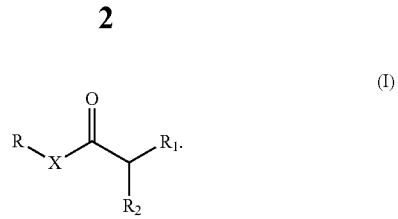

In various aspects, X can be selected from —O—, —S—, and —NH—; R, $R_1$, and $R_2$ can be independently selected from the group consisting of hydrogen, and optionally substituted ($C_1$-$C_{12}$)alkyl, optionally substituted hetero-($C_1$-$C_{12}$) alkyl, optionally substituted ($C_1$-$C_{12}$) alkenyl, optionally substituted hetero-($C_1$-$C_{12}$) alkenyl, optionally substituted ($C_1$-$C_{12}$)alkynyl, optionally substituted hetero-($C_1$-$C_{12}$) alkynyl, optionally substituted ($C_1$-$C_{12}$) cycloalkyl, optionally substituted ($C_1$-$C_{12}$)cycloalkenyl, optionally substituted aryl, optionally substituted heterocycle, and optionally substituted mixed ring system, and —O—$R_3$—O—Y;

$R_3$ is selected from the group consisting of an optionally substituted ($C_1$-$C_{12}$)alkyl, optionally substituted hetero-($C_1$-$C_{12}$)alkyl, optionally substituted ($C_1$-$C_{12}$)alkenyl, optionally substituted hetero-($C_1$-$C_{12}$)alkenyl, optionally substituted ($C_1$-$C_{12}$)alkynyl, and optionally substituted hetero-($C_1$-$C_{12}$) alkynyl; and Y can be another compound of Formula I, or can be selected from the group consisting of

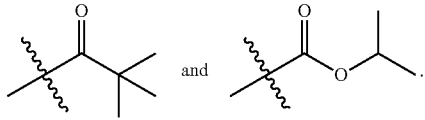

In another aspect, pharmaceutically acceptable salts of the compound are provided. In yet another aspect, the optional substituent can be independently selected from the group consisting of carboxyl, nitro, halogen, amino, hydroxyl, cyano, methoxy, polyalkylene glycol, and phenyl, further wherein the phenyl group may be optionally substituted with one or more substituents selected from the group consisting of carboxyl, nitro, halogen, amino, hydroxyl, cyano, methoxy, and polyalkylene glycol.

In another embodiment, the composition can comprise a therapeutically effective amount or inhibiting effective amount of one or more compounds having the structure of Formula II:

In one aspect, $R^1$ can be selected from an optionally substituted ($C_1$-$C_6$)alkyl; $R^2$ can be selected from a hydroxyl, —O—$CH_2$—$R^3$, and —O—$R^4$—O—X; $R^3$ can be selected from H, optionally substituted ($C_1$-$C_{12}$)alkyl, optionally substituted hetero-($C_1$-$C_{12}$)alkyl, optionally substituted ($C_1$-$C_{12}$)alkenyl, optionally substituted hetero-($C_1$-$C_{12}$)alkenyl, optionally substituted ($C_1$-$C_{12}$)alkynyl, optionally substituted hetero-($C_1$-$C_{12}$)alkynyl, optionally substituted ($C_1$-$C_{12}$)cycloalkyl, optionally substituted ($C_1$-$C_{12}$)cycloalkenyl, optionally substituted aryl, optionally substituted heterocycle, and optionally substituted mixed ring system; and $R^4$ can be selected from the group consisting of an optionally substituted $(C_1-C_{12})$alkyl, optionally substituted hetero-$(C_1-C_{12})$alkyl, optionally substituted $(C_1-C_{12})$alkenyl, optionally substituted hetero-$(C_1-C_{12})$alkenyl, optionally substituted $(C_1-C_{12})$alkynyl, and optionally substituted hetero-$(C_1-C_{12})$alkynyl. In another aspect, X can be either another compound of Formula II, or selected from the group consisting of

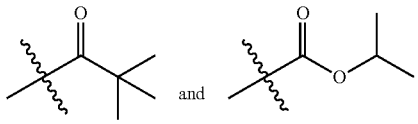

wherein, when $R^2$ is a hydroxyl then the pharmaceutical composition comprises at least two compounds comprising the structure of Formula II. In yet another aspect, pharmaceutically acceptable salts of the compounds are provided.

In accordance with a further aspect, the composition comprises one or more compounds comprising the structure of Formula II. In various aspects, $R^1$ can be selected from an optionally substituted $(C_1-C_6)$alkyl; $R^2$ can be selected from a hydroxyl, —O—$CH_2$—$R^3$, and —O—$R^4$—O—X; $R^3$ can be selected from H or an optionally substituted $(C_1-C_{12})$ alkyl; $R^4$ can be selected from an optionally substituted $(C_1-C_{12})$alkyl or an optionally substituted hetero-$(C_1-C_{12})$ alkyl; and X can be either another compound of Formula II, or selected from

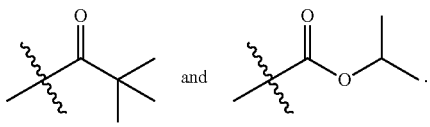

In another aspect, pharmaceutically acceptable salts of the compound are provided.

In accordance with a further aspect, the composition comprises two or more compounds comprising the structure of Formula II. In various aspects, $R^1$ can be selected from an optionally substituted $(C_1-C_6)$alkyl; and $R^2$ can be a hydroxyl. In another aspect, pharmaceutically acceptable salts of the compound are provided.

In accordance with a further aspect, the composition comprises one or more compounds comprising the structure of Formula II. In various aspects, $R^1$ can be selected from an optionally substituted $(C_1-C_6)$alkyl; $R^2$ can be selected from —O—$CH_2$—$R^3$ and —O—$R^4$—O—X; $R^3$ can be selected from H or an optionally substituted $(C_1-C_{12})$alkyl; and $R^4$ can be selected from —$(CH_2)$—, —$(CH_2)_2$—, and —$(CH_2)_2$—O—$(CH_2)_2$—. In another aspect, X can be either another compound of Formula II, or selected from

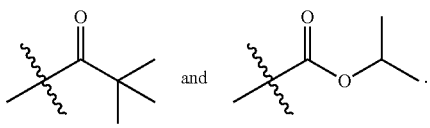

In yet another aspect, pharmaceutically acceptable salts of the compound are provided.

In accordance with a further aspect, the composition comprises one or more compounds comprising the structure of Formula II. In one aspect, $R^1$ can be selected from —$CH_2$—$CH_3$, —$(CH_2)_2$—$CH_3$, —CH(OH)—$CH_3$, and —$(CH_2)_2$—COOH; $R^2$ can be selected from —O—$CH_2$—$R^3$ and —O—$R^4$—O—X; $R^3$ can be selected from H or an optionally substituted $(C_1-C_{12})$alkyl; and $R^4$ can be selected from —$(CH_2)$—, —$(CH)_2$—, and —$(CH_2)_2$—O—$(CH_2)_2$—. In various aspects, X can be either another compound of Formula II, or selected from

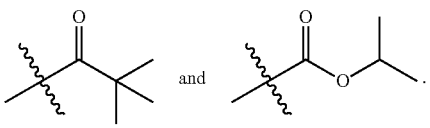

In yet other aspects, pharmaceutically acceptable salts of the compound are provided.

In accordance with a further aspect, in the topical probiotic composition above, the composition can comprises one or more compounds having a structure selected from:

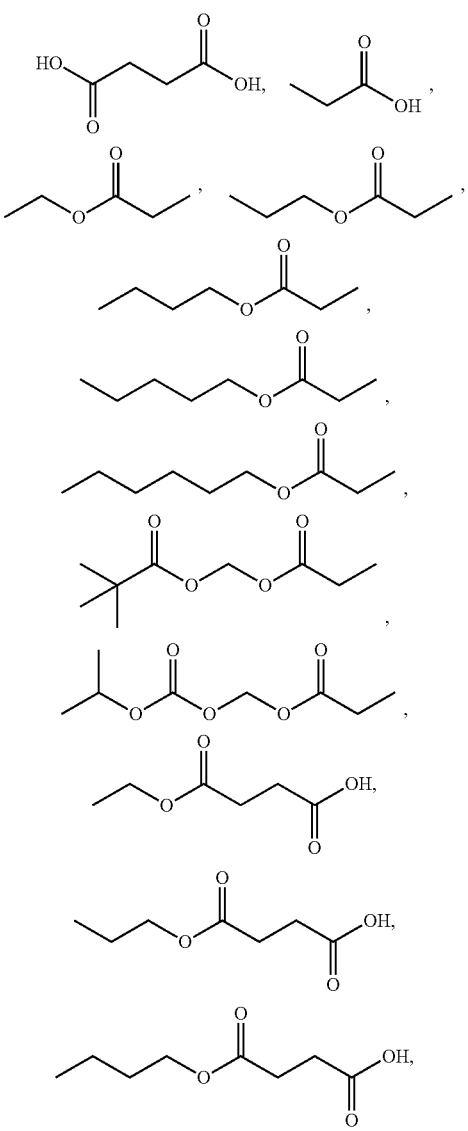

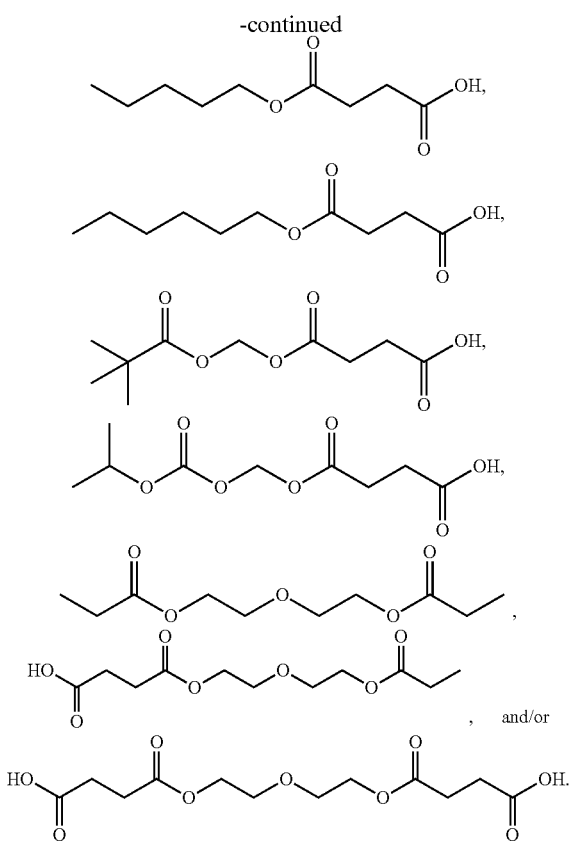

In various aspects, the composition can comprise a compound having the structure of:

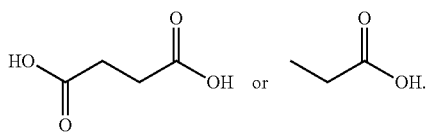

In yet other aspects, the composition can comprise a compound having the structure of:

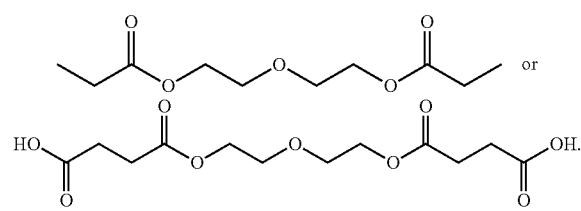

In yet other aspects, the composition can comprise at least one compound, and in certain aspects at least two compounds, selected from the group consisting of acetic acid, propionic acid, butyric acid, lactic acid, and succinic acid. The composition can further comprise at least one probiotic commensal skin bacteria, a probiotic commensal skin bacteria fermentation extract, and glycerol. The probiotic commensal skin bacteria can be selected from one of a *Propionibacterium* species, a *Paenibacillus* species, or a *Staphylococcus* species. In various aspects, the probiotic commensal skin bacteria can comprise a *Paenibacillus* species and a *Staphylococcus* species. In particular, the *Propionibacterium* species can include *P. acnes, P. granulosum, P. avidum*, and any combination thereof. In addition, the *Staphylococcus* species can be *S. epidermidis*.

In yet another embodiment, a topical probiotic composition is provided that comprises a plurality of probiotic commensal skin bacteria. The probiotic commensal skin bacteria can be one of a *Propionibacterium* species, a *Paenibacillus* species, and a *Staphylococcus* species. In various aspects, the probiotic commensal skin bacteria can comprise a *Paenibacillus* species and a *Staphylococcus* species. In particular, the *Propionibacterium* species can be selected from the group consisting of *P. acnes, P. granulosum, P. avidum*, and any combination thereof. In addition, the *Staphylococcus* species can be *S. epidermidis*. In yet other aspects, the composition lacks *P. acnes*.

In another embodiment, the topical probiotic composition comprises a probiotic commensal skin bacteria fermentation extract. In various aspects, the bacteria from which the extract is produced can include a *Propionibacterium* species, a *Paenibacillus* species, a *Staphylococcus* species, and any combination thereof. In particular, the *Propionibacterium* species can be selected from the group consisting of *P. acnes, P. granulosum, P. avidum*, and any combination thereof. In addition, the *Staphylococcus* species can be *S. epidermidis*.

In yet another embodiment, a topical probiotic composition is provided consisting essentially of a *P. acnes* fermentation extract, a *S. epidermidis* fermentation extract, or a *Paenibacillus* sp. fermentation extract.

In accordance with a further aspect, the compositions above can further comprise at least one compound, and in various aspects at least two compounds, selected from acetic acid, propionic acid, butyric acid, lactic acid, and succinic acid.

In accordance with a further aspect, the topical probiotic composition above can be formulated as a lotion, shake lotion, cream, ointment, gel, foam, powder, solid, paste or tincture.

In another embodiment, a fermentation extract is provided which can be obtained by fermenting *P. acnes* with glycerol under fermentation conditions. In various aspects, the fermentation extract can be used in inhibiting infection or overgrowth of *S. aureus*, methicillin-resistant *S. aureus* (MRSA), *Candida*, and *E. coli*.

In another embodiment, a fermentation extract is provided which can be obtained by fermenting *S. epidermidis* with glycerol under fermentation conditions. In yet another embodiment, a fermentation extract is provided which can be obtained by fermenting *Paenibacillus* sp. with glycerol under fermentation conditions. In various aspects, such fermentation extracts can be used for inhibiting infection or overgrowth of *P. acnes*.

In accordance with a further aspect, the fermentation extract can be formulated as a lotion, shake lotion, cream, ointment, gel, foam, powder, solid, paste or tincture.

In another embodiment, a bandage or dressing is provided comprising the topical probiotic compositions described above, a probiotic commensal skin bacteria fermentation extract described above, a probiotic commensal skin bacteria described above, glycerol, and any combination thereof. In various aspects, a bandage or dressing is provided the major constituents of which includes a matrix and a topical probiotic composition of Formulas I or II described above. In various aspects, a bandage or dressing is provided the major constituents of which includes a matrix and a probiotic commensal skin bacteria. In various aspects, a bandage or dressing is provided the major constituents of which includes a matrix and a probiotic commensal skin bacteria fermentation extract. In various aspects, a bandage or dressing is provided the major constituents of which includes a matrix and glycerol.

In another embodiment, a method is provided for treating or preventing a skin infection comprising contacting the skin with the topical probiotic compositions of Formula I described above. In various aspects, the skin infection can be caused by P. acnes.

In accordance with a further aspect, a method is provided for treating or preventing a skin infection comprising contacting the skin with the topical probiotic compositions of Formula II described above. In various aspects, the skin infection can be caused by at least one of S. aureus, methicillin-resistant S. aureus (MRSA), Candida, and E. coli.

In accordance with a further aspect, a method is provided for treating a skin infection comprising contacting the skin with one or more probiotic commensal skin bacteria alone or in combination with glycerol and/or a short chain fatty acid. In various aspects, the short chain fatty acid is the topical probiotic composition of Formula I. In various aspects, the skin infection can be caused by P. acnes.

In accordance with yet another aspect, the short chain fatty acid can be the topical probiotic composition of Formula II. In various aspects, the skin infection can be caused by at least one of S. aureus, methicillin-resistant S. aureus (MRSA), Candida, and E. coli.

In accordance with another aspect, a method is provided for treating an S. aureus or MRSA infection comprising contacting the skin with one or more probiotic commensal skin bacteria alone or in combination with glycerol and/or a short chain fatty acid. In various aspects, the short chain fatty acid can be the topical probiotic composition of Formula II.

In yet another aspect, a method is provided for inhibiting the growth or spread of S. aureus or MRSA comprising contacting a skin surface with one or more probiotic commensal skin bacteria alone or in combination with glycerol, a probiotic commensal skin bacteria fermentation extract, and/or a short chain fatty acid. In various aspects, the short chain fatty acid can be the topical probiotic composition of Formula II.

In another aspect, a method is provided for inhibiting or preventing the overgrowth of P. acnes comprising contacting a skin surface with a probiotic commensal skin bacteria alone or in combination with at least one of glycerol, a probiotic commensal skin bacteria fermentation extract, and a short chain fatty acid. In various aspects, the short chain fatty acid can be the topical probiotic composition of Formula I. In particular, the short chain fatty acid can include acetic acid, butyric acid, lactic acid, and succinic acid.

In various aspects, a method is provided for inhibiting the overgrowth of P. acnes comprising contacting the affected skin surface with a compound having the formula:

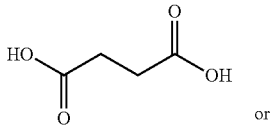

or

-continued

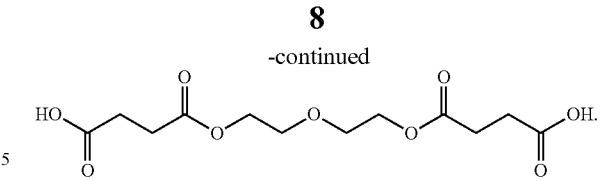

In yet other aspects, a method is provided for inhibiting or preventing the infection of S. aureus, methicillin-resistant S. aureus (MRSA), Candida species, or E. coli comprising contacting the affected skin surface with a compound having the formula:

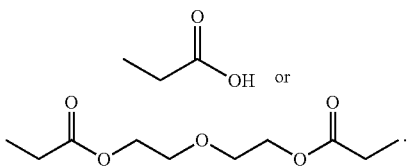

In another embodiment, a method is provided for preparing a topical probiotic composition by fermenting probiotic commensal skin bacteria in the presence of glycerol under fermentation conditions.

In yet another embodiment, a method is provided for identifying probiotic commensal skin bacteria comprising the acts of (a) identifying skin bacteria to target for inhibition; (b) incubating the target skin bacteria to provide a lawn; (c) obtaining from subject skin sample of commensal bacteria, preferably from a fingerprint or swab from a nose; (d) applying to sample to the lawn; (e) incubating the lawn and sample; and (f) identifying inhibition zones between the target skin bacteria and the sample, whereby the inhibition zones indicate the presence of probiotic commensal skin bacteria. The method can further include additional the acts of (g) fermenting the identified probiotic commensal skin bacteria under appropriate fermentation conditions; and (h) identifying compounds produced by the fermentation.

In yet another embodiment, a method is provided for producing microbiome balance on skin that reduces Th1 response in inflammation associated with P. acnes infection. In another embodiment, a method is provided for inhibiting production of Th1-associated cytokine production associated with P. acnes infection. In various aspects, the Th1-associated cytokine production is reduced by at least 50%.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 1A-C show inhibition studies of the growth of P. acnes by skin microorganisms. (A) A homogeneous lawn of microbes was created by pouring the skin microorganisms (H, arrow; $10^5$ CFU) that were pre-mixed with 1% agar with/without glycerol (+G/−G; 20 g/l) in TSB. P. acnes (P, arrow) with a serial dilution ($10^9$-$10^4$ CFU in 20 µl in PBS) were spotted on the top of microbial lawn for three days for CFU counts. (B) The serially diluted P. acnes was spotted on the regular plates (without pouring skin microorganisms) with/without glycerol. (C) A homogeneous lawn of S. epidermidis was created by pouring the S. epidermidis ATCC12228 (S, arrow; 105 CFU) that were pre-mixed with 1% agar in the absence or presence of glycerol (+G/−G; 20 g/l) in TSB. Nine separate drops of P. acnes (P, arrow; 5×106 CFU in 5 µl PBS) were placed on the top of a S. epidermidis lawn. A zone (dashed line) of inhibition between colonies of P. acnes and S. epidermidis was detected only in the presence of glycerol after three days of bacterial culture.

FIGS. 2A-F show skin fingerprint analysis of glycerol fermentation of skin microorganisms against P. acnes. The fingerprints of index, middle, and ring fingers were pressed onto the surface of rich medium agar plates in the absence (A) or presence (B) of 20 g/l glycerol at 30° C. under anaerobic conditions using Gas-Paks. P. acnes ($10^7$ CFU in 5 µl PBS) was spotted on the central portion of each fingerprint. Spotting P. acnes away from fingerprints served as controls (inserts). The high magnitude photos of (A) and (B) were displayed in (C, D) and (E, F), respectively. The inhibition zones (dash squares in E and F) were detected on the boundary between colonies of P. acnes and skin microorganisms. The bubble-like competed territories (open arrows) were found within P. acnes colonies. Two single colonies labeled 1 and 2 (solid arrows) were identified and assigned as S. epidermidis EHa-1 and Paenibacillus sp. EHa-1, respectively. Bars (A-B)=0.5 cm; (C—F)=0.1 cm. The antagonism (inhibition zones and bubble-like competed territories) between P. acnes and skin microorganisms were detected from 10 of 17 volunteers (11 males and 6 females). When fingerprints were pressed onto glycerol-free agar plates, no antagonism was found in all 17 volunteers.

FIGS. 10A-F show propionic acid alleviates lesions and suppresses bacterial colonization in the USA300-infected skins. A 5-mm long excision wounds were created on the back of ICR mice. To determine if the propionic acid itself affects the wound healing (A, B), 5 μl of propionic acid (100 mM), PBS (pH 7.1) or PBS/pH (pH 3.5) were applied topically to the wounded areas. (A) The lesion size ($mm^2$) was measured daily for 8 days after application of propionic acid, PBS/pH or PBS on day 0. (B) A picture of skin lesions on day 3 was presented. Bars=5 mm. To assess if propionic acid alleviates the lesions caused by USA300 infection (C, D), USA300 bacteria ($2 \times 10^6$ CFU) were applied onto the wounded areas 10 min after application of propionic acid (5 μl; 100 mM), PBS/pH 5 μl) or PBS (5 μl). (C) The lesion size was recorded daily for 8 days. (D) Skin lesions were pictured on day 3 after bacterial application. (E) Inflammation (arrows) surrounding the skin lesions (▼) was observed in the H&E-stained frozen sections [low (upper panels) and high (lower panels) powers] of skins applied with USA300 and controls. The scale bars of low power and high power were 40 μm, respectively. (F) Graphically depicts data from taking skin lesion homogenized in 200 μl of sterile PBS. Three days after bacterial application, the CFUs ($log_{10}$ CFU/ml) in the skin applied with USA300 or controls were enumerated by plating serial dilutions of the homogenate on a TBS agar plate. *P<0.05. P-values were evaluated using two-tailed t-tests. Data are the mean±SD of lesions from five mice per group.

FIG. 11A-F shows that fermented media of P. acnes and propionic acid suppress the infection of USA300 in mouse skin. (A) USA300 bacteria ($2 \times 10^6$ CFU) were applied onto the wounded areas 10 min after application of culture supernatants of P. acnes in the absence and presence of glycerol or a control (medium plus glycerol). The lesion size was recorded daily for 8 days. (B) Skin lesions pictured on day 1 after bacterial application were illustrated. Bar=1 cm. (C) Three days after bacterial application, the USA300 numbers in the skin were enumerated and presented as % of control. (D) For MBC assays, USA300 ($10^6$ CFU/ml) was incubated with propionic acid (5-100 mM in PBS) in media on a 96-well microplate overnight. Bacteria incubated with PBS alone served as a control. After incubation, USA300 was diluted $1:10-1:10^6$ with PBS, and 5 μl of the dilutions were spotted on an agar plate for CFU counts. P<0.01; *P<0.001 (two-tailed t-tests). Data are the mean±SD of three individual experiments. UD, undetectable. (E) USA300 bacteria ($2 \times 10^6$ CFU) were applied onto the wounded areas 10 min after application of propionic acid (5 μl; 100 mM) or PBS (5 μl). The lesion size was measured daily for 8 days and recorded. *P<0.05; P<0.01; *P<0.001 (A, E). (F) Three days after bacterial application, the USA300 numbers in the skin were counted and presented as % of PBS control. P<0.01; *P<0.001 (C, F). P-values were evaluated using two-tailed t-tests. Data are the mean±SD of lesions from three separate experiments performed with five mice per group. NS: Non-significant.

FIGS. 13A-D show that glycerol fermentation of P. acnes in skin wounds diminishes the colonization of USA300. P. acnes ($10^7$ CFU in 5 μl PBS), P. acnes and glycerol (0.2 mg), PBS (5 μl) alone or glycerol alone were applied onto the skin wounds for 3 days before administration of USA300 ($10^7$ CFU in 5 μl PBS) onto the wounded areas. (A, B) Skin lesions pictured 3 days after USA300 application were illustrated. Bar=0.5 cm. (C) The USA300 numbers in the skin wounds were enumerated 3 days after USA300 application and presented as % of those in skin applied with P. acnes (C) or PBS (D). *P<0.05. P-values were evaluated using two-tailed t-tests. Data are the mean±SD of lesions from five mice per group. NS: Non-significant.

FIGS. 14A-C show validation of P. acnes glycerol fermentation via identification of SCFAs in the fermented media by NMR analysis. Fermented media of P. acnes were centrifuged and passed through a 0.2 μm filter. Supernatants were then mixed with 10% $D_2O$ and analyzed by NMR spectrometers. Representative 1-D $^{13}C$-(A) and 1H-(B) NMR spectra (400 MHz JEOL JNM-ECS) that reveal the principal SCFAs in the fermented media seventeen days after addition of $^{13}C_3$-glycerol. (C) A 2-D $^1H$-$^{13}C$ HSQC NMR spectrum (600 MHz) was displayed. In addition to glycerol (Gly), three SCFAs [acetic acid (Ac), lactic acid (L), and propionic acid (P)] were detected in the fermentation products of P. acnes.

FIGS. 18A-B show (A) Minimal fungicidal concentration of propionic acid against *Candida albicans* and (B) minimal bactericidal concentration against *Escherichia coli*. ND=not detectable; PBS=phosphate buffered saline. Data are the mean±standard deviation of three individual experiments. $P<0.01$; *$P<0.001$.

FIG. 19 shows minimal bactericidal concentration of propionic acid against *Propionibacterium acnes*. ND=not detectable; PBS=phosphate buffered saline. Data are the mean±standard deviation of three individual experiments. ***$P<0.001$.

FIGS. 20A-D show (A) Chemical structure of propionic acid 2-(2-propionyloxyethoxy)ethyl ester (PA-DEG-PA) composed of two propionic acid moieties and (B) esterified to a DEG linker; (C) and (D) minimum bactericidal concentration of PA-DEG-PA and propionic acid against *Staphylococcus aureus* USA300. ND=undetectable; C=control (4% dimethyl sufoxide). Data are the mean±standard deviation of three individual experiments. *$P<0.05$; **$P<0.01$.

DETAILED DESCRIPTION

Figure 1A:
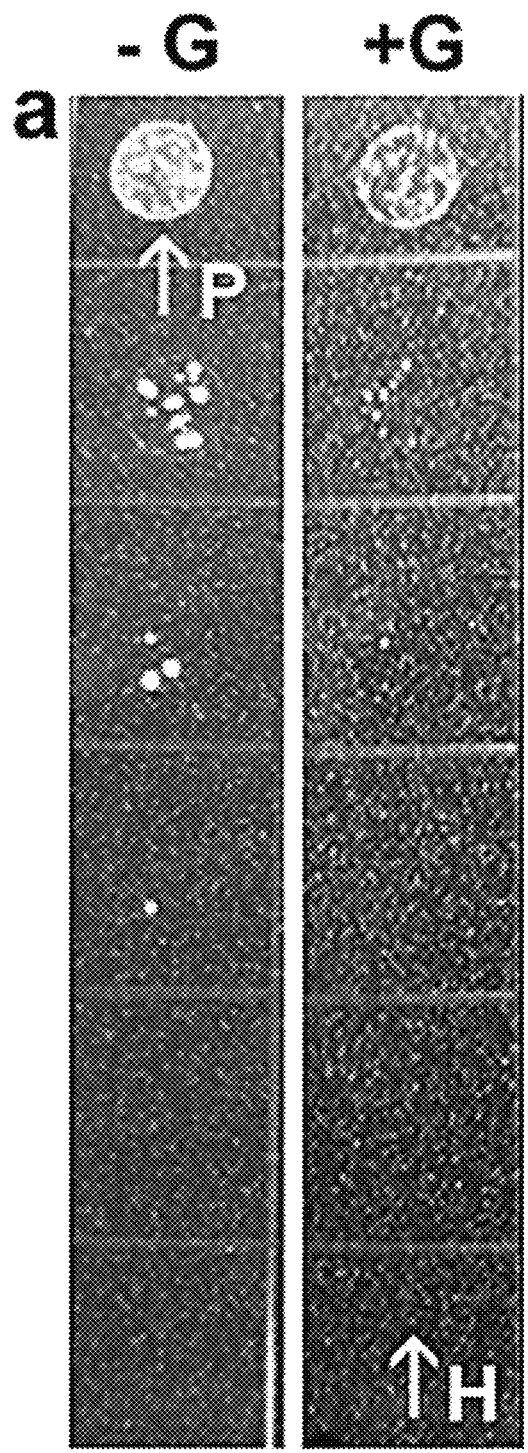

As used herein and in the appended claims, the singular forms "a," "and," and "the" include plural referents unless the context clearly dictates otherwise. Thus, for example, reference to "an agent" includes a plurality of such agents and reference to "the microorganism" includes reference to one or more microorganisms and equivalents thereof known to those skilled in the art, and so forth.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Unless defined otherwise, all technical and scientific terms used herein have the same meaning as commonly understood to one of ordinary skill in the art to which this disclosure belongs. Any methods and reagents similar or equivalent to those described herein can be used in the practice of the disclosed methods and compositions.

As used herein, the term "Probiotic Composition" includes a composition, which may include compounds described as Formula I and Formula II below, as well as a probiotic commensal skin bacteria, a probiotic commensal skin bacteria fermentation extract, glycerol, and any combination thereof, that affects the microbiome balance of the human skin. Methods of identifying the skin bacteria are provided herein. Methods of producing the fermentation extract are also provided herein. Diseases and disorders of the human skin that are affected by the microbiome balance are also provided herein.

As used herein, the term "Topical" can include administration to the skin externally, as well as shallow injection (e.g., intradermally and intralesionally as described in the Examples) such that a topical probiotic composition described herein comes in direct contact with skin infected with a commensal bacteria (e.g., lesions).

As used herein, the term "Fermentation Extract" means a product of fermenting a probiotic commensal skin bacteria in a food source, in particular glycerol, under appropriate fermentation conditions. Examples of such fermentation conditions are provided herein.

As used herein, the term "Probiotic Commensal Skin Bacteria" includes a microorganism of the skin microbiome which, the growth of which can be modulated using the methods described herein. Such skin bacteria include, but are not limited to, *Propionibacterium* species, a *Paenibacillus* species, a *Staphylococcus* species, and any combination thereof. Further, *Propionibacterium* species includes, but is not limited to, *P. acnes, P. granulosum, P. avidum*, and any combinations thereof. *Staphylococcus* species includes *S. epidermidis*.

The term "contacting" refers to exposing the pathogenic bacterium to the topical probiotic composition such that the probiotic skin composition can inhibit, kill, or lyse the pathogenic bacteria.

The terms "inhibiting" or "inhibiting effective amount" refers to the amount of probiotic skin composition consisting of one or more probiotic microorganism and/or fermented medium or extract and/or fermentation by-products and/or synthetic molecules that is sufficient to cause, for example, a bacteriostatic or bactericidal effect. The term "inhibiting" also includes preventing or ameliorating a sign or symptoms of a disorder (e.g., a rash, sore, and the like). Bacteria that can be affected by the peptides of the disclosure include both gram-negative and gram-positive bacteria and other microorganisms.

The term "therapeutically effective amount" as used herein for treatment of a subject afflicted with a disease or disorder means an amount of a probiotic skin composition or extract thereof sufficient to ameliorate a sign or symptom of the disease or disorder. For example, a therapeutically effective amount can be measured as the amount sufficient to decrease a subject's symptoms of dermatitis, acne vulgaris or rash by measuring the frequency of severity of skin sores. Typically, the subject is treated with an amount to reduce a symptom of a disease or disorder by at least 50%, 90% or 100%. Generally, the optimal dosage of the polypeptide or peptide will depend upon the disorder and factors such as the weight of the subject, the type of bacteria, virus or fungal infection, the sex of the subject, and degree of symptoms. Nonetheless, suitable dosages can readily be determined by one skilled in the art.

The term "purified" and "substantially purified" as used herein refers to cultures, or co-cultures of microorganisms or of biological agent (e.g. fermentation media and extracts, fractionated fermentation media, fermentation by-products, propionic acid, succinic acid etc.) that is substantially free of other cells or components found in the natural environment with which an in vivo-produced agent would naturally be associated. In some embodiments, a co-culture probiotic can comprise a plurality of commensal skin bacteria.

The disclosure provides topical probiotic compositions for producing or maintaining skin microbiome balance to treat or prevent certain diseases or disorders of the skin, particularly human skin. As provided in the Examples below, fermentation of glycerol with *Staphylococcus epidermidis* (*S. epidermidis*), a human skin commensal bacterium, and *Paenibacillus* species can function as skin probiotics for suppression of the growth of *Propionibacterium acnes* (*P. acnes*), a bacterium that is associated with acne vulgaris. In addition, as provided in the Examples below,

*Propionibacterium acnes* (*P. acnes*), a human skin commensal bacterium, can function as a skin probiotic for suppression of the growth of USA300, a community-acquired methicillin-resistant *Staphylococcus aureus* (MRSA), *S. aureus*, *Candida albicans* (*C. albicans*), and *Escherichia coli* (*E. coli*).

The Examples below also provide that fermented media and succinic acid, one of four short-chain fatty acids (SCFAs) detected in the *S. epidermidis* fermented media by nuclear magnetic resonance (NMR) analysis, effectively inhibit the growth of *P. acnes* in vitro and in vivo. Both intralesional injection and topical application of succinic acid to *P. acnes*-induced lesions markedly suppress the *P. acnes* overgrowth in mice, and associated acne vulgaris.

The Examples below also provide that other bacterial members in the skin microbiome can undergo fermentation to rein in the overgrowth of *P. acnes*. Fermented media from *P. acne* fermentation with glycerol, propionic acid and propionic acid derivatives effectively inhibit *S. aureus*, *Candida*, and *E. coli* in vitro and in vivo. The concept of interference between skin commensals and *P. acnes*, *S. aureus*, *Candida*, and *E. coli* via fermentation can be applied to develop probiotics against acne vulgaris and other skin diseases and open up an entirely new area of studying the biological function of skin microbiome in promoting human health.

Here, novel skin probiotics derived from fermentation of human skin commensal bacteria are introduced. The use of these probiotics for promoting skin health will open a new skin-care industry and development of new therapeutic and preventative treatments for the treatment and prevention of various skin infections, skin diseases and skin disorders.

The topical probiotic composition of the disclosure can be used to treat infections, diseases and disorders, improve healing and reduce morbidity associated with skin damage and infection. For example, the topical probiotic compositions can be used to treat a skin infection by contacting the skin with a therapeutically effective amount or inhibitive effective amount of a composition as described below. In one embodiment, the skin infection is caused by *P. acnes*, *Staphylococcus aureus*, *Candida albicans*, or *Escherichia coli*.

The disclosure also provides a method for inhibiting the growth of a pathogenic bacterium by contacting the pathogenic bacterium with one or more SCFA or formulation of one or more probiotic commensal skin bacteria, probiotic commensal skin bacteria fermentation extracts, glycerol, combinations thereof, or fermentation by-products found in such extracts of the disclosure.

Contacting of an organism with a topical probiotic composition of the disclosure can occur in vitro, for example, by adding the topical probiotic composition to a bacterial culture to test for susceptibility of the bacteria. Alternatively, contacting can occur in vivo, for example by contacting the topical probiotic composition with a subject afflicted with a bacterial infection or subject susceptible to infection.

Figure 11E:
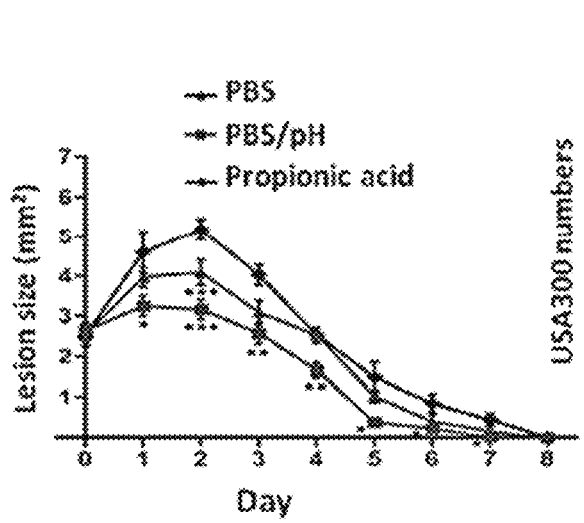

The Examples below also provide a novel mechanism by which the skin commensal microorganism, *Staphylococcus epidermidis* (*S. epidermidis*), makes use of fermentative processes to hinder the growth of *P. acnes* in the skin that is associated with acne lesions and reduce inflammation associated with acne. The Examples below also provide a novel mechanism by which the skin commensal microorganism, *P. acnes*, makes use of fermentative processes to hinder the colonization of CA-MRSA in skin wounds. *P. acnes* ferments glycerol to various SCFAs including propionic acid (FIG. 12). As shown in FIG. 11, propionic acid (25 mM) exerted excellent antimicrobial activity against USA300, but did not affect the growth of *P. acnes*. Thus, *P. acnes* fermentation has a low risk of disrupting the balance of skin microbiome. Propionic acid can inhibit various strains (e.g., ATCC29247 and CMCC(B)26003) of *S. aureus* besides USA300, suggesting broad spectrum anti-*S. aureus* activity of propionic acid.

The identified $^{13}$C-labeled SCFAs in FIG. 12 were not directly derived from $^{13}C_3$-glycerol metabolism by mouse skin cells since no $^{13}$C-labeled SCFAs were detected in mice injected with $^{13}C_3$-glycerol plus PBS. Furthermore, the presence of $^{13}$C-labeled propionic acid in the mice injected with $^{13}C_3$-glycerol plus *P. acnes* validated that the identified $^{13}$C-labeled SCFAs resulted from the *P. acnes* fermentation. The SCFA profile of $^{13}C_3$-glycerol fermentation by *P. acnes* in vivo (FIG. 12) was similar to that in vitro (FIG. 14).

Propionic acid was measureable in the products of both in vivo and in vitro glycerol fermentation. Ethanol, butyric acid and 3-hydroxy-butyric acid were detected when $^{13}C_3$-glycerol plus *P. acnes* were injected into mice. The disclosure also provides methods for buffering of extracts or synthetic preparation of SCFAs that may be useful to prevent skin irritation due to acidity while maintaining the desired antimicrobial and anti-inflammatory activity.

The disclosure also provides methods and compositions of anti-*S. aureus* skin probiotics containing live *P. acnes*, glycerol and/or SCFAs. The disclosure also provides bacterial-free fermented media or a fermentation inducer (e.g., glycerol) as another approach.

Any of a variety of methods known in the art can be used to administer a topical probiotic compositions to a subject. For example, a probiotic skin composition or extract or synthetic preparation of the disclosure may be formulated for topical administration (e.g., as a lotion, cream, spray, gel, or ointment). Such topical formulations are useful in treating or inhibiting microbial, fungal, viral presence or infections or inflammation on the skin. Examples of formulations include topical lotions, creams, soaps, wipes, and the like.

The Examples below also describe a method for inhibiting a topical bacterial, viral and/or fungal-associated disorders by contacting or administering a therapeutically effective amount of a topical probiotic compositions to a subject who has, or is at risk of having, such a disorder.

The topical probiotic compositions are also useful as antimicrobials suitable for tackling the growing problem of antibiotic-resistant bacteria strains, and for treating and/or preventing outbreaks of infectious diseases or preventing skin diseases and skin disorders.

Accordingly, in one embodiment, a topical probiotic composition is provided that is capable of producing or maintaining skin microbiome balance. The composition can comprise a therapeutically effective amount or inhibiting effective amount of one or more microbiome balancing compounds. The compounds can have the structure of Formula I:

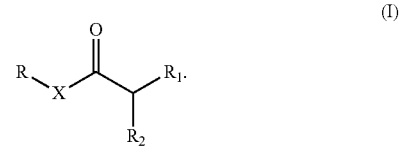

(I)

In various aspects, X can be selected from —O—, —S—, and —NH—; R, $R_1$, and $R_2$ can be independently selected from the group consisting of hydrogen, and optionally substituted ($C_1$-$C_{12}$)alkyl, optionally substituted hetero-($C_1$-$C_{12}$) alkyl, optionally substituted ($C_1$-$C_{12}$) alkenyl, optionally substituted hetero-($C_1$-$C_{12}$) alkenyl, optionally substituted ($C_1$-$C_{12}$)alkynyl, optionally substituted hetero-($C_1$-$C_{12}$) alkynyl, optionally substituted ($C_1$-$C_{12}$) cycloalkyl, optionally substituted ($C_1$-$C_{12}$)cycloalkenyl, optionally substituted aryl, optionally substituted heterocycle, and optionally substituted mixed ring system, and —O—$R_3$—O—Y; $R_3$ can be selected from the group consisting of an optionally substituted ($C_1$-$C_{12}$)alkyl, optionally substituted hetero-($C_1$-$C_{12}$)alkyl, optionally substituted ($C_1$-$C_{12}$)alkenyl, optionally substituted hetero-($C_1$-$C_{12}$)alkenyl, optionally substituted ($C_1$-$C_{12}$)alkynyl, and optionally substituted hetero-($C_1$-$C_{12}$) alkynyl; and Y can be another compound of Formula I, or can be selected from the group consisting of

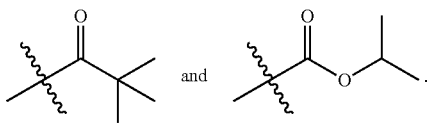

In another aspect, pharmaceutically acceptable salts of the compound are provided.

By including the ester above, a "pro-drug" can be formed such that an inactive compound may be administered to the skin, and esterases present on the skin cleave the ester bond to release active compounds. Synthesis of such ester pro-drugs is provided in the Examples below.

In yet another aspect, the optional substituent can be independently selected from the group consisting of carboxyl, nitro, halogen, amino, hydroxyl, cyano, methoxy, polyalkylene glycol, and phenyl, further wherein the phenyl group may be optionally substituted with one or more substituents selected from the group consisting of carboxyl, nitro, halogen, amino, hydroxyl, cyano, methoxy, and polyalkylene glycol.

In another embodiment, the composition can comprise a therapeutically effective amount or inhibiting effective amount of one or more compounds having the structure of Formula II:

(II)

In one aspect, $R^1$ can be selected from an optionally substituted ($C_1$-$C_6$)alkyl; $R^2$ can be selected from a hydroxyl, —O—$CH_2$—$R^3$, and —O—$R^4$—O—X; $R^3$ can be selected from H, optionally substituted ($C_1$-$C_{12}$) alkyl, optionally substituted hetero-($C_1$-$C_{12}$) alkyl, optionally substituted ($C_1$-$C_{12}$)alkenyl, optionally substituted hetero-($C_1$-$C_{12}$)alkenyl, optionally substituted ($C_1$-$C_{12}$)alkynyl, optionally substituted hetero-($C_1$-$C_{12}$)alkynyl, optionally substituted ($C_1$-$C_{12}$) cycloalkyl, optionally substituted ($C_1$-$C_{12}$) cycloalkenyl, optionally substituted aryl, optionally substituted heterocycle, and optionally substituted mixed ring system; and $R^4$ can be selected from the group consisting of an optionally substituted ($C_1$-$C_{12}$) alkyl, optionally substituted hetero-($C_1$-$C_{12}$) alkyl, optionally substituted ($C_1$-$C_{12}$) alkenyl, optionally substituted hetero-($C_1$-$C_2$) alkenyl, optionally substituted ($C_1$-$C_{12}$) alkynyl, and optionally substituted hetero-($C_1$-$C_{12}$)alkynyl. In another aspect, X can be either another compound of Formula II, or selected from the group consisting of

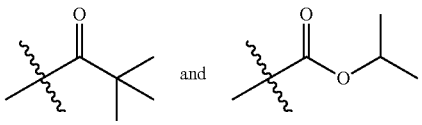

wherein, when $R^2$ is a hydroxyl then the pharmaceutical composition comprises at least two compounds comprising the structure of Formula II. In yet another aspect, pharmaceutically acceptable salts of the compounds are provided.

In accordance with a further aspect, the composition comprises one or more compounds comprising the structure of Formula II. In various aspects, $R^1$ can be selected from an optionally substituted ($C_1$-$C_6$)alkyl; $R^2$ can be selected from a hydroxyl, —O—$CH_2$—$R^3$, and —O—$R^4$—O—X; $R^3$ can be selected from H or an optionally substituted ($C_1$-$C_{12}$) alkyl; $R^4$ can be selected from an optionally substituted ($C_1$-$C_{12}$)alkyl or an optionally substituted hetero-($C_1$-$C_{12}$) alkyl; and X can be either another compound of Formula II, or selected from

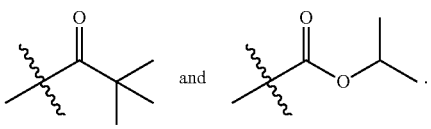

In another aspect, pharmaceutically acceptable salts of the compound are provided.

In accordance with a further aspect, the composition comprises two or more compounds comprising the structure of Formula II. In various aspects, $R^1$ can be selected from an optionally substituted ($C_1$-$C_6$)alkyl; and $R^2$ can be a hydroxyl. In another aspect, pharmaceutically acceptable salts of the compound are provided.

In accordance with a further aspect, the composition comprises one or more compounds comprising the structure of Formula II. In various aspects, $R^1$ can be selected from an optionally substituted ($C_1$-$C_6$)alkyl; $R^2$ can be selected from —O—$CH_2$—$R^3$ and —O—$R^4$—O—X; $R^3$ can be selected from H or an optionally substituted ($C_1$-$C_{12}$)alkyl; and $R^4$ can be selected from —($CH_2$)—, —($CH$)$_2$—, and —($CH_2$)$_2$—O—($CH_2$)$_2$—. In another aspect, X can be either another compound of Formula II, or selected from

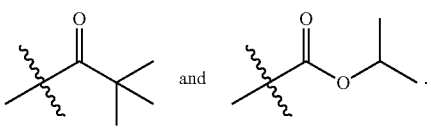

In yet another aspect, pharmaceutically acceptable salts of the compound are provided.

In accordance with a further aspect, the composition comprises one or more compounds comprising the structure of Formula II. In one aspect, $R^1$ can be selected from —$CH_2$—$CH_3$, —($CH_2$)$_2$—$CH_3$, —$CH(OH)$—$CH_3$, and —($CH_2$)$_2$—COOH; $R^2$ can be selected from —O—$CH_2$—$R^3$ and —O—$R^4$—O—X; $R^3$ can be selected from H or an optionally substituted ($C_1$-$C_{12}$)alkyl; and $R^4$ can be selected from —(CH$_2$)—, —(CH$_2$)$_2$—, and —(CH$_2$)$_2$—O—(CH$_2$)$_2$—. In various aspects, X can be either another compound of Formula II, or selected from

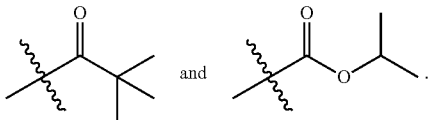

In yet other aspects, pharmaceutically acceptable salts of the compound are provided.

In accordance with a further aspect, in the topical probiotic composition above, the composition can comprises one or more compounds having a structure selected from:

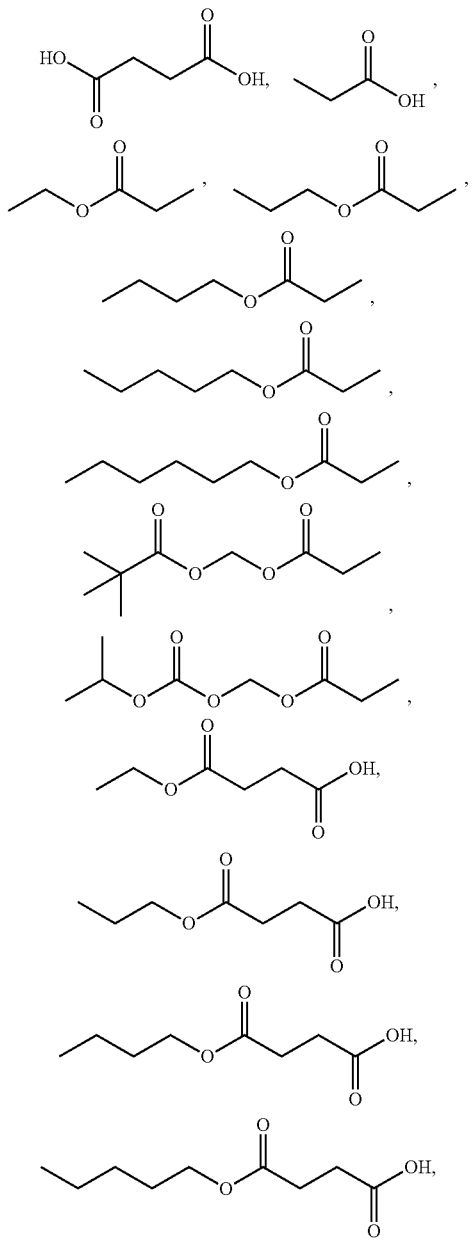

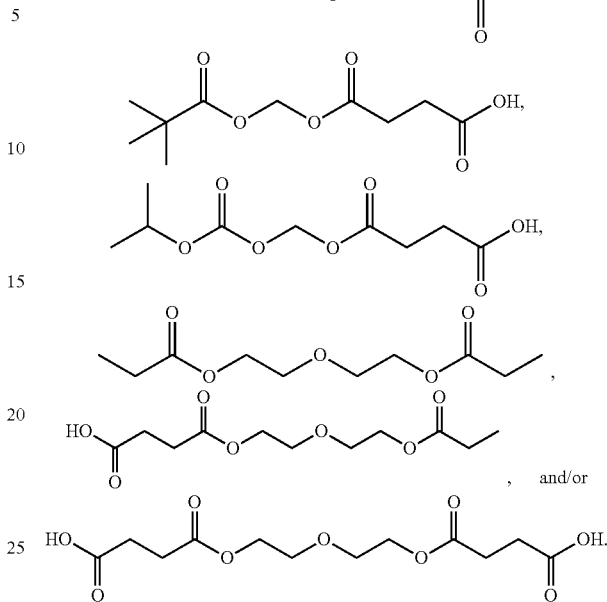

In various aspects, the composition can comprise a compound having the structure of:

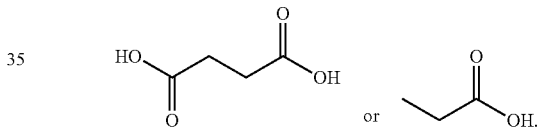

In yet other aspects, the composition can comprise a compound having the structure of:

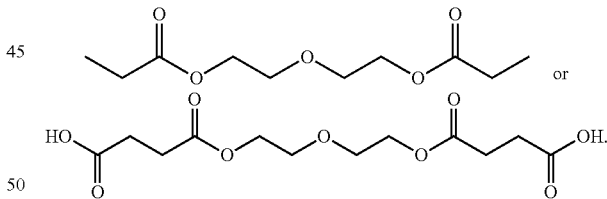

In yet other aspects, the composition can comprise at least one compound, and in certain aspects at least two compounds, selected from the group consisting of acetic acid, propionic acid, butyric acid, lactic acid, and succinic acid. The composition can further comprise at least one probiotic commensal skin bacteria, a probiotic commensal skin bacteria fermentation extract, and glycerol. The probiotic commensal skin bacteria can be selected from one of a *Propionibacterium* species, a *Paenibacillus* species, or a *Staphylococcus* species. In various aspects, the probiotic commensal skin bacteria can comprise a *Paenibacillus* species and a *Staphylococcus* species. In particular, the *Propionibacterium* species can include *P. acnes, P. granulosum, P. avidum*, and any combination thereof. In addition, the *Staphylococcus* species can be *S. epidermidis*.

In yet another embodiment, a topical probiotic composition is provided that comprises a plurality of probiotic commensal skin bacteria. The probiotic commensal skin bacteria can be one of a *Propionibacterium* species, a *Paenibacillus* species, a *Staphylococcus* species. In various aspects, the probiotic commensal skin bacteria can comprise a *Paenibacillus* species and a *Staphylococcus* species. In particular, the *Propionibacterium* species can be selected from the group consisting of *P. acnes, P. granulosum, P. avidum*, and any combination thereof. In addition, the *Staphylococcus* species can be *S. epidermidis*. In yet other aspects, the composition lacks *P. acnes*.

In another embodiment, the topical probiotic composition comprises a probiotic commensal skin bacteria fermentation extract. In various aspects, the bacteria from which the extract is produced can include a *Propionibacterium* species, a *Paenibacillus* species, a *Staphylococcus* species, and any combination thereof. In particular, the *Propionibacterium* species can be selected from the group consisting of *P. acnes, P. granulosum, P. avidum*, and any combination thereof. In addition, the *Staphylococcus* species can be *S. epidermidis*.

In yet another embodiment, a topical probiotic composition is provided consisting essentially of a *P. acnes* fermentation extract, a *S. epidermidis* fermentation extract, or a *Paenibacillus* sp. fermentation extract.

In accordance with a further aspect, the compositions above can further comprise at least one compound, and in various aspects at least two compounds, selected from acetic acid, propionic acid, butyric acid, lactic acid, and succinic acid.

In accordance with a further aspect, the topical probiotic composition above can be formulated as a lotion, shake lotion, cream, ointment, gel, foam, powder, solid, paste or tincture.

In another embodiment, a fermentation extract is provided which can be obtained by fermenting *P. acnes* with glycerol under fermentation conditions. In various aspects, the fermentation extract can be used in inhibiting infection or overgrowth of *S. aureus*, methicillin-resistant *S. aureus* (MRSA), *Candida*, and *E. coli*.

In another embodiment, a fermentation extract is provided which can be obtained by fermenting *S. epidermidis* with glycerol under fermentation conditions. In yet another embodiment, a fermentation extract is provided which can be obtained by fermenting *Paenibacillus* sp. with glycerol under fermentation conditions. In various aspects, such fermentation extracts can be used for inhibiting infection or overgrowth of *P. acnes*.

In accordance with a further aspect, the fermentation extract can be formulated as a lotion, shake lotion, cream, ointment, gel, foam, powder, solid, paste or tincture.

In another embodiment, a bandage or dressing is provided comprising the topical probiotic compositions described above, a probiotic commensal skin bacteria fermentation extract described above, a probiotic commensal skin bacteria described above, glycerol, and any combination thereof. In various aspects, a bandage or dressing is provided the major constituents of which includes a matrix and a topical probiotic composition of Formulas I or II described above. In various aspects, a bandage or dressing is provided the major constituents of which includes a matrix and a probiotic commensal skin bacteria. In various aspects, a bandage or dressing is provided the major constituents of which includes a matrix and a probiotic commensal skin bacteria fermentation extract. In various aspects, a bandage or dressing is provided the major constituents of which includes a matrix and glycerol.

In another embodiment, a method is provided for treating or preventing a skin infection comprising contacting the skin with the topical probiotic compositions of Formula I described above. In various aspects, the skin infection can be caused by *P. acnes*.

In accordance with a further aspect, a method is provided for treating or preventing a skin infection comprising contacting the skin with the topical probiotic compositions of Formula II described above. In various aspects, the skin infection can be caused by at least one of *S. aureus*, methicillin-resistant *S. aureus* (MRSA), *Candida*, and *E. coli*.

In accordance with a further aspect, a method is provided for treating a skin infection comprising contacting the skin with one or more probiotic commensal skin bacteria alone or in combination with glycerol and/or a short chain fatty acid. In various aspects, the short chain fatty acid is the topical probiotic composition of Formula I. In various aspects, the skin infection can be caused by *P. acnes*.

In accordance with yet another aspect, the short chain fatty acid can be the topical probiotic composition of Formula II. In various aspects, the skin infection can be caused by at least one of *S. aureus*, methicillin-resistant *S. aureus* (MRSA), *Candida*, and *E. coli*.

In accordance with another aspect, a method is provided for treating an *S. aureus* or MRSA infection comprising contacting the skin with one or more probiotic commensal skin bacteria alone or in combination with glycerol and/or a short chain fatty acid. In various aspects, the short chain fatty acid can be the topical probiotic composition of Formula II.

In yet another aspect, a method is provided for inhibiting the growth or spread of *S. aureus* or MRSA comprising contacting a skin surface with one or more probiotic commensal skin bacteria alone or in combination with glycerol, a probiotic commensal skin bacteria fermentation extract, and/or a short chain fatty acid. In various aspects, the short chain fatty acid can be the topical probiotic composition of Formula II.

In another aspect, a method is provided for inhibiting or preventing the overgrowth of *P. acnes* comprising contacting a skin surface with a probiotic commensal skin bacteria alone or in combination with at least one of glycerol, a probiotic commensal skin bacteria fermentation extract, and a short chain fatty acid. In various aspects, the short chain fatty acid can be the topical probiotic composition of Formula I. In particular, the short chain fatty acid can include acetic acid, butyric acid, lactic acid, and succinic acid.

In various aspects, a method is provided for inhibiting the overgrowth of *P. acnes* comprising contacting the affected skin surface with a compound having the formula:

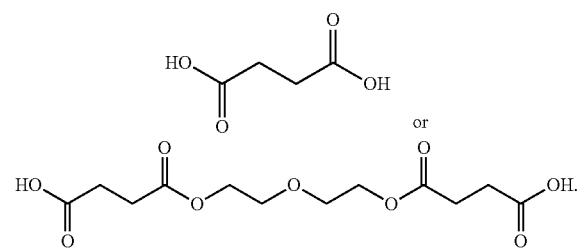

In yet other aspects, a method is provided for inhibiting or preventing the infection of *S. aureus*, methicillin-resistant *S. aureus* (MRSA), *Candida* species, or *E. coli* comprising contacting the affected skin surface with a compound having the formula:

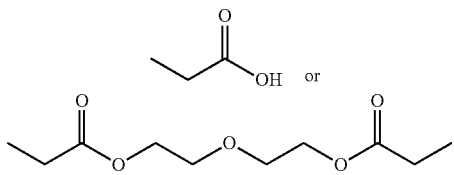

In another embodiment, a method is provided for preparing a topical probiotic composition by fermenting probiotic commensal skin bacteria in the presence of glycerol under fermentation conditions.

In yet another embodiment, a method is provided for identifying probiotic commensal skin bacteria comprising the acts of (a) identifying skin bacteria to target for inhibition; (b) incubating the target skin bacteria to provide a lawn; (c) obtaining from subject skin sample of commensal bacteria, preferably from a fingerprint or swab from a nose; (d) applying to sample to the lawn; (e) incubating the lawn and sample; and (f) identifying inhibition zones between the target skin bacteria and the sample, whereby the inhibition zones indicate the presence of probiotic commensal skin bacteria. The method can further include additional the acts of (g) fermenting the identified probiotic commensal skin bacteria under appropriate fermentation conditions; and (h) identifying compounds produced by the fermentation.

In yet another embodiment, a method is provided for producing microbiome balance on skin that reduces Th1 response in inflammation associated with *P. acnes* infection. In another embodiment, a method is provided for inhibiting production of Th1-associated cytokine production associated with *P. acnes* infection. In various aspects, the Th1-associated cytokine production is reduced by at least 50%.

The following examples are intended to illustrate but not limit the disclosure. While they are typical of those that might be used, other procedures known to those skilled in the art may alternatively be used.

EXAMPLES

The human body is home to ten times more bacteria than it is human cells. The skin is the human body's largest organ, colonized by a diverse milieu of microorganisms (skin microbiome), most of which are commensals since they reside on and in the skin and are harmless or even beneficial to their host. *Propionibacterium acnes* (*P. acnes*), a skin commensal bacterium, gets its name from its ability to produce propionic acid, a short-chain fatty acid (SCFA), during fermentation.

A number of SCFAs, although concentrations are relatively low, are naturally produced by commensal bacteria. A few SCFAs have been approved by the United States Environmental Protection Agency (EPA) as active ingredients for use as fungicides and bactericides on stored grains, poultry litter, and drinking water for poultry and livestock (Sebastian et al., Comparative assessment of bacterial inoculation and propionic acid treatment of aerobic stability and microbial populations of ensiled high-moisture ear corn. Journal of Animal Science (1996) 74:447-456. However, appropriate formulations of skin commensal bacteria or SCFAs derived from skin bacteria have not been identified for use in the treatment or prevention skin infections such as those caused by various bacteria including MRSA, fungi, or viruses. Succinic acid ($C_4H_6O_4$) has been approved by the Food and Drug Administration (FDA) for use as an inactive excipient to control pH in injectable and oral pharmaceutical products, food and beverages. The succinic acid has not been previously identified as having antibacterial properties or any utility for use in the treatment and prevention skin infections including skin lesions caused by *P. acnes*, skin diseases, and skin disorders including acne vulgaris or for the treatment and prevention of inflammation associated with acne or any other skin disease or skin disorder.

Commensal bacteria and short chain fatty acids (SCFAs) in skin play a role in influencing the predominant residence of bacteria on normal human skin (See Ushijima et al., Acetic, propionic, and oleic acid as the possible factors influencing the predominant residence of some species of *Propionibacterium* and coagulasenegative *Staphylococcus* on normal human skin. Canadian Journal of Microbiology (1984) 30:647-652). The data presented herein demonstrates that fermentation by *P. acnes* does not significantly disrupt the growth of skin microorganism, but does have antimicrobial activity against other microorganism including *E. coli*, *C. albicans* and *S. aureus* and fermentation by *S. epidermidis* or *Paenibacillus* sp. has antimicrobial activity against *P. acnes*.

The role of skin commensal bacteria in skin disease and in maintaining skin health has not been previously known. The experiments performed in this disclosed invention demonstrated that commensal microbes in human skin have a fermentation activity and that ferments including SCFAs of these microbes have probiotic activities to maintain the homeostasis of the skin microbiome, prevent disease and promote skin health. An acne lesion, particularly a closed comedone or deep-seated abscess in an open comedone, creates an anaerobic microenvironment which facilitates overgrowth of *Propionibacterium acnes* (*P. acnes*). *P. acnes*, *Staphylococcus epidermidis* (*S. epidermidis*), and other skin microflora co-exist in acne lesions (Nishijima et al., 2000). This disclosed invention demonstrated that anaerobic acne microenvironment triggers human skin microflora to undergo fermentation, and this skin microflora utilizes fermentation to rein in the overgrowth of *P. acnes* within acne lesions.

Acne vulgaris is an inflammatory skin disease associated with the overgrowth of *P. acnes*. Around 40 to 50 million Americans suffer from acne vulgaris each year. Many antibiotics have been used for treatments of acne vulgaris, but these antibiotics are non-specific and have a risk of creating antibiotic-resistant bacteria (Haider et al., 2004). The oxidizing agent benzoyl peroxide (BPO) has been one of the most frequently used topical medications for acne treatment. Isotretinoin is a powerful and effective medication derived from vitamin A (Layton et al., 2006). However, it is strictly regulated due to the induction of serious side effects. Intralesional corticosteroid injection is an important adjunct in the treatment of painful nodulocystic acne lesions. However, the injection can cause local side effects including linear hypopigmentation and atrophy (Levine et al., 1983). None of the treatments above use endogenous molecules which may have a lower risk of developing side-effects and resistant microbes.

The experiments performed that lead to this disclosed invention examined acne probiotics (topical probiotic compositions) which include (1) novel short chain fatty acids (SCFAs) with anti-*P. acnes*, anti-*S. aureus*, anti-MRSA, anti-*Candida*, and anti-*E. coli* activities, (2) media and extracts obtained by growing live fermenting microorganisms in the presence of glycerol with anti-*P. acnes*, anti-*S. aureus*, anti-MRSA, anti-*Candida*, and anti-*E. coli* activities, and (3) live fermenting microorganisms formulated to inhibit the growth of *P. acnes, S. aureus*, MRSA, *Candida*, and *E. coli*. The use of these probiotics as innate therapeutics and for disease prevention is in compliance with evolutionary medicine and may have a lower risk of induction of resistant pathogens and cause undesirable side-effects on the skin.

The disclosure (Example 1) showed that bacterial antagonism defined as the formation of inhibition zones and bubble-like competed territories between *P. acnes* and skin microorganisms were detectable in the microbiome of fingerprints subjects. The data showed that more than forty microbial colonies from 10 volunteers formed inhibition zones against *P. acnes*. *S. epidermidis* EHa-1, a long-term resident microorganism in skin, and *Paenibacillus* sp., a short-term skin resident microorganism that is mainly found in the environment, have been identified from five of these colonies.

*S. epidermidis* has been previously shown to counteract the infection of *S. aureus* (Iwase et al., 2010) via a secreted serine protease. However, *S. epidermidis*, its fermentation medium or succinic acids produced by *S. epidermidis* have not been identified as capable of inhibiting the growth of *P. acnes*.

Example 1 provides that skin microorganisms inhibit the growth of *P. acnes* but only when certain conditions for glycerol fermentation are present. One of the microorganisms capable of inhibiting *P. acnes* was identified as *S. epidermidis* EHa-1 which developed an inhibition zone when it was co-cultured with *P. acnes* (Example 1). The results indicate that, under normal conditions with atmospheric oxygen supply, *S. epidermidis* lives on the skin surface with *P. acnes* without counteracting each other. However, *S. epidermidis* enters acne lesions when acne comedones are created by the overgrowth of *P. acnes* and under these conditions, the *S. epidermidis* microorganism, the *S. epidermidis* fermentation media, and the by-products of fermentation of *S. epidermidis* combat the overgrowth of *P. acnes*. In addition, the disclosure (Example 1) teaches that the succinic acid decreases inflammation associated with acne. Thus, the disclosure describes using *S. epidermidis* glycerol fermentation within an anaerobic acne lesion to combat acne.

Example 1 also provides that more than one microorganism or fermentation product can be used for the treatment and prevention of acne. The disclosure identifies two microorganism strains that interfere with the growth of *P. acnes* via fermentation that were isolated from the human skin microbiome to develop acne probiotics—*S. epidermidis* EHa-1, a long-term resident microorganism in skin, and *Paenibacillus* sp., a short-term skin resident microorganism that is mainly found in the environment and does not colonize the skin long-term. The disclosure identifies succinic acid, acetic acid, butyric acid, and lactic acid byproducts of fermentation that can be used for the treatment and prevention of acne.

Figure 8A:
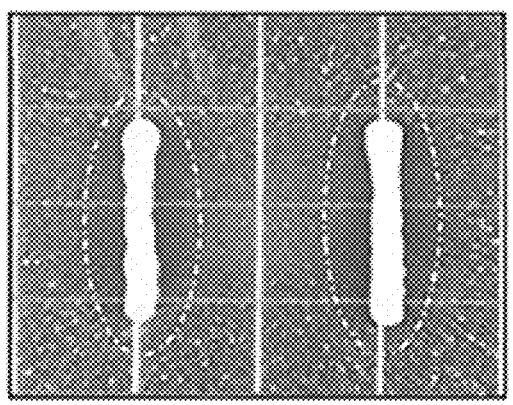
FIGS. 8A-G show probiotic effects of P. acnes fermentation against USA300. (A-D) An overlay assay revealed zones (circles) of inhibition of USA300 growth when P. acnes (ATCC6919, $10^5$ CFU) (A), but not M. luteus (B), was grown with USA300 in the presence of glycerol in agar plates under anaerobic conditions at 30° C. No inhibition zones were developed when P. acnes (C) or M. luteus (G) was grown with USA300 in the absence of glycerol. (E-G) The probiotic effect of P. acnes fermentation against USA300 was accompanied by a decrease in intracellular pH. (E) P. acnes ($10^5$ CFU/ml), was incubated in rich medium in the absence (■) and presence (•) of glycerol under anaerobic conditions for ten days. Rich medium plus glycerol without P. acnes (▲) was included as a control. (F) After a 17-day incubation, fermented or control media were then collected, diluted (½ to ¹⁄₁₆) and added to cultures of USA300 ($10^5$ CFU/ml) overnight. The inhibitory growth of USA300 was defined as a decline in $OD_{600}$. (G) The cFSE-loaded USA300 (3×$10^4$ CFU) was treated with 100 µl fermented (Medium+glycerol+P. acnes; solid bar) or control [(Medium+glycerol (open bar) and Medium+P. acnes (grey bar)] media. The change in the relative fluorescence units corresponding to intracellular pH of USA300 was measured 5 min after treatment. P<0.01; *P<0.001 (two-tailed t-tests). Data are the mean±standard deviation (SD) of three individual experiments. NS: Non-significant.
Figure 8C:
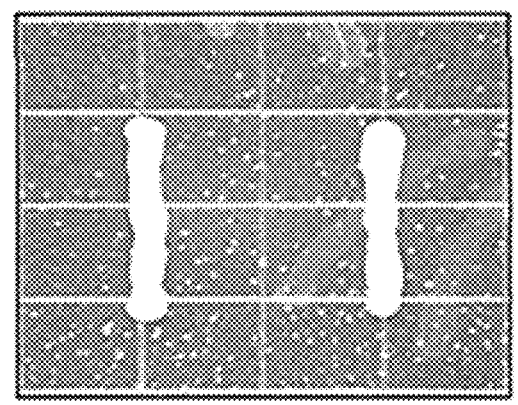
Figure 8B:
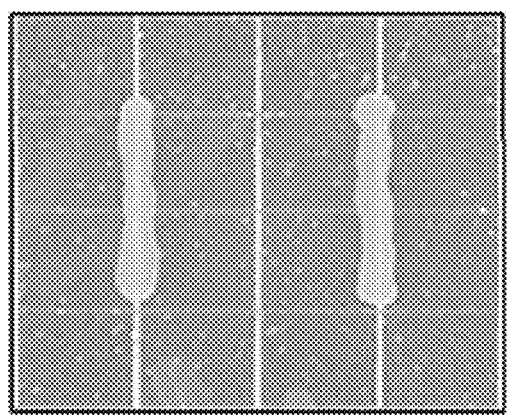
Figure 8D:
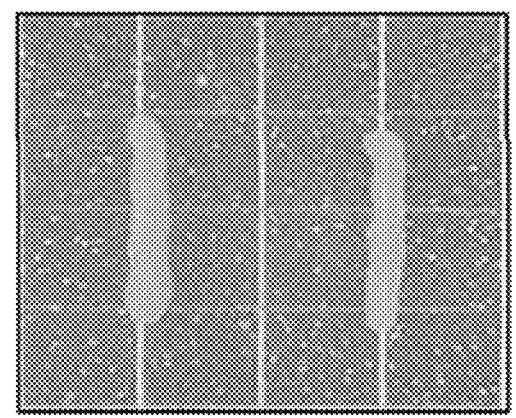
Figure 8E:
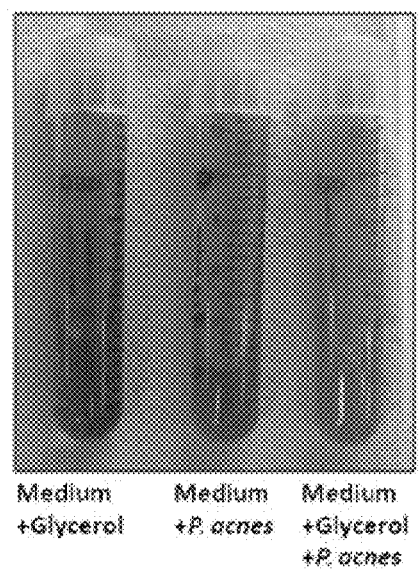
Figure 8F:
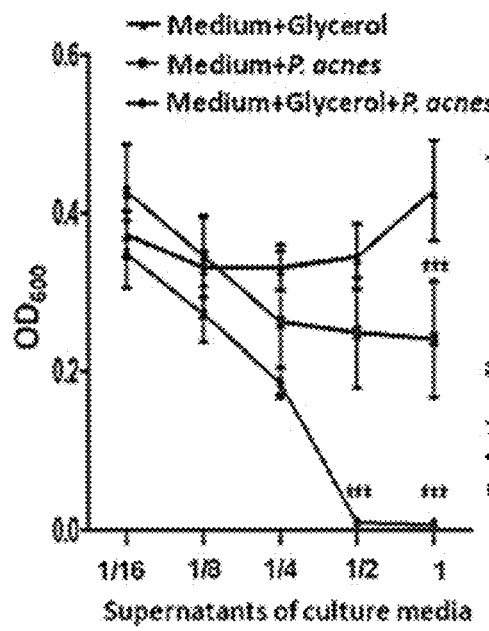
Figure 8G:
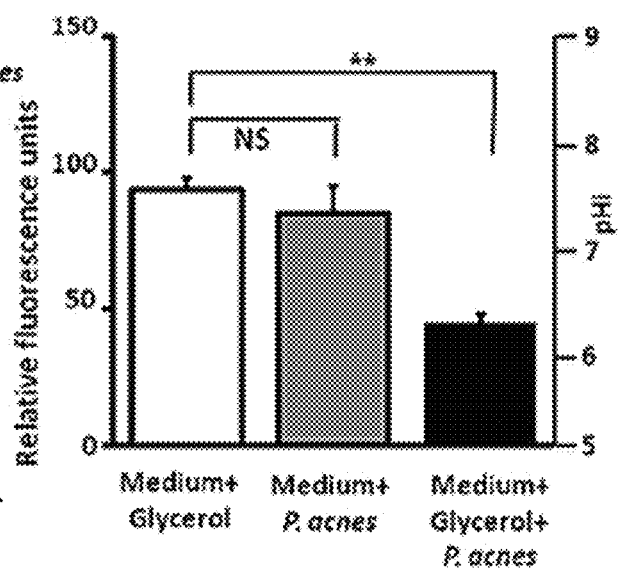

Examples 2 and 3 provide that a skin commensal bacterium *Propionibacterium acnes* (*P. acnes*), fermentation media obtained during glycerol fermentation of *P. acnes*, and by-products of *P. acnes* glycerol fermentation, the SCFAs derived from *P. acnes* during glycerol fermentation can be used as skin probiotics for treatment of skin infections by pathogens. Nearly everyone hosts *P. acnes* on their skin, which accounts for approximately half of the total skin microbiome, with an estimated density of $10^2$ to $10^{5-6}$ $cm^2$. As shown in the Example 2 and 3, USA300, a community-acquired methicillin-resistant *Staphylococcus aureus* (CA-MRSA) reported as the most common cause of purulent skin infections in the US, was selected as a pathogen to test the probiotic effect of *P. acnes* ferments. *P. acnes* was incubated in rich medium under anaerobic conditions in the presence of glycerol as the carbon source. Rich medium plus glycerol alone or *P. acnes* alone was used as a control. Phenol red, a fermentation indicator, was added into additional incubation of both experimental and control groups to monitor the fermentative process. As shown in FIG. 8G, media in cultures of *P. acnes* with glycerol, turned yellow ten days after incubation, demonstrating *P. acnes* fermentation. After 17-day incubation (FIG. 8G), the pH values in the rich medium containing glycerol, *P. acnes* alone and glycerol plus *P. acnes* showed values of 6.6, 6.5, and 5.6, respectively. To assess the anti-MRSA activity of *P. acnes* ferments, USA300 ($10^6$ CFU) was incubated with initial medium from fermentation and dilution (½ to ¹⁄₁₆) overnight. As shown in FIG. 8F, initial and a ½ dilution of fermented media markedly suppressed the growth of USA300.

Figure 9A:
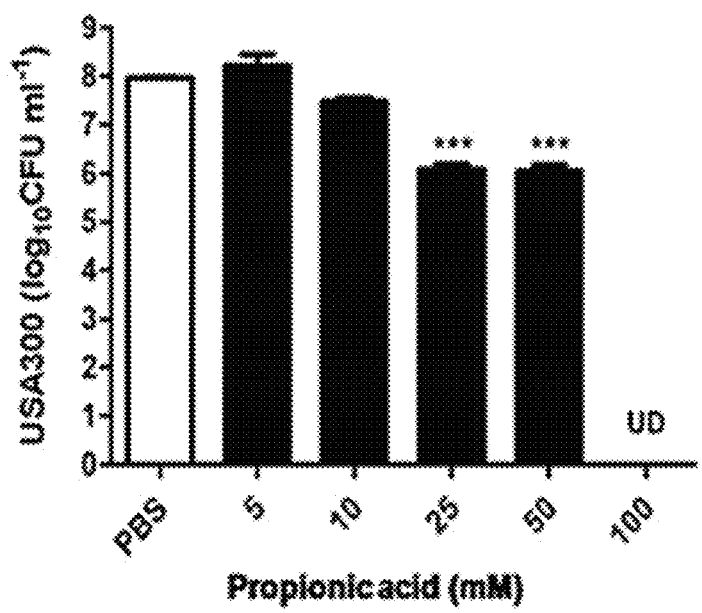
FIGS. 9A-B show the antimicrobial activity of propionic acid. For MBC assays (A), USA300 ($10^6$ CFU/ml) was incubated with propionic acid (5-100 mM in PBS) in media on a 96-well microplate overnight. Bacteria incubated with PBS alone were used as a control. After incubation, the microorganism was diluted 1:10-1:$10^6$ with PBS, and 5 µl of the dilutions were spotted on an agar plate for CFU counts. P<0.01; *P<0.001 (two-tailed t-tests). Data are the mean±SD of three individual experiments. UD, undetectable. For radial diffusion assays (B), USA300 at $10^5$ CFU per ml was dispersed in agar consisting of 1% (w/v) agarose and 1% (w/v) TSB in 10 mM PBS and then poured into Petri dishes to solidify. Wells of 3 mm in diameter were made in this agar. Then 30-μl propionic acid (5 to 100 mM) aliquots or PBS was added to the wells. After 3 h of incubation, a 10-ml overlay gel composed of 3% TSB powder and 1% agarose was poured onto the plates, and the plates were incubated overnight before measuring the growth inhibition zones in diameters.
Figure 9B:
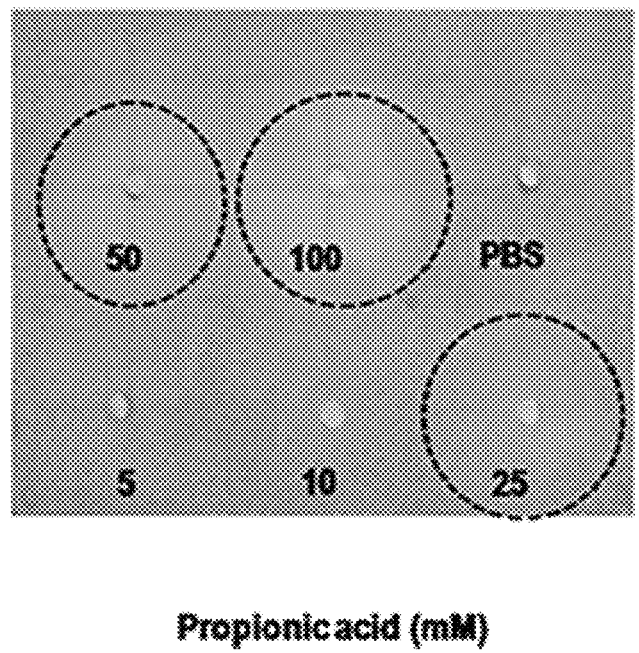
Figure 17A:
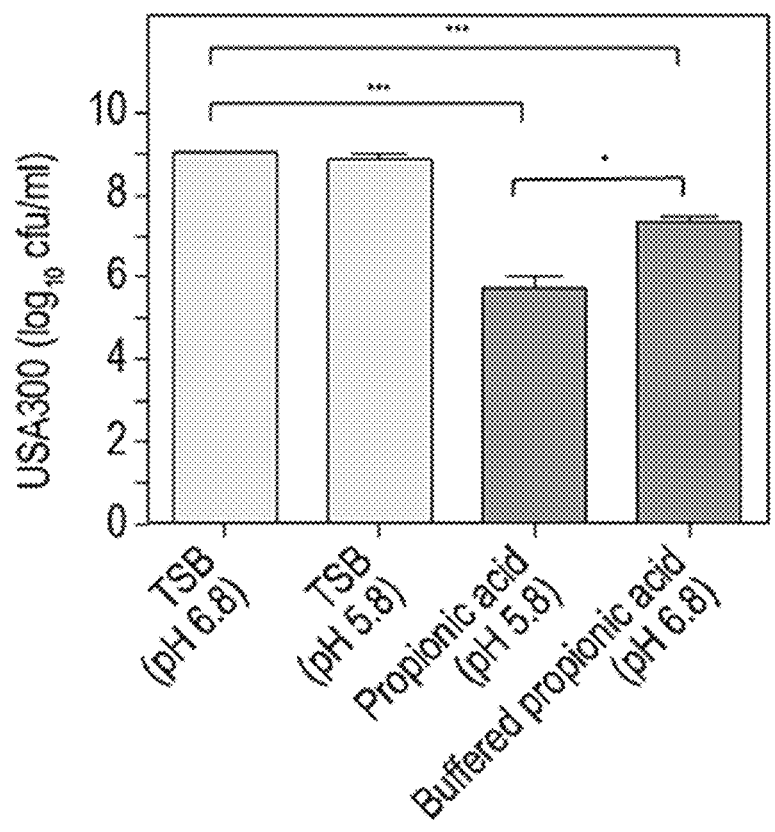
FIGS. 17A-B show (A) Effect of pH on activity of propionic acid against *Staphylococcus aureus* USA300 and (B) effect of propionic acid on intracellular pH (pHi) of this bacterium. PBS=phosphate buffered saline; TSB=tryptic soy broth. Data are the mean±standard deviation of three individual experiments. *$P<0.05$; ***$P<0.001$.

In the fermented media of *P. acnes*, propionic acid (4.1 µmole/ml) was detectable by high performance liquid chromatography (HPLC). A minimal bactericidal concentration (MBC) assay and radial diffusion assay (RDA) were performed to test if propionic acid exerts antimicrobial activity against USA300. As shown in FIG. 9, the MBC of propionic acid for suppression of the growth of USA300 in tryptic soy broth (TSB) was 25 mM. The colony-forming units (CFUs) of USA300 were not different when bacteria were incubated with TSB (pH 6.8) or TSB (pH 5.8) (FIG. 17A). Furthermore, the antimicrobial activity of propionic acid remained after buffering 25 mM propionic acid (pH 6.8) with ammonium hydroxide (FIG. 17A); thus demonstrating that buffering does not inhibit the activity in the propionic acid. To test the potency of propionic acid against MRSA in vivo, USA300 ($2\times10^6$ CFU) was inoculated to the skin wounds on the back of Institute of Cancer Research (ICR) mice 10 min after topical application of propionic acid (100 mM), or its controls (phosphate buffered saline (PBS) (pH 7.1) or PBS (pH 3.5, a value corresponding to pH for 100 mM propionic acid)). Application of propionic acid, but not its controls, considerably decreased USA300 colonization and the sizes of USA300-infected skin lesions (FIG. 10).

In addition to fermentation media and fermentation by-products (SCFAs) that were shows to have anti-MRSA and anti-*P. acnes* activity, the disclosure teaches anti-*P. acnes* probiotics containing live *S. epidermidis* EHa-1 and/or *Paenibacillus* sp. and anti-*S. aureus*, anti-MRSA, anti-*Candida* and anti-*E. coli* probiotics comprising *P. acnes*. Various other skin microorganisms can be identified that have specificity to fermentatively antagonize different pathogens and non-pathogens. Thus, other "skin probiotics" can be developed using fermentation of skin microorganisms for treatments of various skin infections, diseases and disorders.

This disclosure identifies various SCFAs that have novel antimicrobial properties. Succinic acid, one such SCFA is shown herein to have unexpected anti-*P. acnes* and inflammatory activities. As shown in Example 1, the application of succinic acid significantly neutralizes *P. acnes*-induced inflammation (FIG. 5).

In addition to SCFAs, the disclosure teaches buffered SCFAs that may be used as anti-*P. acnes*, anti-*S. aureus*, anti-MRSA, anti-*Candida*, and anti-*E. coli* agents In addition, the disclose teaches SCFA derivatives that that may be used as anti-*P. acnes*, anti-*S. aureus*, anti-MRSA, anti-*Candida*, and anti-*E. coli* agents (Example 3).

Figure 11F:
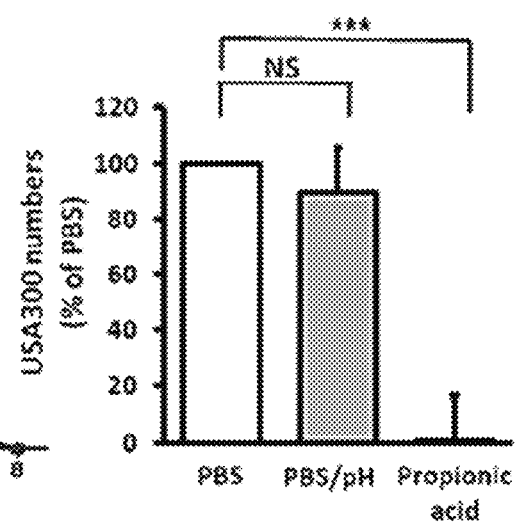
Figure 13A:
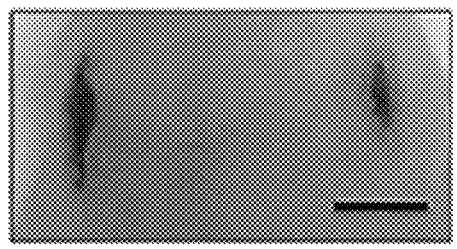
Figure 16:
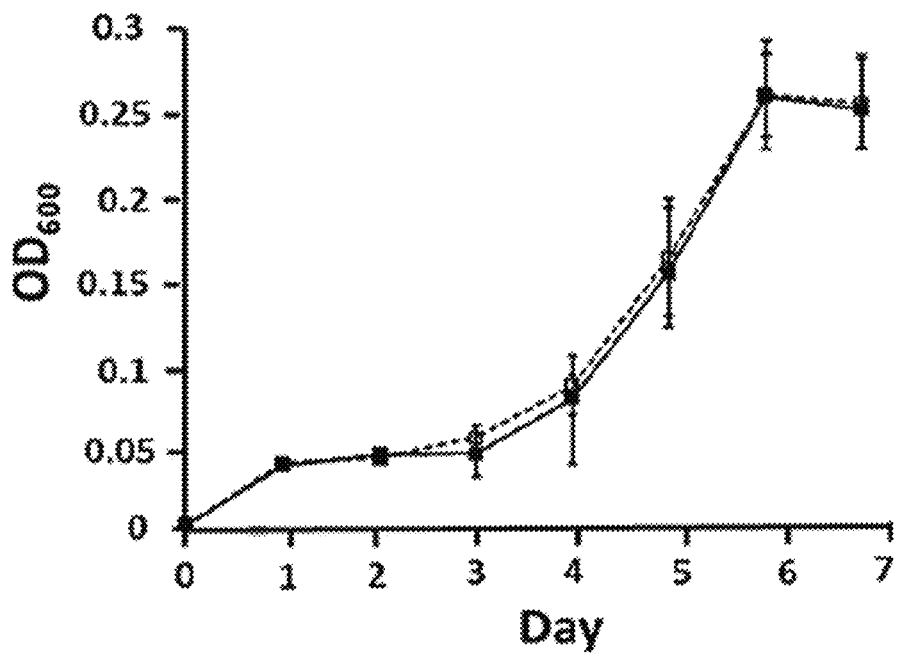
FIG. 16 shows a comparison of growth curves of P. acnes in the absence of presence of glycerol. P. acnes was incubated in rich medium in the absence (□) and presence (■) of glycerol on a 96-well microplate under anaerobic conditions at 30° C. The $OD_{600}$ was read at the indicated time points. Data are the mean±SD of three separate experiments. Glycerol did not change significantly the growth of P. acnes.

As shown in Example 2, the inhibitory effect of *P. acnes* on the growth of USA300 was detectable through glycerol fermentation. Glycerol itself did not influence the growth of *P. acnes* (FIG. 16) and USA300. in addition to using propionic acid to inhibit USA300 in vitro (FIG. 11D) and in vivo (FIG. 11F), a fermented media obtained by fermentation of *P. acnes* in glycerol and *P. acnes* bacterium itself also exhibited the anti-USA300 effects (FIG. 11 A, B, C and FIGS. 13A and C).

Furthermore, the disclosure provides naturally occurring extracts of fermentation from skin commensal bacteria that can be used to treat pathogenic (non-commensal) infections.

Additionally, as described herein, compositions comprising SCFAs (an individual SCFA or SCFA combinations) obtained synthetically or obtained from culturing microbial populations in the presence of an appropriate substrate to produce extracts, can be used to treat or balance skin microflora.

In some embodiments, the fermented media, extracts and/or SCFAs are purified or substantially purified from other material in the milieu. Such combinations of SCFA's or extracts can be buffered and prepared as lotions, ointments and the like to treat various skin diseases and disorders. In addition, various prodrug (SCFA derivatives) formulations can be prepared.

Example 1

Culture of Microorganisms.

*P. acnes* (ATCC6919) was cultured in Reinforced *Clostridium* Medium (RCM, Oxford, Hampshire, England) under anaerobic conditions using Gas-Pak (BD, Sparks, Md., USA) at 37° C. Human skin microorganisms were isolated by moving a sterile inoculating loop (Fisher Scientific, San Diego, Calif., USA) along the nose surface of a male volunteer without acne vulgaris. The isolated skin microorganisms containing a mixture of various microbes were cultured in TSB (Sigma, St. Louis, Mo., USA). Overnight cultures were diluted 1:100 and cultured to an absorbance at 600 nm [optical density $(OD)_{600}$]=1.0. Microorganisms were harvested by centrifugation at 5,000 g for 10 min, washed with PBS, and suspended in PBS.

*P. acnes* Growth in a Homogeneous Microbial Lawn.

The skin microorganisms or *P. acnes* ($10^5$ CFU) were mixed with 1% agar (Oxoid. Ltd., London, UK) with/without glycerol (20 g/l) in TSB. The microbial suspension/agar was poured into plates to produce a homogeneous lawn of microbes. *P. acnes* or skin microorganisms with a serial dilution ($10^7$-$10^2$ CFU in 20 μl in PBS) were spotted on the top of microbial lawn under anaerobic conditions at 30° C. for six days for CFU counts.

Bacterial Antagonism (Interference) in the Fermented Skin Fingerprints.

Fingerprints of index, middle, and ring fingers were pressed onto the surfaces of agar plates composed of rich medium (10 ml) [10 g/l yeast extract (Biokar Diagnostics, Beauvais, France), 5 g/l TSB, 2.5 g/l $K_2HPO_4$ and 1.5 g/l $KH_2PO_4$] supplemented with/without glycerol (20 g/l). To mimic the overgrowth of *P. acnes* in lesions of acne vulgaris, a high dose of *P. acnes* ($10^7$ CFU in 5 μl PBS) was spotted on the central portion of fingerprints and grew for six days at 30° C. under anaerobic conditions using Gas-Paks. Seventeen volunteers (11 males and 6 females) participated in fingerprinting on agar plates. All volunteers were asked to not wash their hands before pressing fingerprints. The sequence analysis of 16S rRNA genes was performed to identify the microorganisms in fingerprints. Single colonies of microorganisms were picked up by sterile toothpicks and were grown in TSB. After DNA extraction, PCR with 16S rRNA 27F and 534R primers and sequencing of PCR products were conducted. The 16S rRNA gene sequences were analyzed in the basic local alignment search tool (BLASTn).

Fermentation of Microorganisms.

The skin microorganisms (10 CFU/ml) isolated from the surface of human nose were incubated in rich medium in the absence and presence of 20 g/l glycerol under anaerobic conditions at 30° C. Rich medium plus 20 g/l glycerol without microorganisms was included as a control. The 0.001% (w/v) phenol red (Sigma, St. Louis, Mo., USA) in rich medium with 20 g/l glycerol served as an indicator, converting from red-orange to yellow when fermentation occurred.

Identification of SCFAs in the Fermented Media of Microorganisms by NMR Analysis.

The skin microorganisms were incubated in phenol red-free rich medium with $^{13}C_3$-glycerol (20 g/l) (Cambridge Isotope Laboratories, Andover, Mass., USA) for six days. After that, microorganisms were discarded by centrifugation at 5,000 g for 30 min. Fermented media were then passed through 0.2-μm-pore-size filters. SCFAs and other metabolites in the microorganism-free media were identified by NMR analysis. The 1-D NMR spectra were measured on a JEOL-ECS NMR spectrometer operating at resonance frequency of 400 MHz with a repetition delay of 3 sec for both $^1H$ and $^{13}C$. The 2-D $^1H$-$^{13}C$ heteronuclear single quantum correlation (HSQC) NMR spectra were acquired on a Bruker Avance 600 MHz NMR spectrometer with a triple resonance inverse (TCI) cryo-probe and recorded as 2048×256 complex points with 32 scans and 1 sec repetition time. Newly appearing peaks were intermediates or final products resulting from $^{13}C_3$-glycerol fermentation by microorganisms.

MBC Assays.

To determine the MBC values of SCFAs, *P. acnes* ($10^8$ CFU/ml) was incubated with SCFAs at various concentrations (2.5-100 mM in PBS) as indicated in each individual experiment in media on a 96-well microplate (100 μl per well) overnight. The control received only PBS. After incubation, the bacteria were diluted 1:10-1:$10^6$ with PBS. MBC was defined as a 99.9% killing level and determined by spotting the dilution (5 μl) on an agar plate supplemented with media for CFU counting. To determine the effect of pH on its growth, *P. acnes* in PBS was incubated with 5 mM succinic acid on a 96-well microplate (100 μl per well) overnight before spotting on an agar plate. As controls, *P. acnes* was incubated with PBS (pH 7.4) alone, PBS (pH 5.5; a pH value corresponding to the MBC of succinic acid in PBS), or buffered succinic acid (5 mM succinic acid, pH 7.4 buffered with ammonium hydroxide).

Measurement of Intracellular pH.

Measurement of intracellular pH of *P. acnes* was performed using a cFSE florescence probe (Life Technologies, Grand Island, N.Y.) Bacteria were loaded with cFSE (5 μM) for 30 min at 37° C. in 50 mM HEPES and 5 mM ethylenediaminetetraacetic acid (EDTA). To eliminate unbound probe, bacteria were incubated with glucose (10 mM) for an additional 30 min, washed twice in 50 mM PBS with 10 mM $MgCl_2$, pH 7.0, and then re-suspended in 1 mM PBS. The cFSE-loaded bacteria ($3\times10^4$ CFU) were dispensed in on a 96-well microplate containing 100 μl/per well of PBS or succinic acid (5 mM). Fluorescence intensities were measured immediately and every min for 5 min using an excitation wavelength of 490 nm and emission wavelength of 520 nm. A drop in relative fluorescence indicates the decrease in intracellular pH. Fluorescence of the bacteria-free filtrate (background fluorescence) was measured after the 5-min assay. The treated suspensions were centrifuged at 5,000 g for 5 min, the fluorescence of the bacteria-free supernatant was measured. Calibration curves were obtained by incubation of un-treated, cFSE-loaded bacteria in buffers of various pHs. The buffer containing glycine (50 mM), citric acid (50 mM), $Na_2HPO_4 \cdot 2H_2O$ (50 mM), and KCl (50 mM) was adjusted to various pH values ranging from 4 to 10. Equilibration of the intracellular and extracellular pH was conducted by addition of 1 μM valinomycin and nigericin (Sigma, St. Louis, Mo.).

In Vivo Effects of Succinic Acid on *P. acnes* Colonization and *P. acnes*-Induced Inflammation.

ICR mice (2-3 month-old females; Harlan Labs, Placentia, Calif., USA) were anesthetized by isoflurane. Five mice per group per experiments were used. The ears of ICR mice were injected intradermally with *P. acnes* ($10^7$ CFU in 10 μl PBS) or PBS (20 μl) a 28-gauge needle. One day after injection, succinic acid (5 mM; 10 μl) or PBS was intralesionally injected into inflamed lesions for two days. For topical application, succinic acid (100 mM) or PBS was topically applied onto the surface of inflamed lesions once per every day for 3 days. Succinic acid or PBS was topically applied on mouse ear away from the needle injection sites to avoid it entering dermis via a hole created by needle injection. Ears were excised and homogenized for cytokine detection and bacterial counts. The MIP-2 in supernatants was measured by an enzyme-linked immunosorbent assay (ELISA) kit as directed by the manufacturer (BD Biosciences, San Diego, Calif.). To determine the bacterial counts in *P. acnes*-inoculated ears, mouse ears were excised and homogenized in 200 μl of sterile PBS with a tissue grinder. Bacterial CFUs in the mouse ears were enumerated by plating serial dilutions ($1:10^1$-$1:10^6$) of the homogenate on a TSB agar plate. The plate was incubated for 3 days at 37° C. to count colonies. A Student's t-test was used to determine the significance of the differences between groups. Data represented the mean±SD from three independent experiments. All experiments using mice were conducted in a biosafety level 2 (BSL-2) facility and in accordance with institutional guidelines for animal experiments.

Microbial Antagonism Mediated by Fermentation.

Figure 1B:
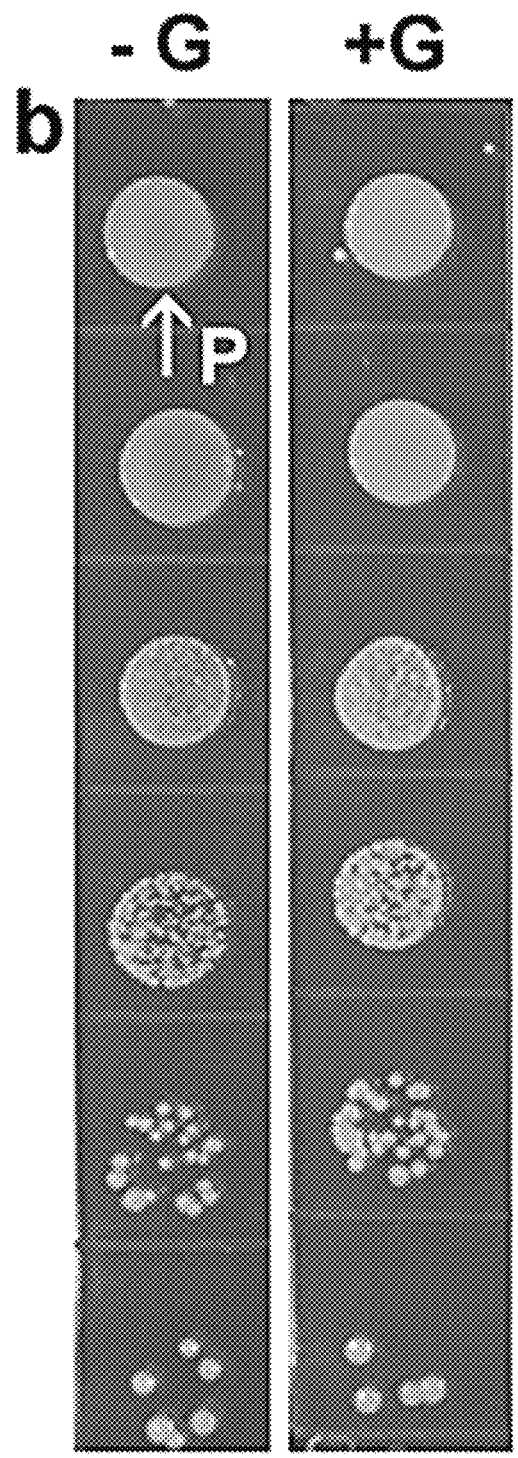

*P. acnes* with a serial dilution were spotted on the top of a homogeneous lawn of skin microorganisms microbial lawn. As shown in FIG. 1A, the colonies of *P. acnes* were significantly reduced (>one order of $\log_{10}$) when they were grown on the top of microbial lawn in the presence of glycerol under anaerobic conditions for 3 days. The reduction was not observed when the growth of *P. acnes*/skin microorganisms in an agar plate was incubated under aerobic conditions. The colony numbers of *P. acnes* were the same when *P. acnes* were grown on regular agars (without a microbial lawn on the bottom) that were with/without glycerol (FIG. 1B).

Bacterial Antagonism in the Fermented Skin Fingerprints.

Fingerprints of index, middle, and ring fingers were pressed onto the surface of agar plates supplemented with/without glycerol. To mimic the overgrowth of *P. acnes* in lesions of acne vulgaris, a high dose of *P. acnes* (ATCC6919; $10^7$ CFU) was dropped on the central portion of fingerprints. The interaction between *P. acnes* and skin microorganisms on fingerprints were observed daily. *P. acnes* grew into a larger colony and was surrounded by skin microorganisms six days after incubation under anaerobic conditions (FIG. 2A). On the glycerol-free agar plates, the colonies of *P. acnes* and skin microorganisms grew close to each other without developing inhibition zones (FIG. 2B). On the glycerol-containing agar plates, inhibition zones were detected on the boundary between colonies of *P. acnes* and skin microorganisms. Some skin microorganisms created bubble-like competed territories within a colony of *P. acnes*. The bubble-like competed territories were not due to the gas production during fermentation because they were not formed within a large *P. acnes* colony that grew at the same agar plate, but far away from skin microorganisms. These results suggested that skin microorganisms can interference with the growth of *P. acnes* via glycerol fermentation.

The sequence analysis of 16S rRNA genes was performed to identify skin microorganisms. Single colonies of two skin microorganisms that created inhibition zones on the boundary of a *P. acnes* colony were picked up by sterile toothpicks and grew in TSB (FIG. 2A). The polymerase chain reaction (PCR) using isolated DNA with 16S rRNA 27F and 534R primers and DNA sequencing were conducted. The 16S rRNA genes derived from the colony 1 shared 94% identify with the 16S rRNA genes in *S. epidermidis* ATCC1228 and *S. epidermidis* RP62A. The colony 1 was assigned as *S. epidermidis* EHa-1. The 16S rRNA genes derived from the colony 2 have 96% homology to the 16S rRNA genes in *Paenibacillus* species (*Paenibacillus* sp.) Y412MC10. The colony 2 was assigned as *Paenibacillus* sp. *S. epidermidis* is a facultative bacterium and can undergo fermentation under anaerobic conditions. *Paenibacillus* is a genus of facultative anaerobic, Gram-positive bacteria, can be detected in a variety of environments such as soil and water.). *Paenibacillus* sp. is not a permanent skin bacterium.

SCFAs in Fermented Media of Skin Microorganisms.

Figure 3A:
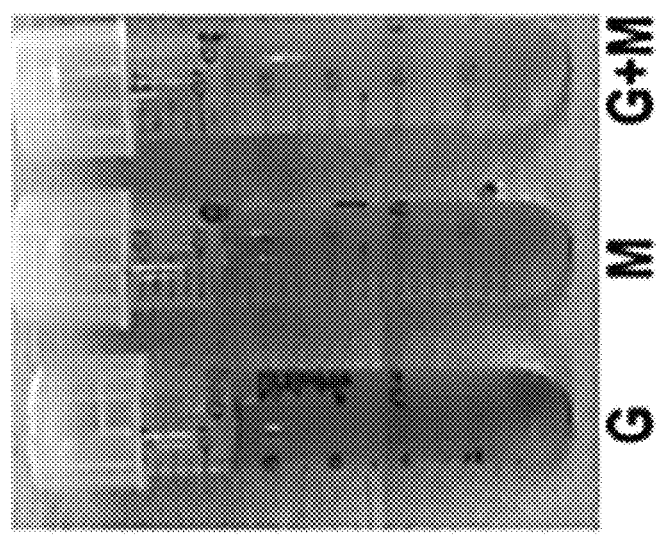
FIGS. 3A-D show the identification of SCFAs in the fermented media of skin microorganisms. (A) Skin microorganisms ($10^5$ CFU/ml) were incubated in rich medium in the absence (M) and presence (G+M) of glycerol for six days under anaerobic conditions. Rich medium plus glycerol without skin microorganisms (G) was included as a control. Fermented media of skin microorganisms were centrifuged and passed through a 0.2 µm filter. Supernatants were then mixed with 10% deuterium oxide ($D_2O$) and analyzed by NMR spectrometers. Representative 1-D 1H-(B) and $^{13}$C-(C) NMR spectra (400 MHz) that reveal the principal SCFAs in the fermented media six days after addition of $^{13}C_3$-glycerol. (D) A 2-D $^1$H-$^{13}$C HSQC NMR spectrum (600 MHz) was displayed. In addition to glycerol (G), ethanol (E), alanine (A), four SCFAs [acetic acid (Ac), butyric acid (B), lactic acid (L), and succinic acid (S)] were detected in the ferments of skin microorganisms.
Figure 3B:
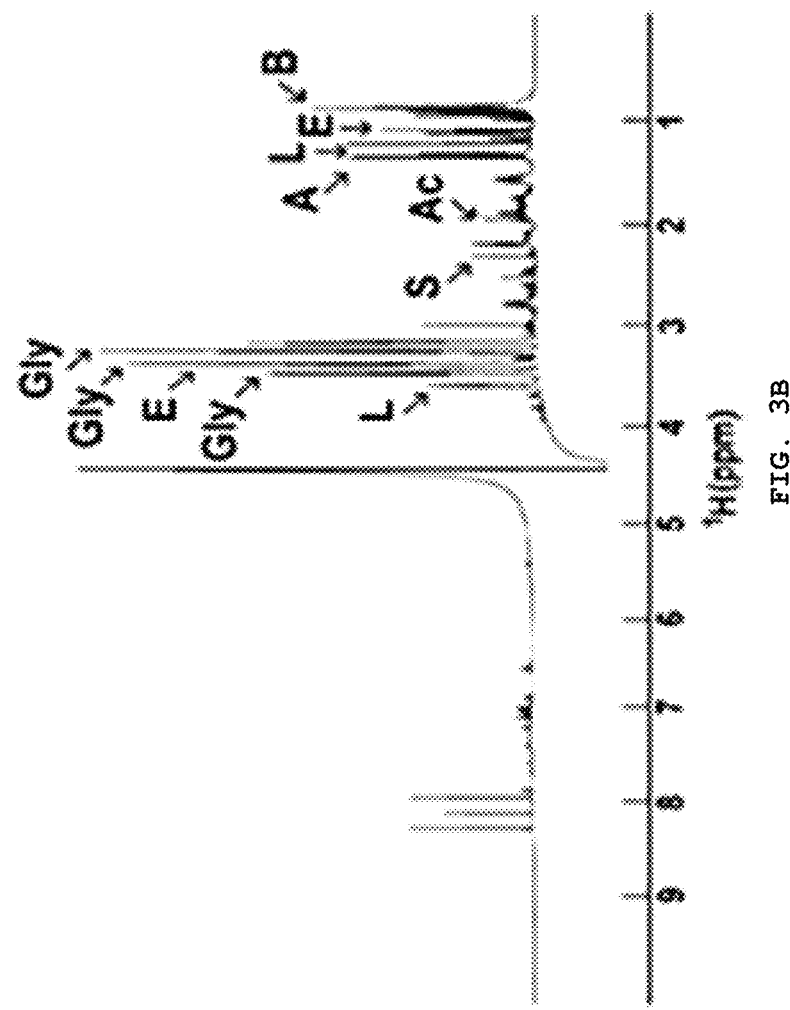
Figure 3C:
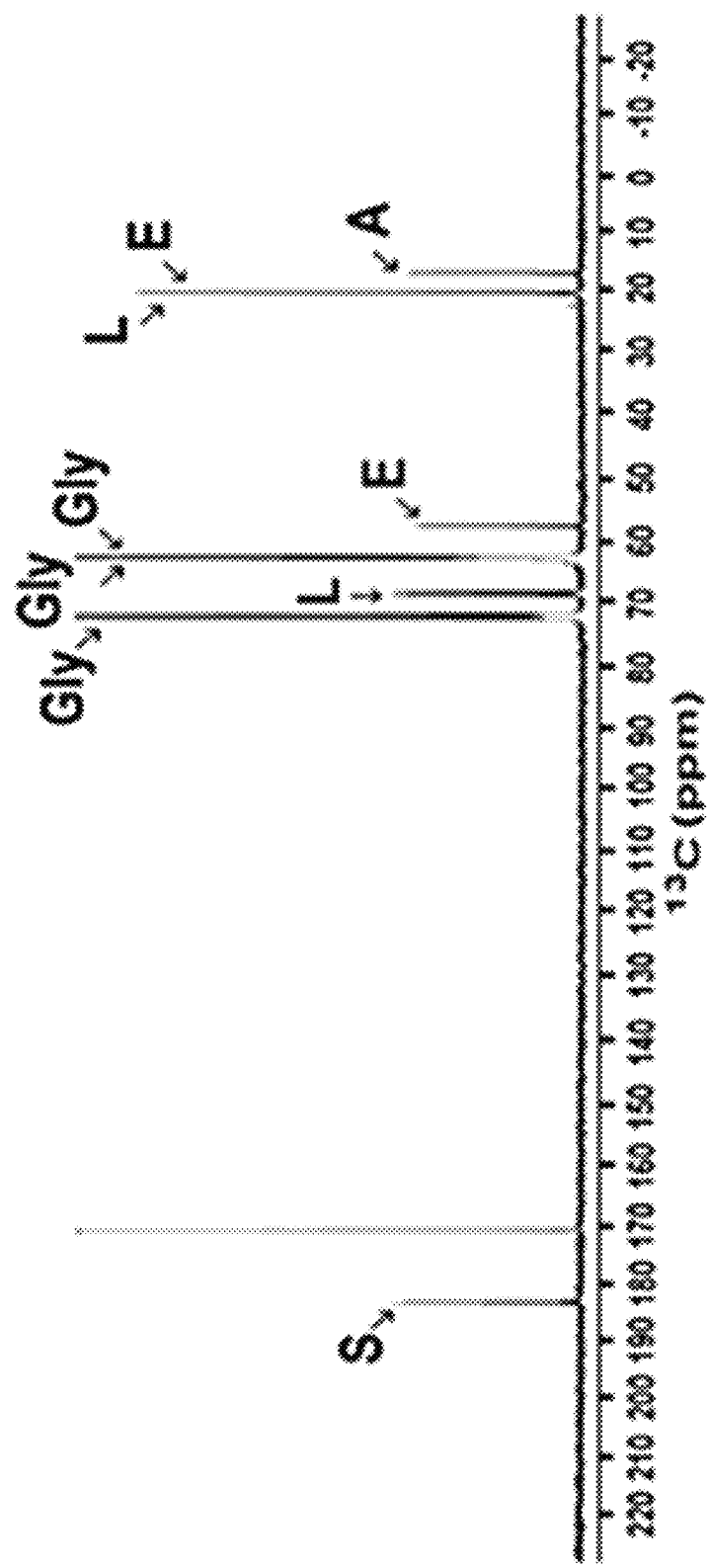
Figure 3D:
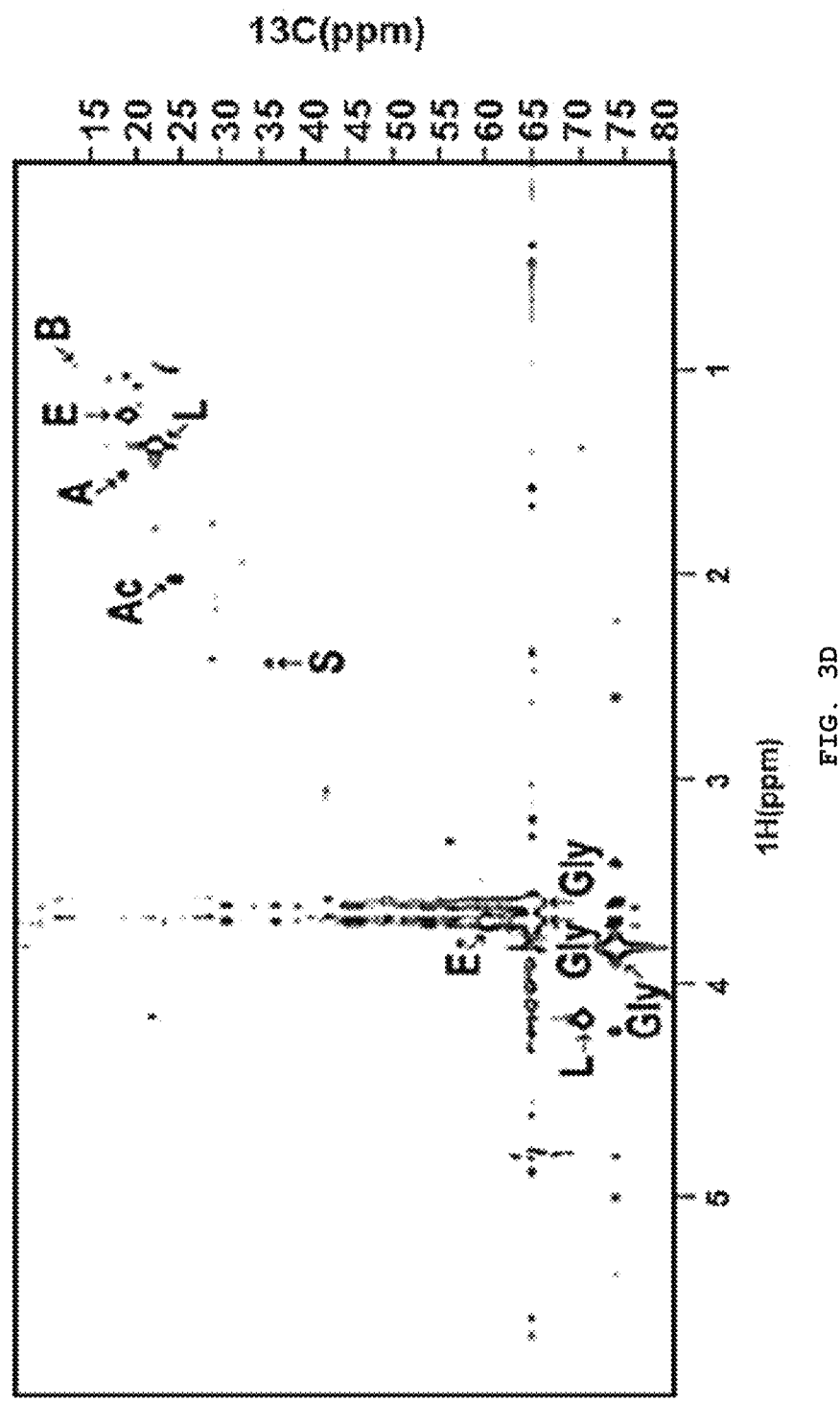

To examine the fermentation activity, the skin microorganisms were incubated in rich medium under anaerobic conditions in the presence of glycerol. Rich medium plus glycerol and rich medium plus skin microorganisms were used as controls. To monitor the fermentation process, cultures were tested with phenol red, a fermentation indicator, to assess SCFA production as a result of glycerol fermentation. Only media in the culture of skin microorganisms with glycerol turned yellow (more acidic) six days following incubation (FIG. 3A), indicating fermentation of skin microorganisms. This was further validated quantitatively by pH values in rich medium containing glycerol, microorganisms and glycerol plus microorganisms of 6.5, 6.4, and 6.0, respectively, following 6 days of incubation. To identify the SCFAs in the ferments, the skin microorganisms were incubated in rich medium under anaerobic conditions in the presence of $^{13}C_3$-glycerol (20 g/l) for six days. Supernatants of microbial fermentation in 10% $D_2O$ were subjected to one- (FIG. 3 B, C) and two-dimensional (1- and 2-D)$^{13}C$ and $^1H$ nuclear magnetic resonance (NMR) analysis. In addition to ethanol and alanine, four SCFAs [acetic acid, butyric acid, lactic acid, and succinic acid] were detected in the fermented media (FIG. 3D).

Succinic Acid Inhibited the *P. acnes* Growth Via Reduction of Intracellular pH of *P. acnes*.

Figure 4A:
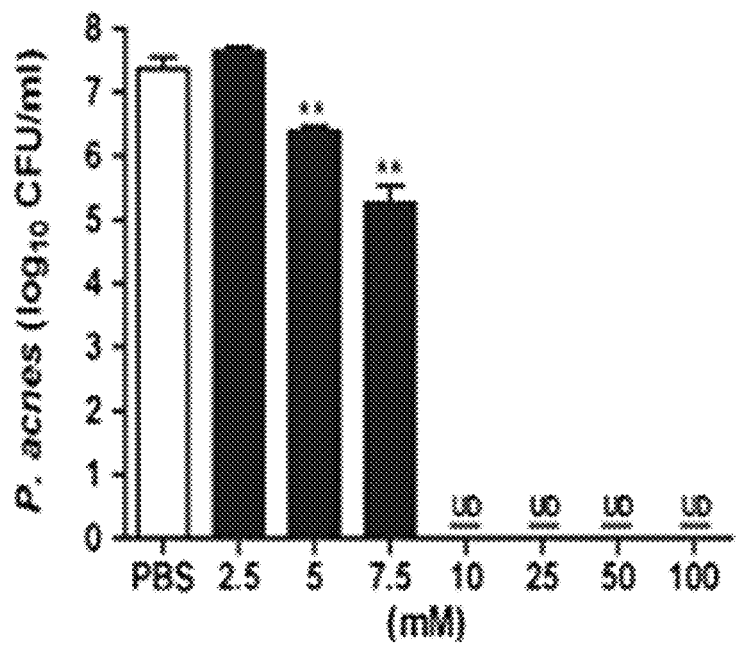
FIGS. 4A-C show the MBC of succinic acid against P. acnes, the effect of pH on the anti-P. acnes activity of succinic acid, and the decrease in intracellular pH of P. acnes by succinic acid. (A) P. acnes ($10^8$ CFU/ml) was incubated with succinic acid (2.5-100 mM in PBS) in media on a 96-well microplate overnight. Bacteria were incubated with PBS alone as a control. (B) P. acnes was incubated with PBS (pH 7.4), PBS (pH 5.5), succinic acid (at a concentration of 5 mM at pH 5.5) or ammonium hydroxide-buffered succinic acid (at a concentration of 5 mM at pH 7.4) to determine if the acidity of 5 mM succinic acid affects the P. acnes growth. After incubation, P. acnes was diluted 1:10-1:$10^6$ with PBS, and 5 µl of the dilutions were spotted on an agar plate for CFU counts. (C) The cFSE-loaded P. acnes (3×$10^4$ CFU) was treated with 5 mM succinic acid or PBS. The change in the relative fluorescence units corresponding to intracellular pH of P. acnes was measured 5 min after treatment. P<0.01; *P<0.001 (two-tailed t-tests). Data are the mean±standard deviation (SD) of three individual experiments. UD, undetectable.
Figure 4B:
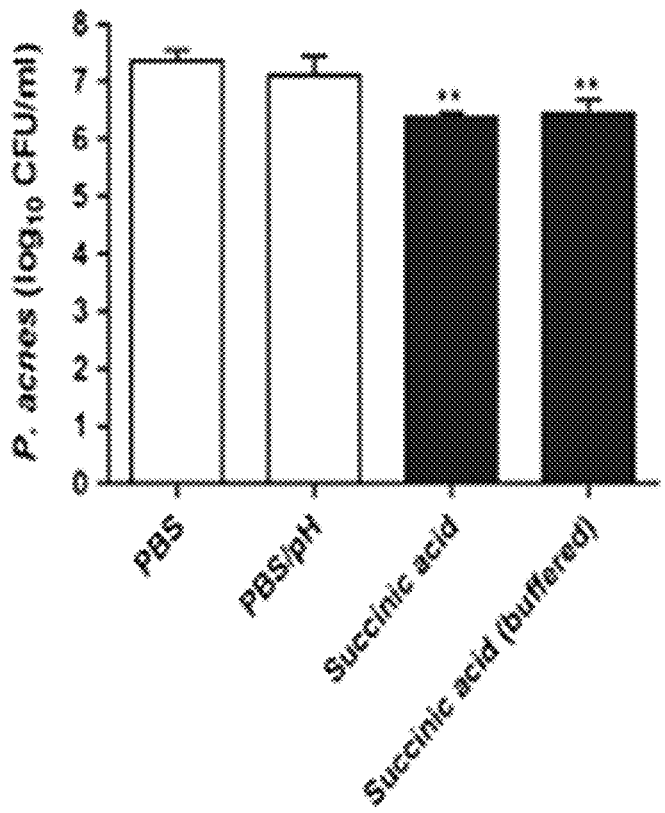
Figure 6A:
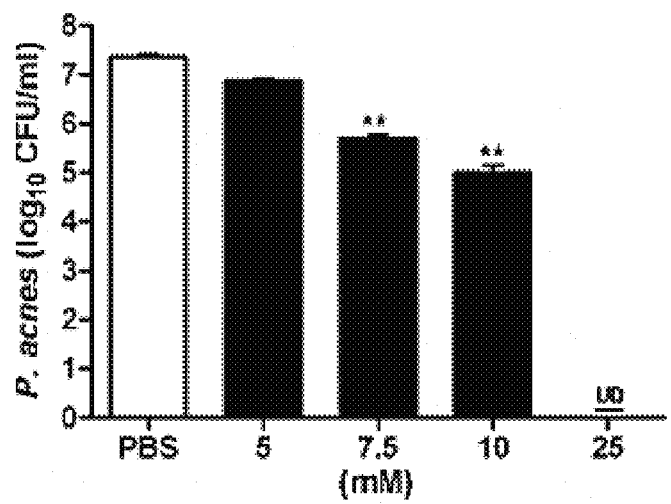
FIGS. 6A-C show MBC assays of SCFAs against P. acnes. (A-C) P. acnes ($10^8$ CFU/ml) was incubated with acetic acid (A), butyric acid (B), or lactic acid (C) at a concentration of 5-25 mM in PBS in media on a 96-well microplate overnight. Bacteria incubated with PBS alone as a control. After incubation, P. acnes was diluted 1:10-1:$10^6$ with PBS, and 5 µl of the dilutions were spotted on an agar plate for CFU counts. **P<0.01; (two-tailed t-tests). Data are the mean±SD of three individual experiments. UD, undetectable.
Figure 6B:
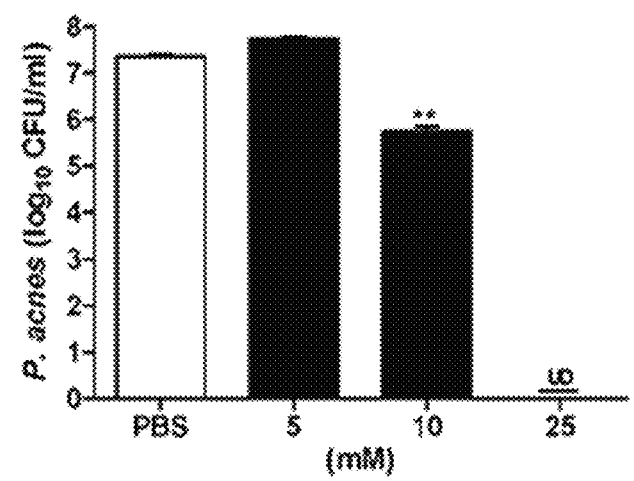
Figure 6C:
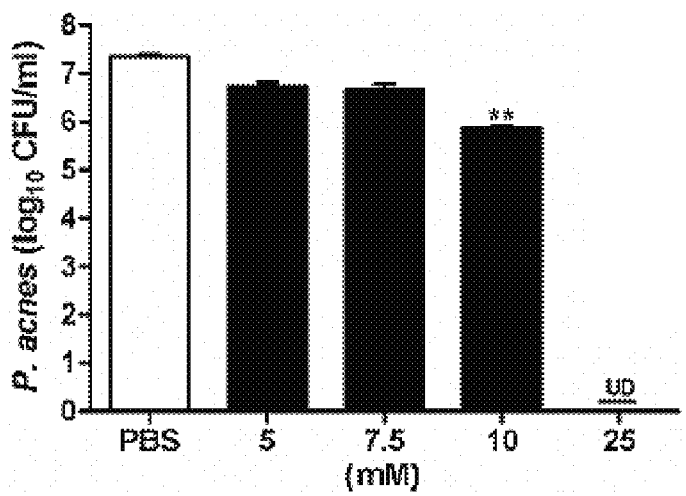
Figure 7A:
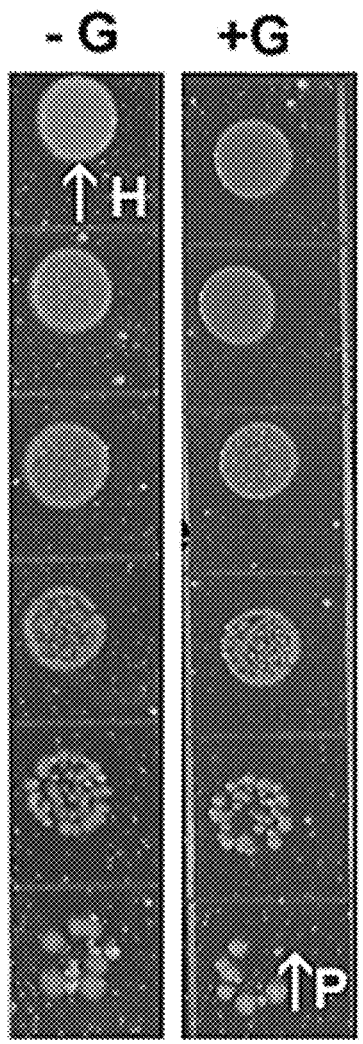
FIGS. 7A-B show no inhibitory effect of fermentation of P. acnes on the growth of skin microorganisms. (A) A homogeneous P. acnes lawn was created by pouring the P. acnes (P, arrow; $10^5$ CFU) that were pre-mixed with 1% agar with/without glycerol (+G/−G; 20 g/l) in TSB. The skin microorganisms (H, arrow) with a serial dilution ($10^9$-$10^4$ CFU in 20 µl in PBS) were spotted on the top of P. acnes lawn for three days for CFU counts. (B) The serially diluted skin microorganisms were spotted on the regular plates (without pouring P. acnes) with/without glycerol (+G/−G; 20 g/l).
Figure 7B:
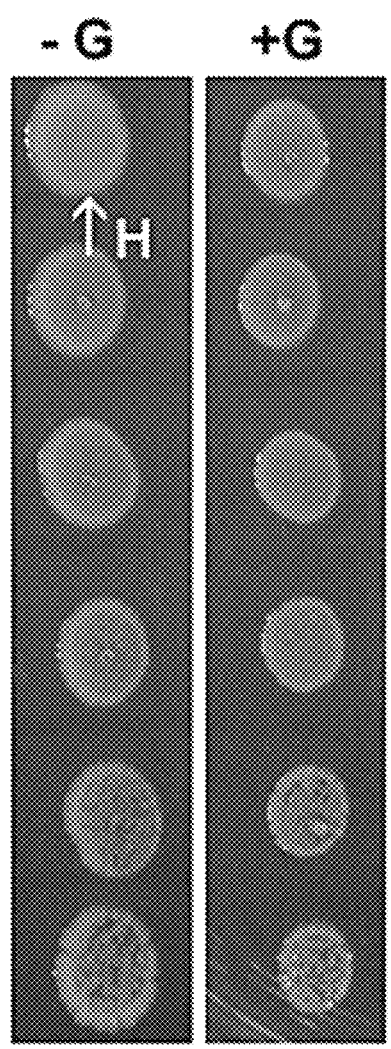

The minimal bactericidal concentration (MBC) assays were performed to determine if SCFAs exert the antimicrobial activities against *P. acnes*. Bacteria were incubated with acetic acid, butyric acid, lactic acid, and succinic acid various concentrations in media for 24 h. After incubation, the bacteria were diluted with PBS and spotted on an agar plate to count CFUs. The MBC values of acetic acid, butyric acid, lactic acid, and succinic acid against *P. acnes* are 7.5, 10, 10, and 5 mM, respectively (FIGS. 4A and 6). The succinic acid had the lowest MBC value. Succinic acid effectively suppressed the growth of P. acnes at concentrations≥25 and 7.5 mM, and complete killed P. acnes at a concentration ≥210 mM (FIG. 4A). To assess the acidity (pH 5.5) of 5 mM succinic acid in affecting growth of P. acnes, bacteria were incubated with PBS (pH 5.5) or ammonium hydroxide-buffered succinic acid (pH 7.4). Incubation of P. acnes with PBS (pH 5.5) did not alter the growth of P. acnes. The antimicrobial activity of succinic acid persisted even after buffering 5 mM succinic acid with ammonium hydroxide (FIG. 4B). The ability to suppress P. acnes growth by succinic acid was unrelated to direct killing by extracellular acidification.

Figure 4C:
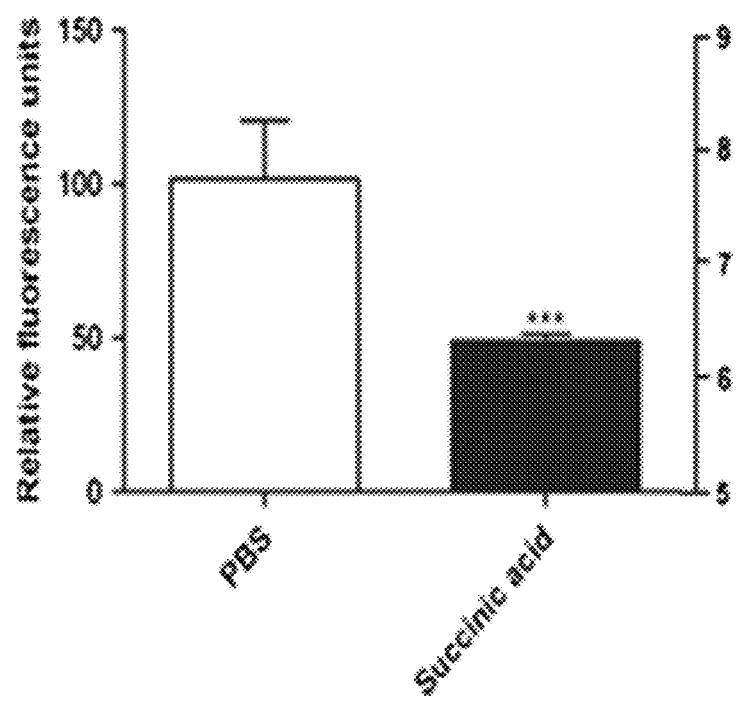

P. acnes was loaded with an internally conjugated fluorescent pH probe, carboxyfluorescein succinimidyl ester (cFSE). As shown in FIG. 4C, succinic acid significantly lowered the intracellular pH of P. acnes and killed P. acnes.

In Vivo Efficacy of Succinic Acid Against P. acnes.

Figure 5A:
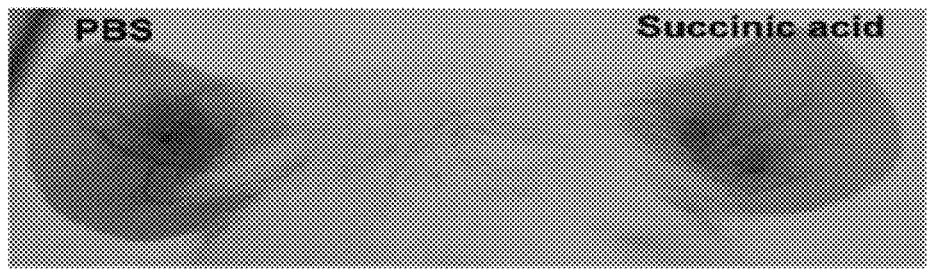
FIGS. 5A-C show that succinic acid suppresses P. acnes-induced inflammation and decreases bacterial colonization in vivo. (A) The ears of ICR mice were injected intradermally with P. acnes ($10^7$ CFU in 10 µl PBS) or PBS (10 µl). One day after injection of P. acnes or PBS, succinic acid or PBS was intralesionally injected into inflamed lesions or topically applied on the surface of inflamed lesions once per day. Photos of ear inflammation were taken four days after P. acnes injection. (B) The levels of MIP-2 cytokines in the homogenates of succinic acid- or PBS-treated ears were measured by an ELISA kit. (C) The CFUs in the ears treated with succinic acid or PBS were enumerated by plating serial dilutions (1:$10^1$-1:$10^6$) of the homogenate on a TSB agar plate. ***P<0.001; *P<0.05. P-values were evaluated using two-tailed t-tests. Data are the mean±SD of three ear lesions per group.
Figure 5B:
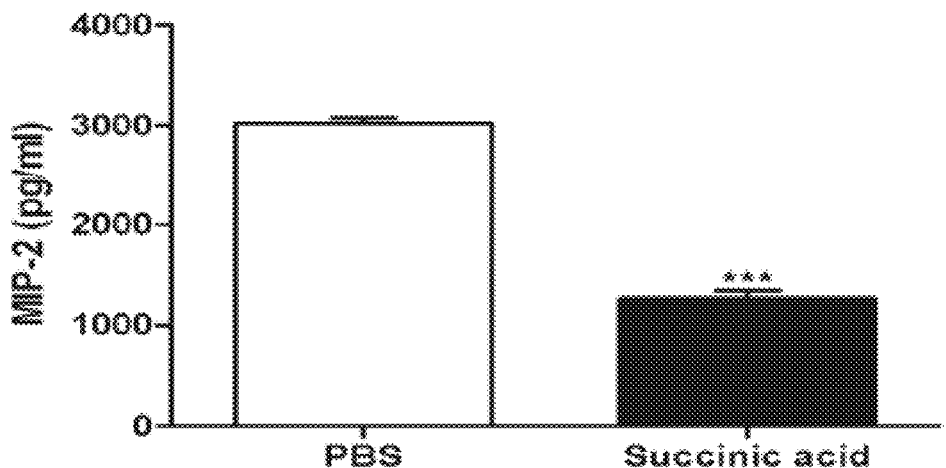
Figure 5C:
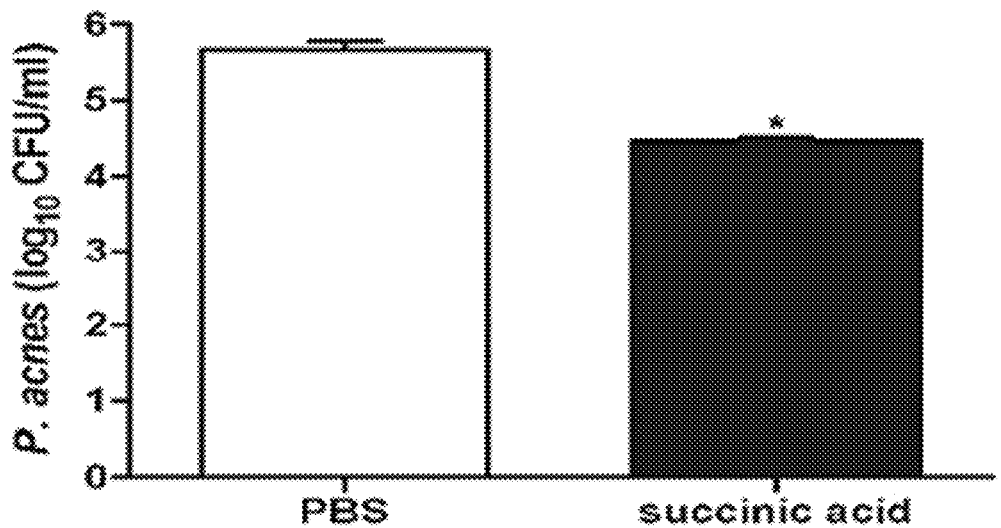

To examine the effectiveness of succinic acid as an intralesional injection therapy against acne causing P. acnes, mouse ears were intradermally injected with P. acnes for one day. The outbred Institute for Cancer Research (ICR) mice were used because they are polymorphic at a significant number of loci and have a complex genetic history similar to a human population. Injection of P. acnes into mouse ears of ICR mice thus represents an animal model for the granulomatous type of acne inflammation that follows follicular rupture. The succinic acid (20 μl; 5 mM, a MBC concentration) or its PBS control was then intralesionally injected into P. acnes-injected sites (FIG. 5). Injection of succinic acid reduced P. acnes-induced redness compared with injection of an equal amount of PBS (FIG. 5A). It has been known that P. acnes can induce the production of IL-8 via activation of toll-like receptor 2 (TLR-2). To determine whether succinic acid can reduce the production of P. acnes-induced inflammation, ears were homogenized two days after injection with succinic acid or PBS. The level of macrophage-inflammatory protein-2 (MIP-2), a murine counterpart of IL-8, was measured by an Enzyme-linked immunosorbent assay (ELISA). MIP-2 production in the ear injected with succinic acid was approximately 50% less than that detected in the ear injected with PBS (FIG. 5B). To determine the intensity of bacterial colonization, ears injected with succinic acid or PBS were homogenized to estimate the CFU. The P. acnes numbers in ears injected with PBS and succinic acid were $4.7 \times 10^5 \pm 1.3 \times 10^5$ and $2.9 \times 10^4 \pm 1.3 \times 10^4$ CFU, respectively, suggesting that succinic acid considerably decreased the growth of P. acnes in the lesions (FIG. 5C).

Since topical anti-acne agents can be used both as over-the-counter and clinic medicines, the potency of topical application of succinic acid against P. acnes was evaluated. One day after P. acnes injection, the surface of P. acnes-inoculated mouse ear was topically applied with 100 mM succinic acid or PBS once per day. Topical application of succinic acid considerably lowered the MIP-2 production as well as P. acnes colonization. Results above demonstrated that succinic acid is effective in the suppression of inflammation and P. acnes growth in vivo and could be utilized as a topical medication for the treatment and prevention of acne.

Example 2

Culture of Microorganisms.

USA300 or M. luteus (ATCC9341) was cultured on 3% tryptic soy broth (TSB) (Sigma, St. Louis, Mo., USA) agar overnight at 37° C. P. acnes (ATCC6919) was cultured on Reinforced Clostridium Medium (RCM, Oxford, Hampshire, England) under anaerobic conditions using Gas-Pak (BD, Sparks, Md., USA) at 37° C. All microorganisms from a single colony were cultured in their media. Overnight cultures were diluted 1:100 and cultured to an absorbance at 600 nm [optical density $(OD)_{600}$]=1.0. Microorganisms were harvested by centrifugation at 5,000 g for 10 min, washed with PBS, and suspended in PBS.

Anti-USA300 Overlay Assay.

The P. acnes ($10^5$ CFU) or M. luteus was inoculated in two parallel 2-cm streaks on 1.5% agar (Oxoid. Ltd., London, UK) plates containing rich medium [10 g/l yeast extract (Biokar Diagnostics, Beauvais, France), 5 g/l TSB, 2.5 g/l $K_2HPO_4$ and 1.5 g/l $KH_2PO_4$] in the absence and presence of 20 g/l glycerol under anaerobic conditions using Gas-Pak (BD, Sparks, Md., USA) at 30° C. for three days. Soft agar (1%) was cooled to 45° C. before USA300 bacteria were added to obtain a concentration of ($10^4$ CFU/ml). The soft agar (10 ml) was then poured onto the plates to overlay the rich medium agar. After incubation at 30° C. for 40 h under anaerobic conditions, the plates were examined visually.

To determine the MBC of propionic acid, USA300 ($10^6$ CFU/ml) were incubated with propionic acid at various concentrations (1.25-100 mM in PBS) as indicated in each individual experiment in media on a 96-well microplate (100 μl per well) overnight. The control received only PBS. After incubation, the bacteria were diluted 1:10-1:$10^6$ with PBS. MBC was finally examined at a 99.9% killing level and determined by spotting the dilution (5 μl) on an agar plate supplemented with media for the counting of CFUs. To determine the pH effect on the bacterial growth, USA300 in TSB was incubated with 2.5 mM propionic acid on a 96-well microplate (100 μl per well) overnight before spotting on an agar plate. As controls, USA300 was incubated with TSB (pH 6.8) alone, TSB (pH 5.8; a pH value corresponding to the MBC of propionic acid in TBS), or buffered propionic acid (25 mM propionic acid, pH 6.8 buffered with ammonium hydroxide).

P. acnes Fermentation and Inhibition of USA300 Growth.

P. acnes ($10^5$ CFU) was incubated in rich medium [10 g/l yeast extract; Biokar Diagnostics, Beauvais, France), 5 g/l TSB, 2.5 g/l $K_2HPO_4$ and 1.5 g/l $KH_2PO_4$] in the absence and presence of 20 g/l glycerol under anaerobic conditions using Gas-Pak (BD, Sparks, Md., USA) at 37° C. Rich medium plus 20 g/l glycerol without P. acnes was included as a control. The 0.001% (w/v) phenol red (Sigma, St. Louis, Mo., USA) in rich medium with 20 g/l glycerol served as an indicator, turning from red-orange to yellow when fermentation occurs. To assess the probiotic activity of fermentation products, P. acnes were incubated in phenol red-free rich medium with/without glycerol for seventeen days. After fermentation, P. acnes was discarded by centrifugation at 5,000×g for 30 min. Fermentation media were then passed through 0.2-μm-pore-size filters. After filtration, the initial medium of fermentation and its dilution (½ to ⅟₁₆) was added to USA300 ($10^6$ CFU/ml in TSB) on a 96-well microplate overnight. The plates were mixed well and then absorbance at 600 nm was measured by a microplate reader to estimate bacterial growth.

Radial Diffusion Assay.

USA300 bacteria in mid-log phase were centrifuged at 12,000×g for 10 min and washed with PBS. Bacteria ($10^5$ CFU/ml) were dispersed in agar consisting of 1% (w/v) agarose (Sigma, St. Louis, Mo., USA) and 3% (w/v) TSB in 10 mM PBS at 42° C. Subsequently, the agar was poured into Petri dishes and solidified. The wells (3 mm in diameter)

with a 30-μl capacity were created by poking a pipette tip into the semi-solidified agar. Five serially diluted samples of each propionic acid ranging in concentration from 5 to 100 mM were prepared, and 30-μl propionic acid aliquots or PBS were added to the wells. After 3 h of incubation, a 10-ml overlay gel composed of 3% TSB and 1% agarose was poured onto the plates, and the plates were incubated overnight to allow the surviving organisms to form microcolonies. The growth inhibition zones reflecting the antimicrobial activity of propionic acid were observed.

In Vivo Effect of Propionic Acid on Skin Infection of USA300.

ICR mice (2-3-month-old female) were anesthetized by isoflurane. In each experiment, there were five mice per group. A wound 5 mm in length was made on the dorsal skin after shaving with electrical clippers. Once the skin wound was created, 5 μl of propionic acid (100 mM), PBS (pH 7.1) or PBS (pH 3.5) was applied topically to the wounded areas. The wounds were left uncovered throughout the experimental period. For bacterial infection, USA300 ($2 \times 10^6$ CFU in PBS) was applied topically to the wounded areas 10 min after application of propionic acid or PBS. For the measurement of the extent of wound closure, a transparent parafilm was put on the top of the wounded skin. The wound area was marked on the parafilm by drawing an area which covered the whole skin wound. The lesion size was measured daily for 8 days was calculated using the ImageJ software [National Institutes of Health (NIH), Bethesda, Md., USA] and expressed as $mm^2$. Student's t-test was used to determine the significance of the differences between groups of the PBS (pH 7.1)- and propionic acid-treated mice as well as the PBS (pH 7.1)- and PBS (pH 3.5)-treated mice. Data represent the mean±SD from three independent experiments. All experiments using mice were conducted in a Biosafety Level 2 (BSL-2) facility and with accordance to institutional guidelines for animal experiments.

Figure 10A:
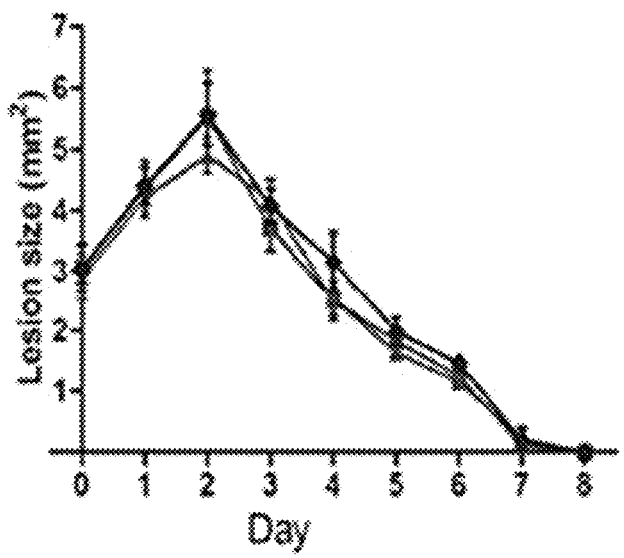
Figure 10B:
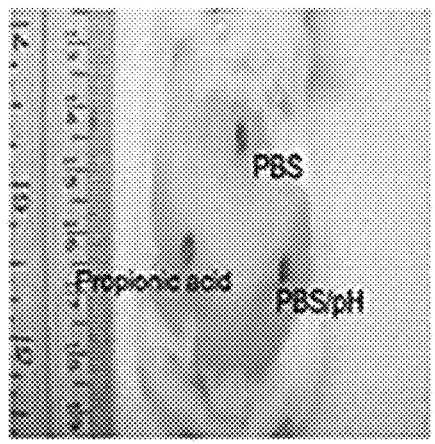
Figure 10C:
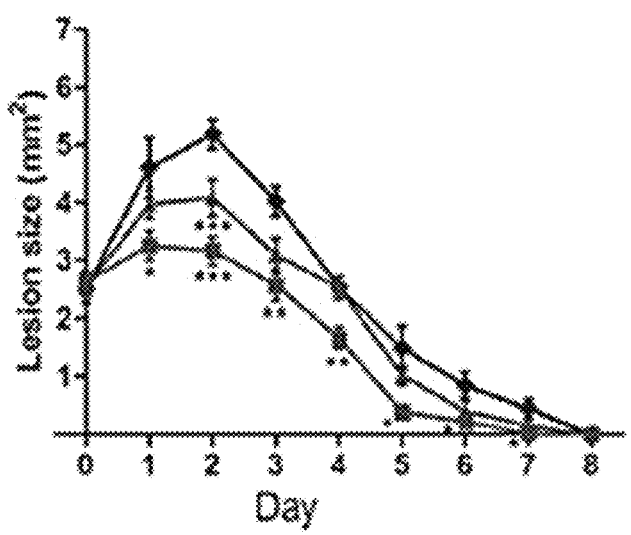
Figure 10D:
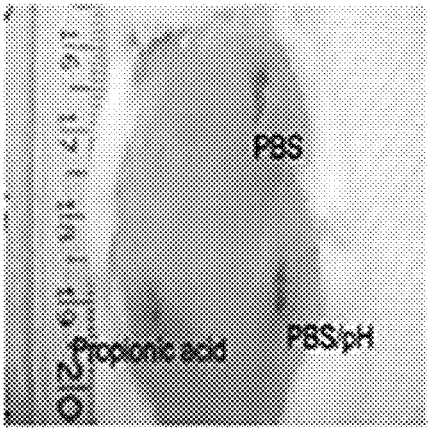

To test if propionic acid exerts antimicrobial activity, the MBC of propionic acid for USA300 was determined. USA300 is a predominant community methicillin-resistant MRSA clone. USA300 bacteria were incubated with propionic acid at various concentrations in media for 24 h at 37° C. After incubation, the bacteria were diluted with PBS and spotted on an agar plate to count CFU. Propionic acid effectively suppressed the growth of USA300 at a concentration of propionic acid greater than 25 mM, and complete killed USA300 at a concentration greater than 100 mM. To further validate the antimicrobial activity of propionic acid, a highly sensitive Radial Diffusion Assay was performed. The growth inhibition zones were clearly observed when USA300 bacteria were incubated with propionic acid at a minimum effective concentration of 25 mM The fermented media of P. acnes effectively suppressed the growth of USA300. The amount of propionic acid in fermented media was 4.1 μmole/ml, corresponding to 4.2 mM. The pH dropped from 6.8 to 5.8 when propionic acid at a concentration (25 mM) corresponding to its MBC was added into a culture of USA300 in TSB. To determine the suppression of the growth of USA300 by propionic acid is not mainly due to a pH decrease, USA300 ($10^6$ CFU) was incubated with TSB (pH 6.8), TSB (pH 5.8) or 25 mM propionic acid (pH 5.8) for 24 h. The bacterial numbers in USA300 treated with TSB (pH 6.8), TSB (pH 5.8) or 25 mM propionic acid (pH 5.8) were $9.4 \pm 0.1 \times 10^9$, $8.1 \pm 0.2 \times 10^9$ and $4.9 \pm 0.2 \times 10^4$ CFU/ml, respectively, suggesting that the suppression of the growth of USA300 mainly resulted from the antimicrobial activity of propionic acid itself. The antimicrobial activity of propionic acid remained after buffering 25 mM propionic acid (pH 6.8) with ammonium hydroxide. A 5-mm long excision wound was created on the back of ICR mice to study the antimicrobial activity of propionic acid to test the potency of propionic acid against S. aureus in vivo. USA300 ($2 \times 10^6$ CFU) was inoculated to the wounded areas 10 min after topical application of propionic acid (100 mM), PBS (pH 7.1) or PBS (pH 3.5, a value corresponding to pH for 100 mM propionic acid). Application of propionic acid considerably decreased the sizes of USA300-infected skin lesions in comparison with application of PBS (pH 7.1) (FIG. 10C). On Day 1, the sizes of USA300-infected skin lesions in PBS (pH 7.1)-, PBS/pH (pH 3.5)-, or propionic acid-treated wounds were 4.6±0.6, 4.0±0.8, and 3.2±0.8 mM, respectively. The morphology of USA300-infected skin lesions was pictured after application of propionic acid or its controls (FIG. 10D). A significant decrease in the size of USA300-infected skin lesion was also detected two days after application of PBS (pH 3.5). Histological observation (H&E staining) revealed that the propionic acid-treated wounds evoked a less pronounced inflammatory response and remained intact in terms of the integrity of epidermis and hair follicle in comparison with PBS (pH 7.1)- or PBS/pH (pH 3.5)-treated wounds (FIG. 10E), suggesting that propionic acid reduced USA300-induced damage of the epidermal layers and inflammation. To determine if propionic acid itself enhanced the wound healing, propionic acid and its controls were applied topically to the wounded areas without USA300 inoculation. The changes in lesion sizes of PBS (pH 7.1)-, PBS/pH (pH 3.5)-, and propionic acid-treated wounds were not statistically different during an 8-day period (FIG. 10A, B). Data above suggested that the decrease in the size of USA300-infected skin lesion resulted primarily from the antimicrobial activity of propionic acid. To determine the bacterial colonization, USA300-infected skin lesions treated with propionic acid and its controls were homogenized to estimate CFU. The bacterial numbers in lesions treated with PBS (pH 7.1), PBS/pH (pH 3.5) or propionic acid were $9.3 \pm 0.5 \times 10^9$, $9.0 \pm 0.8 \times 10^9$ and $6.9 \pm 0.7 \times 10^7$ CFU, respectively (FIG. 10F). Propionic acid significantly decreased the growth of USA300 in the skin lesions. The results indicated that pre-treatment of skin wounds with PBS/pH (pH 3.5) did not cause a significant change in bacterial numbers in lesions of mice. The results showed that propionic acid, P. acnes, or P. acnes fermentation media can be used for prevention and treatment of S. aureus and MRSA infection.

Histological Analysis and Bacterial Number in USA300-Infected Skin.

The USA300-infected skins treated with propionic acid and its controls were cross-sectioned, stained with hematoxylin and eosin (H&E) (Sigma, St. Louis, Mo.), and viewed on a Bx51 research microscope (Olympus, Melville, N.Y., USA). To determine the bacterial number in infected skin, the whole area of infected skin was excised 72 h after bacterial application. The excised skin was homogenized in 200 μl of sterile PBS with a hand tissue grinder. Bacterial CFUs in the skin were enumerated by plating serial dilutions ($1:10^1$-$1:10^6$) of the homogenate on a TSB agar plate. The plate was incubated for 24 h at 37° C. to count colonies.

Statistical Analysis.

To determine significances between groups, comparisons were made using the two-tailed t-test. For all statistical tests, the P-values of <0.05 (*), <0.01 (), and <0.001 (*) were accepted for statistical significance.

Probiotic Effects of *P. acnes* Fermentation Against USA300.

*P. acnes* (10¹ CFU/ml) was incubated in rich medium (10 ml) in the absence and presence of 20 g/l glycerol under anaerobic conditions using Gas-Pak (BD, Sparks, Md., USA) at 30° C. Rich medium plus 20 g/l glycerol without *P. acnes* was included as a control. The 0.001% (w/v) phenol red (Sigma, St. Louis, Mo., USA) in rich medium with 20 g/l glycerol served as an indicator, converting from red-orange to yellow when fermentation occurred. To assess the probiotic activity of fermentation products, *P. acnes* was incubated in phenol red-free rich medium with/without glycerol for seventeen days. After fermentation, *P. acnes* was discarded by centrifugation at 5,000 g for 30 min. Media were then passed through 0.2-µm-pore-size filters. After filtration, the initial medium or its dilution (½ to 1/16) was added to USA300 ($10^5$ CFU/ml in TSB) on a 96-well microplate overnight. The plates were mixed well and then $OD_{600}$ was measured by a microplate reader to estimate bacterial growth. The inhibitory growth of USA300 was defined as a decline in $OD_{600}$.

Measurement of intracellular pH. Measurement of intracellular pH of USA300 using a cFSE florescence probe (Life Technologies, Grand Island, N.Y., USA). Briefly, USA300 bacteria were loaded with cFSE (5 µM) for 30 min at 37° C. in 50 mM HEPES and 5 LM ethylenediaminetetraacetic acid (EDTA). To eliminate unbound probe, bacteria were incubated with glucose (10 mM) for an additional 30 min, washed twice in 50 mM PBS with 10 mM $MgCl_2$, pH 7.0, and then re-suspended in 1 mM PBS. The cFSE-loaded bacteria ($3 \times 10^4$ CFU) were dispensed in on a 96-well microplate containing 100 µl/per well of rich medium plus 20 g/l glycerol, or culture supernatants of *P. acnes* in rich medium in the absence and presence of 20 g/l glycerol. Fluorescence intensities were measured immediately and every min for 5 min using an excitation wavelength of 490 nm and emission wavelength of 520 nm. A drop in relative fluorescence indicated the decrease in intracellular pH. Fluorescence of the bacteria-free filtrate (background fluorescence) was measured after the 5-min assay. In this case, treated suspensions were centrifuged at 5,000 g for 5 min. The fluorescence of the bacteria-free supernatant was measured and deducted from values for the treated suspensions. Calibration curves were obtained by incubation of untreated, cFSE-loaded bacteria in buffers of various pHs. The buffer containing glycine (50 mM), citric acid (50 mM), $Na_2HPO_4 \cdot 2H_2O$ (50 mM), and KCl (50 mM) was adjusted to various pH values ranging from 4 to 10. Equilibration of the intracellular and extracellular pH was conducted by addition of 1 µM valinomycin and nigericin (Sigma, St. Louis, Mo., USA).

In Vivo Effects of Fermented Media and Propionic Acid on Skin Infection of USA300.

ICR mice (2-3 month-old females; Harlan Labs, Placentia, Calif., USA) were anesthetized by isoflurane. A 5 mm wounds were made on the dorsal skin following shaving with electrical clippers. Following skin wounding, 5 µl of filter sterilized media obtained by incubating *P. acnes* ($10^5$ CFU/ml in 10 ml) with/without glycerol for 17 days or 5 µl of media with glycerol (control) were applied and to the wounded areas. To determine if propionic acid can prevent or mitigate the MRSA infection, 5 µl of 100 mM propionic acid was applied to the wounded areas. Application of PBS/pH 3.5, corresponding to pH for 100 mM propionic acid) or PBS (pH 7.1) to the wounded areas served as controls. The wounds were left uncovered throughout the experimental period. USA300 ($2 \times 10^6$ CFU in 5 µl PBS) was then applied to the wounds 10 min after application of various media, propionic acid or PBS controls. To measure the extent of wound closure, a transparent parafilm was placed over the wounded skin and the area was marked by outlining the area of the wound. The lesion size ($mm^2$) was measured daily for 8 days then calculated with ImageJ software (NIH, Bethesda, Md., USA). Five mice per group per experiments were used. A Student's t-test was used to determine the significance of the differences between groups. Data represent the mean±SD from three independent experiments. All experiments using mice were conducted in a biosafety level 2 (BSL-2) facility and in accordance with institutional guidelines for animal experiments. To determine the bacterial counts in infected skin, the infected skin was excised 72 h following bacterial application. The excised skin was weighted and homogenized in 200 µl of sterile PBS with a tissue grinder. Bacterial CFUs in the skin were enumerated by plating serial dilutions ($1:10^1 - 1:10^6$) of the homogenate on a TSB agar plate. The plate was incubated for 24 h at 37° C. to count colonies. The bacterial numbers (CFUs) per gram of excised skin were calculated and presented as % of control.

Validation of *P. acnes* Glycerol Fermentation In Vivo by NMR Analysis.

The ear of ICR mice was intradermally injected with $^{13}C_3$-glycerol (0.2 mg) and *P. acnes* (ATCC6919; $10^7$ CFU in 10 µl PBS) for one, two or three days. The other ear of the same mouse received $^{13}C_3$-glycerol (0.2 mg) and PBS (10 µl) as a control. Supernatants (500 µl) of ear homogenates were mixed with 10% $D_2O$ for NMR analysis. The 1-D NMR spectra were measured on a JEOL-ECS NMR spectrometer (JEOL USA, Inc., Peabody, Mass., USA) operating at resonance frequency of 400 MHz with a repetition delay of 3 sec for $^{13}C$ NMR. The 2-D $^1H$-$^{13}C$ heteronuclear single quantum correlation (HSQC) NMR spectra were acquired on a Bruker Avance 600 MHz NMR spectrometer (Bruker Daltonics Inc., Fremont, Calif., USA) with a triple resonance inverse (TCI) cryo-probe and recorded as 2048×256 complex points with 32 scans and 1 sec repetition time. Newly appearing signals belong to the intermediates or final products resulting from $^{13}C_3$-glycerol fermentation by *P. acnes*.

Interference of *P. acnes* Fermentation with the Colonization of USA300 In Vivo.

A 5 mm wound made on the dorsal skin of ICR mice were described above. *P. acnes* bacteria ($10^7$ CFU in 5 µl PBS), *P. acnes* bacteria and glycerol (0.2 mg), PBS (5 µl) alone or glycerol alone were applied onto the skin wounds for 3 days. USA300 ($10^7$ CFU in 5 µl PBS) was administered onto the same wounds. The wounds were excised, weighted and homogenized 3 days after USA300 administration. Bacterial CFUs in the wounds were enumerated by plating serial dilutions ($1:10^1 - 1:10^6$) of the homogenate on a TSB agar plate. The plate was incubated for 24 h at 37° C. to count colonies of USA300.

Statistical Analysis.

To determine significances between groups, comparisons were made using the two-tailed t-test. For all statistical tests, the P-values of <0.05 (*), <0.01 (), and <0.001 (*) were accepted for statistical significance.

*P. acnes* Fermentation Counteracted USA300.

To examine if *P. acnes* fermentation affects the growth of USA300, *P. acnes* or *Micrococcus luteus* (*M. luteus*), a Gram-positive, non-fermenting skin commensal bacterium, was grown on agar plates in the presence or absence of glycerol for three days before growing USA300 in the overlaid agar. As shown in FIG. 8A, only *P. acnes* grown with glycerol showed visible inhibitory effects against USA300. No inhibitory effect was observed when *P. acnes* was grown in the absence of glycerol (FIG. 8C). *M. luteus* grown with or without glycerol did not display inhibitory effects against the growth of USA300 (FIGS. 8B and D). These findings showed that glycerol fermentation was required for inhibitory effect of *P. acnes* against USA300.

To test the probiotic effect of *P. acnes* fermentation products, *P. acnes* was incubated in rich medium under anaerobic conditions in the presence of glycerol as the carbon source. Rich medium plus glycerol and rich medium plus *P. acnes* were used as controls. To monitor the fermentation process, cultures were tested with phenol red, a fermentation indicator, to assess SCFA production as a result of glycerol fermentation. Only media in the culture of *P. acnes* with glycerol turned yellow (more acidic) ten days following incubation (FIG. 8E), demonstrating *P. acnes* fermentation. This was further validated quantitatively by pH values in rich medium containing glycerol, *P. acnes* and glycerol plus *P. acnes* of 6.6, 6.5, and 5.6 respectively, following 17 days of incubation. To assess the anti-CA-MRSA activity of *P. acnes* fermentation products, USA300 [$1\times10^5$ colony-forming unit (CFU)/ml] was then incubated with each group and their respective serial two-fold dilutions (½ to ¹⁄₁₆) overnight. Initial fermented media and its 1/dilution markedly suppressed the growth of USA300 (FIG. 8F).

Ferments of *P. acnes* Reduced the Intracellular pH of USA300.

To determine if *P. acnes* reduced the intracellular pH of USA300, the USA300 was loaded with an internally conjugated fluorescent pH probe, carboxyfluorescein succinimidyl ester (cFSE). Compared to control media, fermented media of *P. acnes* significantly lowered the intracellular pH of USA300 (FIG. 8G).

Identification of SCFAs in Fermentation Products of *P. acnes* by Nuclear Magnetic Resonance (NMR) Analysis.

Figure 14C:
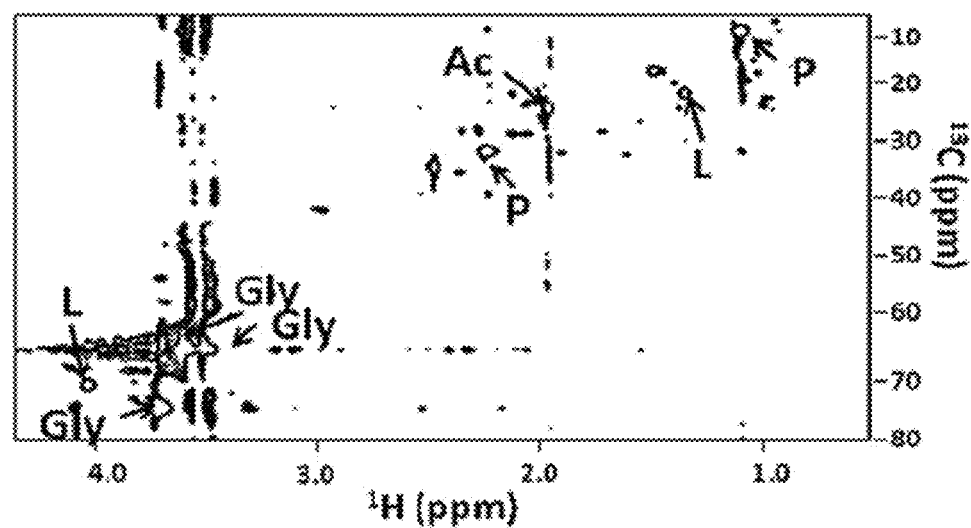

To identify the SCFAs in bacterial fermentation, *P. acnes* (ATCC6919) was incubated in rich media under anaerobic conditions in the presence of $^{13}C_3$-glycerol (20 g/l) for 17 days. The $^{13}C$-labeled metabolites in the fermentation products of *P. acnes* were identified by NMR analysis. In addition to un-metabolized $^{13}C$-glycerol (62.3 and 72.5 ppm), three SCFAs (acetic acid, lactic acid, and propionic acid) were detected in the fermentation productions of *P. acnes*. In a one-dimensional (1-D)$^{13}C$ NMR spectrum using an NMR spectrometer (400 MHz JEOL JNM-ECS) (FIG. 14A), two signals at 21.2 and 69.5 ppm corresponded to $^{13}C$-labeled lactic acid. Two $^{13}C$-labeled propionic acids appeared at 8.9 and 31.0 ppm. Acetic acid was detected at 24.3 ppm. The signals of acetic acid (1.90 ppm), lactic acid (1.33 and 4.09 ppm), and propionic acid (1.15 and 2.38) in a 1-D $^1H$ NMR spectrum were displayed in FIG. 14B. Three major SCFAs including propionic acid in the fermentation products of *P. acnes* were shown in a two-dimensional (2-D) $^1H$-$^{13}C$ HSQC NMR spectrum (FIG. 14C).

Fermentation Products of *P. acnes* Suppressed USA300-Infected Lesions and Bacterial Colonization.

Skin and soft tissue are the most common sites of *S. aureus* infection and comprise more than 75% of MRSA disease. Eradication of infected *S. aureus* in skin will prevent the bacteria entering the bloodstream. To mimic the natural route of CA-MRSA infection, a 5 mm wound was made on the dorsal skin of Institute of Cancer Research (ICR) mice and USA300 bacteria were topically applied onto the wound. To test the potency of *P. acnes* fermentation products against CA-MRSA in vivo, USA300 ($2\times10^6$ CFU) was inoculated to skin wounds 10 min after topical application of *P. acnes* ferments or controls. Application of fermented media, but not controls, considerably decreased the sizes of USA300-infected skin lesions (FIGS. 11A and B). To determine the intensity of bacterial colonization, wounds were homogenized to estimate the CFU. The USA300 counts in wounds applied with culture supernatants of medium plus glycerol, medium plus *P. acnes* or medium plus glycerol and *P. acnes* were $4.8\pm0.9\times10^6$, $4.9\pm2.6\times10^6$ and $9.4\pm4.5\times10^5$ CFU/g, respectively. These result showed that application of fermented media of *P. acnes* decreased 80% of USA300 colonization in the lesions as compared to application of control media (FIG. 11C).

Figure 15A:
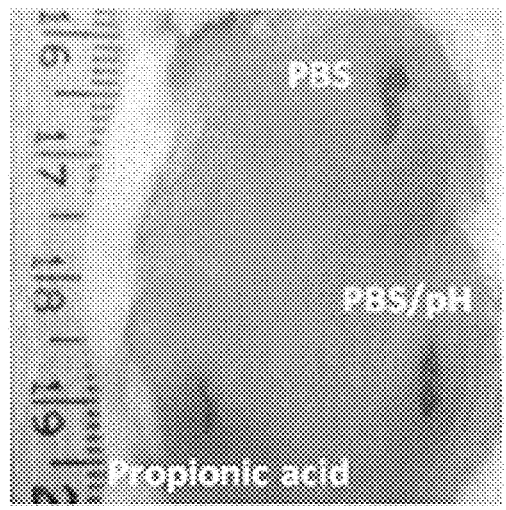
FIGS. 15A-B show suppression of USA300-infected lesions by propionic acid. A 5-mm long excision wounds were created on the back of ICR mice. To assess if propionic acid alleviates the lesions caused by USA300 infection, USA300 bacteria ($2 \times 10^6$ CFU) were applied onto the wounded areas 10 min after application of propionic acid (5 μl; 100 mM) or PBS (5 μl). (A) Skin lesions were pictured on day 3 after bacterial application. (B) Inflammation (arrows) surrounding the skin lesions (▼) was observed in the H&E-stained frozen sections [low (upper panels) and high (lower panels) powers] of skins applied with USA300 and controls. The scale bars of low power and high power were 40 μm, respectively.
Figure 15B:
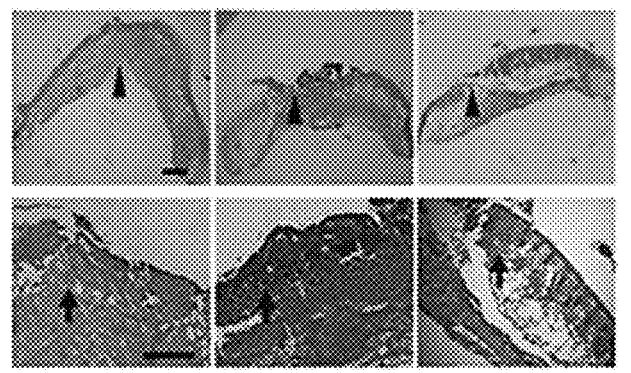

To examine if propionic acid exerts antimicrobial activity against CA-MRSA, the minimal bactericidal concentration (MBC) value of propionic acid for USA300 were determined. Bacteria were incubated with propionic acid at various concentrations in their media overnight at 37° C. After incubation, the bacteria were diluted with PBS and spotted on an agar plate to count CFU. Propionic acid effectively suppressed the growth of USA300 (FIG. 11D) at a concentration greater than 25 mM and completely killed all of bacteria at a concentration greater than 100 mM. To assess the antimicrobial activity of propionic acid in vivo, USA300 ($2\times10^6$ CFU) was inoculated to the wounded areas of ICR mice 10 min following topical application of either propionic acid (100 mM), PBS (pH 7.1) or acidic PBS (pH 3.5, corresponding to pH for 100 mM propionic acid). Application of propionic acid significantly reduced the size of USA300-infected skin lesions as compared to application of both PBS solutions (FIG. 11E). On Day 1, the sizes of USA300-infected skin lesions in PBS (pH 7.1)-, acidic PBS (pH 3.5)-, or propionic acid-treated wounds were $4.6\pm0.6$, $4.0\pm0.8$, and $3.2\pm0.8$ mm$^2$, respectively. A significant decrease in the size of USA300-infected skin lesion was detected two days following application of propionic acid. Histological observation [hematoxylin and eosin (H&E) staining] revealed that the propionic acid-treated wounds had an attenuated inflammatory response and improved integrity of epidermis and hair follicle compared to PBS-treated wounds (FIG. 15B). Propionic acid reduced USA300-induced damage of the epidermal layers and inflammation. To determine the bacterial colonization, USA300-infected skin lesions treated with propionic acid and controls were homogenized to determine CFU count. The bacterial numbers in lesions were: $1.9\pm1.0\times10^9$ (PBS, pH 7.1), $1.7\pm1.5\times10^9$ (PBS, pH 3.5) and $1.4\pm1.4\times10^7$ (propionic acid) CFU/g (FIG. 11F). Propionic acid significantly decreased the growth of USA300 in the skin lesions.

Fermentation of *P. acnes* Occurred in Mouse Skin.

Figure 12A:
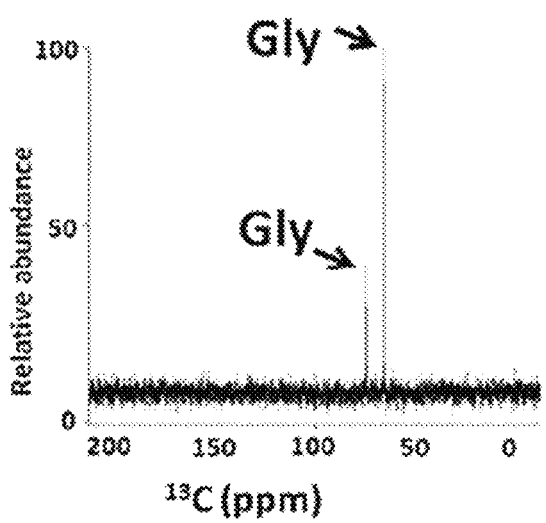
FIGS. 12A-C show NMR validation of fermentation of P. acnes in mouse skin. (A) The other ear of the same mouse received $^{13}C_3$-glycerol (0.2 mg) and PBS (10 μl) as a control. Supernatants of ear homogenates were mixed with 10% $D_2O$ and analyzed by a NMR (400 MHz JEOL JNM-ECS) spectrometer. Data from 1,024 scans were accumulated. The NMR signals (17.1 and 58.4 ppm) of $^{13}C$-ethanol (Et) metabolized from $^{13}C_3$-glycerol (Gly) were detected exclusively in the mice injected with $^{13}C_3$-glycerol and P. acnes. The un-metabolized $^{13}C_3$-glycerol appears between 60 and 80 ppm in the $^{13}C$-NMR spectrum. (B) The ear of ICR mice was intradermally injected with $^{13}C_3$-glycerol (0.2 mg) and P. acnes (ATCC6919; $10^7$ CFU in 10 μl PBS) for 3 days. (C) A 2-D $^1H$-$^{13}C$ HSQC NMR spectrum (600 MHz) was displayed. In addition to glycerol (Gly), ethanol (Et), four SCFAs [butyric acid (B), 3-hydroxy-butyric acid (3HB), lactic acid (L), and propionic acid (P)] were detected in the ear injected with glycerol and P. acnes.
Figure 12B:
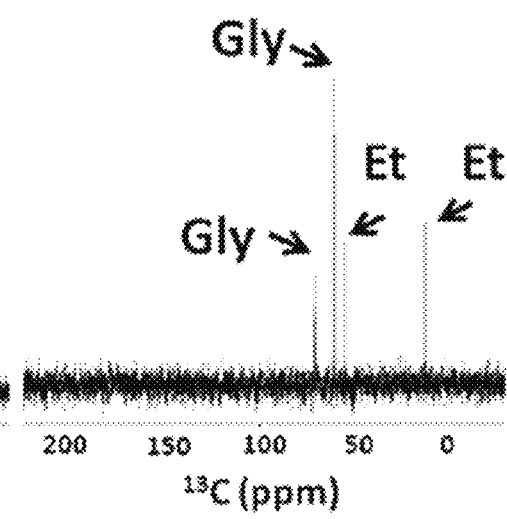
Figure 12C:
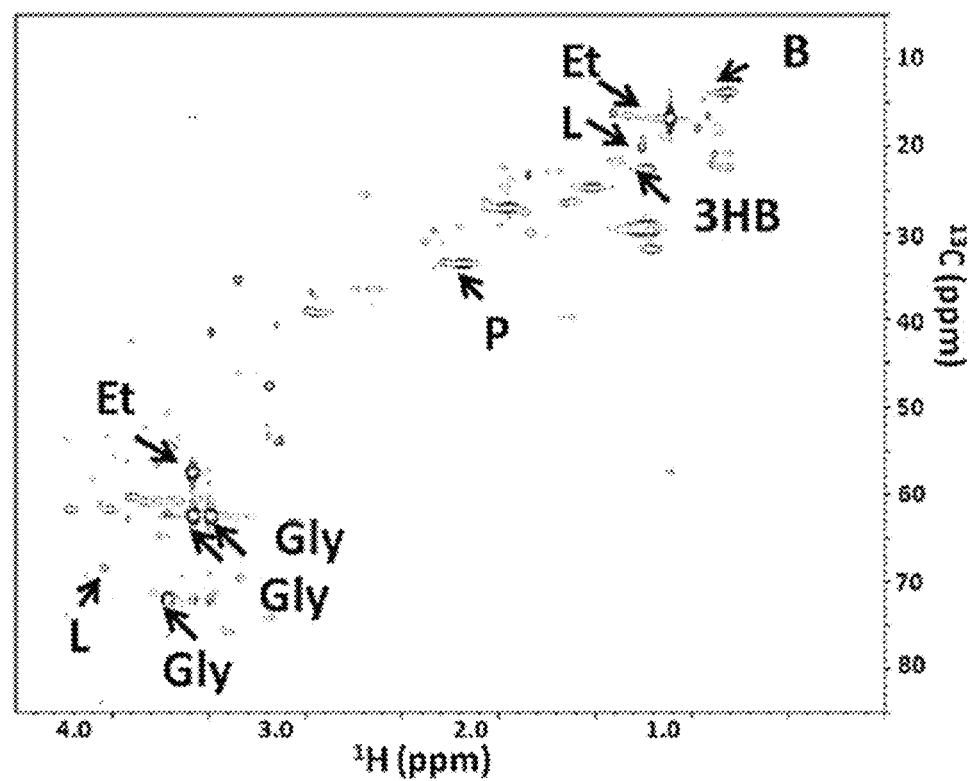

To determine if *P. acnes* is able to ferment carbon sources in vivo, ear of ICR mice was intradermally injected with $^{13}C_3$-glycerol (0.2 mg) immediately before injection of *P. acnes* (ATCC6919; $10^7$ CFU in 0 µl PBS). As a control, the same amount of $^{13}C_3$-glycerol and PBS was injected to the other ear. One, two and three days after injection, ears were excised, homogenized, and then centrifuged. Supernatants of ear homogenates in 10% deuterium oxide ($D_2O$) were subjected to 1-D $^{13}C$ NMR analysis. In addition to $^{13}C_3$-glycerol (62.3 and 72.5 ppm), two strong signals of $^{13}C$-labeled metabolites were detected at 17.1 and 58.4 ppm (FIG. 12B) in the mice injected with $^{13}C_3$-glycerol plus *P. acnes* for three days. No $^{13}C$-labeled metabolites, except $^{13}C_3$-glycerol, were detected in the mice injected with $^{13}C_3$-glycerol plus PBS (FIG. 12A). These two signals at 17.1 and 58.4 ppm correspond to the chemical groups (—$CH_3$ and —$CH_2OH$) of ethanol. In 1-D $^1H$ NMR analysis, two detected signals at 1.15 and 3.64 ppm validate the production of ethanol. To identify the SCFAs in the fermentation products, supernatants of ear homogenates in $D_2O$ were subjected to 2-D $^{13}C$ and $^1H$ NMR analysis. In addition to ethanol, four SCFAs (butyric acid, 3-hydroxy-butyric acid, lactic acid, and propionic acid) were detected in the ear injected with $^{13}C_3$-glycerol plus P. acnes (FIG. 12C).

P. acnes Fermentation in Skin Wounds Diminished the Colonization of USA300.

Figure 13B:
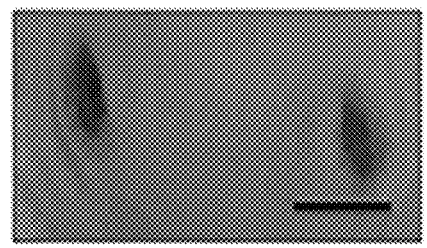

A wound made on the dorsal skin of ICR mice was topically applied with P. acnes ($10^7$ CFU in 5 µl PBS) or P. acnes and glycerol (0.2 mg) for three days. USA300 ($10^7$ CFU in 5 µl PBS) was subsequently administered onto the same wounds for additional three days. Compared to application of P. acnes alone, application of P. acnes and glycerol showed improved healing of the USA300-infected skin lesions (FIG. 13A). In addition, application of P. acnes and glycerol onto the wounds prior to administration of USA300 reduced more than 50% of USA300 colonization in comparison with application of P. acnes alone (FIG. 13C). To investigate the effects of glycerol alone on the USA300 colonization, PBS (5 µl) or glycerol (0.2 mg) was topically applied to skin wounds for three days followed by a 3-day USA300 infection. Compared to PBS, glycerol did not significantly alter the size of USA300-infected lesions (FIG. 13B) and USA300 colonization (FIG. 13D).

Example 3

Microorganisms.

P. acnes (ATCC 6919; American Type Culture Collection, Manassas, Va., USA) was cultured on Reinforced Clostridial Medium (Oxoid, Basingstoke, UK) under anaerobic conditions using Gas-Pak (BD, Sparks, Md., USA) at 37° C. S. aureus (USA300) was cultured on 3% tryptic soy broth (TSB) Sigma, St. Louis, Mo., USA) agar overnight at 37° C. E. coli BL21 (DE3) (Invitrogen, Carlsbad, Calif., USA) was cultured on Luria broth agar (Difco; BD) at 26° C. for 48 to 72 h. C. albicans (ATCC14053) was grown in an orbital incubator at 30° C. in 3% Sabouraud dextrose broth (Sigma) overnight. All microorganisms were cultured from a single colony. Overnight cultures were diluted 1:100 and cultured until they reached an optical density at 600 nm (OD600) of approximately 1.0. Microorganisms were harvested by centrifugation at 5,000×g for 10 min, washed with phosphate buffered saline (PBS) (pH 7.4), and suspended in an appropriate amount of PBS for further experiments.

Minimal Bactericidal and Fungicidal Concentration Tests.

To determine the minimal bactericidal concentration (MBC) and minimal fungicidal concentration (MFC) of propionic acid, microorganisms ($10^6$ colony forming units (cfu)/ml) were incubated overnight in media with propionic acid (1.25-2,000 mM) in a 96-well microplate (100 µl per well). The control only received PBS. After incubation, the microorganisms were diluted 1:10-1:$10^6$ into PBS. The dilutions (5 µl) were spotted onto agar media to count cfu; MBC/MFC were determined at 99.9% killing level. To determine the effect of pH on growth of S. aureus USA300, the bacterium was incubated in TSB at pH 5.8 and 6.8, and TSB with 25 mM propionic acid at pH 5.8 and 6.8 (buffered with 4-(2-hydroxyethyl)-1-piperazineethanesulfonic acid (HEPES)) in a 96-well microplate overnight before spotting onto agar plates.

Radial Diffusion Assay.

A radial diffusion assay (RDA) was performed as follows. Briefly, microorganisms in the mid-log phase were centrifuged at 12,000×g for 10 min, washed with PBS, and dispersed ($10^5$ cfu/ml) in agar consisting of 1% (w/v) agarose (Sigma) and 3% (w/v) culture medium in PBS at 42° C. Then, the agar was poured into Petri dishes and solidified. Wells (diameter 3 mm and volume 30 µl) were created by poking a pipette tip into the semi-solidified agar. Propionic acid was serially diluted in PBS to concentrations ranging from 5 to 2,000 mM, and 30 µl aliquots were added to the wells; PBS served as the control. After 3 h of incubation, a 10 ml overlay gel composed of 3% culture medium and 1% agarose was poured onto the plates, where after the plates were incubated overnight and examined for zones of growth inhibition.

Intracellular pH.

S. aureus USA300 bacteria were loaded with 5 µM carboxyfluorescein succinimidyl ester (cFSE) (Life Technologies, Grand Island, N.Y., USA) for 30 min at 37° C. in 50 mM HEPES and 5 mM ethylenediaminetetraacetic acid (EDTA) as previously described (Chitarra et al., 2000). To remove unbound probe, bacteria were incubated with glucose (10 mM) for an additional 30 min, washed twice in PBS with 10 mM $MgCl_2$ and resuspended in PBS. cFSE loaded USA300 ($3 \times 10^4$ cfu) were dispensed in a 96-well microplate (100 µl per well) containing 25 mM propionic acid or PBS. Fluorescence was measured for 5 min every min using an excitation wavelength of 490 nm and an emission wavelength of 520 nm. A reduction in relative fluorescence reflected a decrease in intracellular pH. Fluorescence of bacteria-free supernatant obtained by centrifugation at 5,000×g for 5 min after the 5-min assay was measured to correct for background fluorescence. Calibration curves were obtained by incubation of untreated, cFSE-loaded bacteria in buffer containing 50 mM glycine, 50 mM citric acid, 50 mM $Na_2HPO_4.2H_2O$ and 50 mM KCl adjusted to various pH values from 4-10. 1 µM valinomycin and nigericin (Sigma) were added to equilibrate the intracellular and extracellular pH.

Synthesis of Propionic Acid
2-(2-propionyloxyethoxy) Ethyl Ester 50 mmol propionic acid and 20 mmol diethylene glycol (DEG) in 100 ml dichloromethane were added to 60 mmol N,N'-dicyclohexyl carbodimide portion wise. The cloudy white suspensions were stirred at room temperature overnight, then filtered and washed with hexane. The filtrate was concentrated under reduced pressure to yield pure and colorless propionic acid 2-(2-propionyloxyethoxy)ethyl ester (PA-DEG-PA; >97%, 2.3 g), which was purified by chromatography (silica gel) eluted with 10% ethyl ethanoate/hexane. PA-DEG-PA was validated by 1H NMR (300 MHz) analysis (Avance DPX-300; Bruker, Fremont, Calif., USA) using chloroform solvent. Signals [δ 4.23 (m, 2H), 3.70 (m, 2H), 2.36 (J=8 Hz, 2H), 1.14 (J=8 Hz, 3H)] were detected in NMR spectroscopy.

Statistical Analysis.

All statistical tests were performed using a two-tailed t-test. P-values<0.05 were considered statistically significant.

Effect of Propionic Acid on Growth of USA300.

As described herein acetic acid, lactic acid and propionic acid were detected as products of glycerol fermentation by P. acnes in a 2-D $^1H$-$^{13}C$ heteronuclear single quantum correlation NMR spectrum. As S. aureus USA300 is a leading bacterial pathogen in both hospital and community settings, it was selected as a model pathogen for evaluation of the antimicrobial activity of propionic acid. Results from the MBC tests showed that propionic acid efficiently inhibited growth of USA300 more than 1 $\log_{10}$ reduction at concentrations greater than 25 mM, and completely killed the bacterium at concentrations greater than or equal to 100 mM. In addition, consistent with the results of the MBC tests, growth inhibition zones in radial diffusion assays were also clearly observed when USA300 was incubated with propionic acid at concentrations greater than 25 mM.

Effect of pH on Activity of Propionic Acid Against USA300.

The pH dropped from 6.8 to 5.8 when mM propionic acid at a concentration of 25 mM, which corresponded to the MBC, was added to a culture of USA300 in TSB. To validate that the growth suppression of USA300 by propionic acid was not due to the acidity of the medium, the bacterium were incubated in TSB at pH 5.8 and 6.8, and TSB with 25 mM propionic acid at pH 5.8 and 6.8 (buffered with HEPES) and the bacterial numbers after overnight incubation were calculated (FIG. 17A). The results showed that growth suppression of USA300 resulted from the antimicrobial activity of propionic acid and not from the acidity of the medium.

Effect of Propionic Acid on Intracellular pH of USA300.

Figure 17B:
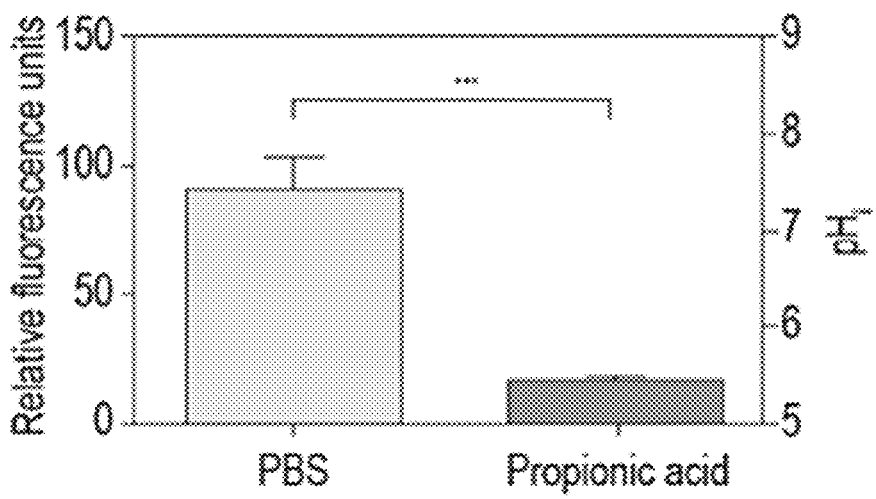

The bacteria were loaded with cFSE, an internally conjugated fluorescent probe, to determine intracellular pH. As shown in FIG. 17B, propionic acid, but not PBS, considerably lowered the intracellular pH of USA300. A reduction in intracellular pH caused by propionic acid was lethal to USA 300.

Effect of Propionic Acid on Growth of *Escherichia coli* and *Candida albicans*.

Figure 18A:
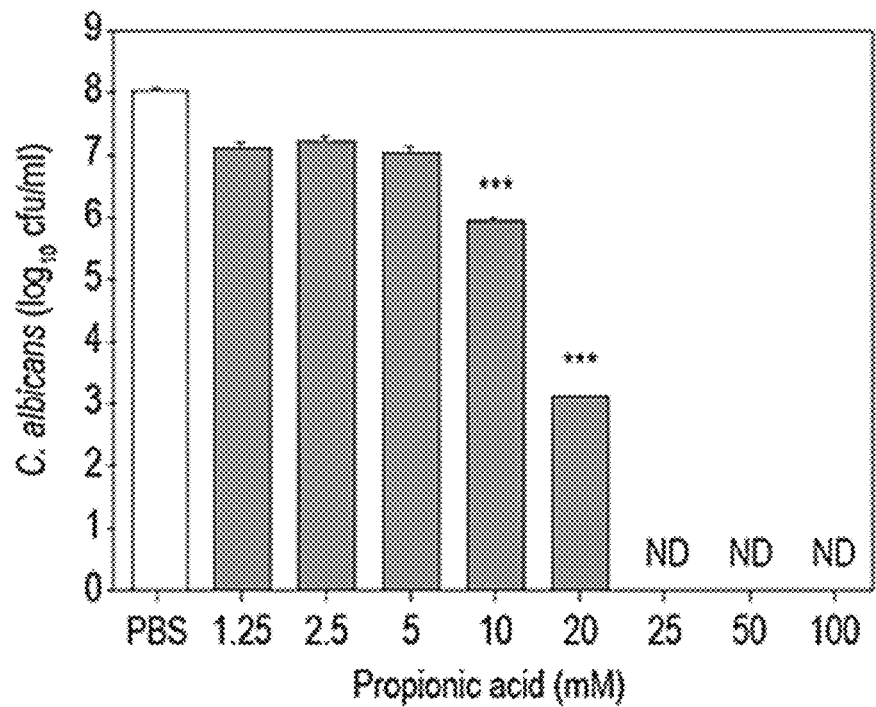

To examine if propionic acid exerts broad-spectrum antimicrobial activity, the effect of propionic acid was examined on *C. albicans*, a fungus that can cause superficial infections of skin and mucosal membranes, and *E. coli*, a Gram negative bacterium that causes a variety of infections and diseases. These pathogens were incubated with propionic acid at various concentrations in MBC tests. The propionic acid effectively suppressed the growth of *C. albicans* and *E. coli* (FIG. 18) at propionic acid concentrations greater than 10 mM, and completely killed them at concentrations greater than or equal to 25 and 50 mM, respectively. Consistent with the results of the MBC tests, growth inhibition zones in radial diffusion assays were observed when these pathogens were incubated with propionic acid at a minimum effective concentration of 10 mM.

Effect of Propionic Acid on *Propionibacterium acnes*.

To investigate if propionic acid exhibits antimicrobial activity against *P. acnes*, this bacterium was incubated with propionic acid at concentrations ranging from 5 to 2,000 mM in MBC tests and radial diffusion assays. As shown in FIG. 19, propionic acid at concentrations between 5 and 500 mM did not affect the growth of *P. acnes* in MBC tests. Growth inhibition was only detectable at concentrations greater than 1000 mM, indicating that *P. acnes* exhibited a high tolerance to propionic acid, which is produced by this bacterium during fermentation. Radial diffusion assays were consistent with these results. *S. aureus* showed higher sensitivity to propionic acid than *Staphylococcus epidermidis*, a Gram-positive bacterium predominately found on human skin. These findings suggest that the risk of propionic acid as a component of a skin probiotic to suppress the growth of dominant skin bacteria, such as *P. acnes* and *S. epidermidis*, is low.

Effect of Esterified Derivative of Propionic Acid on Growth of USA300.

Figure 20C:
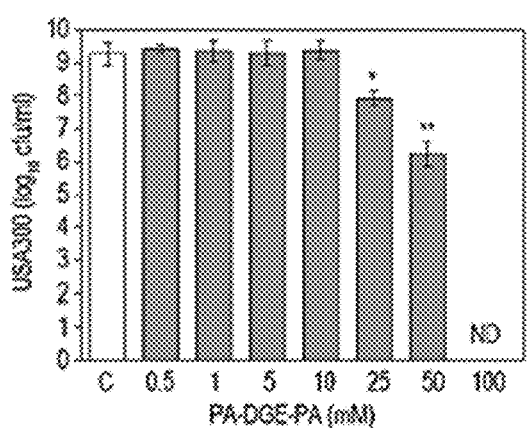
Figure 20D:
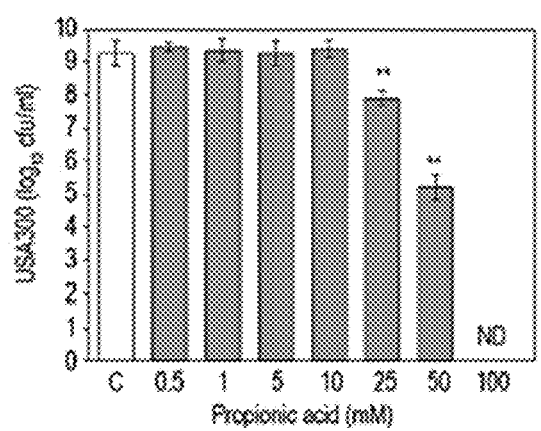

SCFAs have short half-lives and thus achieving pharmacologic concentrations in vivo is difficult. To achieve effective concentrations of SCFAs in the skin, various derivatives of propionic acid have been synthesized including derivatives such as SCFA esters that can be activated and release active SCFAs upon a contact with the skin. Experiments were performed using synthesized PA-DEG-PA, an esterified derivative of propionic acid that contains two active propionic acids esterified to a DEG linker (FIGS. 20A and B). MBC tests were conducted to assess its anti-*S. aureus* USA300 activity (FIG. 20C). To compare the effect of PA-DEG-PA with propionic acid, USA300 was incubated overnight with the same concentrations (0-100 mM) PA-DEG-PA or propionic acid, dissolved in 4% dimethyl sufoxide. The MBC (>1 $\log_{10}$ inhibition) of propionic acid was 25 mM and the concentration for a complete growth inhibition was 100 Mm (FIG. 20B). PA-DEG-PA also inhibited growth of USA300 by more than 1 $\log_{10}$ at a concentration ≥25 mM; growth inhibition was complete at 100 mM (FIG. 20B), suggesting that PA-DEG-PA was equivalent in efficacy to suppress the growth of USA300 in vitro.

A number of embodiments of the invention have been described. Nevertheless, it will be understood that various modifications may be made without departing from the spirit and scope of the invention. Accordingly, other embodiments are within the scope of the following claims.

REFERENCES CITED

All publications, patents, patent applications and other references cited in this application are incorporated herein by reference in their entirety for all purposes to the same extent as if each individual publication, patent, patent application or other reference was specifically and individually indicated to be incorporated by reference in its entirety for all purposes. Citation of references herein are provided solely for their disclosure prior to the filing date of the present application shall not be construed as an admission that such is prior art to the present invention. Nothing herein is to be construed as an admission that the inventors are not entitled to antedate such disclosure by virtue of prior disclosure. Specifically intended to be within the scope of the disclosure, and incorporated herein by reference in its entirety, is the following publication:

Y Wang et al. *Staphylococcus epidermidis* in the human skin microbiome mediates fermentation to inhibit the growth of *Propionibacterium acnes*: implications of probiotics in acne vulgaris Appl. Microbiol. Biotechnol. (2014) 98:411-424

M. Shu et al. Fermentation of *Propionibacterium acnes*, a Commensal Bacterium in the Human Skin Microbiome, as Skin Probiotics against Methicillin-Resistant *Staphylococcus aureus*. PLOS One. (February 2013) 8(2):1-11 (ePub e55380)

Y Wang et al. Propionic acid and its esterified derivative suppress the growth of methicillin-resistant *Staphylococcus aureus* USA300. Beneficial Microbes (2014) 5(2): 161-168.

What is claimed is:

1. A topical probiotic composition for producing or maintaining skin microbiome balance, the composition comprising

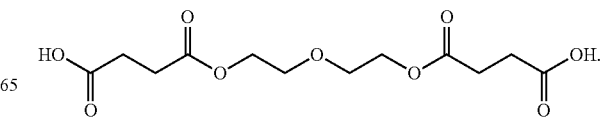

and one or more excipients for formulation as a lotion, shake lotion, soap, wipe, cream, spray, ointment, gel, foam, powder, solid, paste or tincture.

2. The topical probiotic composition of claim 1, capable of inhibiting the growth or spread of S. aureus or a methicillin-resistant *S. aureus* (MRSA) on skin.

3. The topical probiotic composition of claim 1, capable of inhibiting or preventing the infection of *S. aureus*, methicillin-resistant *S. aureus* (MRSA), a *Candida* species, or *E. coli* on skin.

4. The topical probiotic composition of claim 1, further comprising at least one probiotic commensal skin bacteria fermentation extract.

5. The topical probiotic composition of claim 4, wherein the probiotic commensal skin bacteria is selected from the group consisting of a Propionibacterium species, a *Paenibacillus* species, and a *Staphylococcus* species.

6. The topical probiotic composition of claim 1, further comprising glycerol.

7. The topical probiotic composition of claim 1, wherein the composition is formulated as a lotion, shake lotion, cream, ointment, gel, foam, powder, solid, paste or tincture.

8. A bandage or dressing comprising the topical probiotic composition of claim 1.

9. A method of treating or preventing a skin infection, the method comprising contacting the skin with the topical probiotic composition of claim 1.

10. The method of claim 9, wherein the skin infection is caused by *S. aureus*, methicillin-resistant *S. aureus* (MRSA), a *Candida* species, or *E. coli*.

* * * * *